(12) United States Patent
Tomer et al.

(10) Patent No.: US 10,802,262 B2
(45) Date of Patent: Oct. 13, 2020

(54) METHODS AND SYSTEMS FOR IMAGING A BIOLOGICAL SAMPLE

(71) Applicant: The Board of Trustees of the Leland Stanford Junior University, Stanford, CA (US)

(72) Inventors: Raju Tomer, Palo Alto, CA (US); Karl A. Deisseroth, Stanford, CA (US)

(73) Assignee: The Board of Trustees of the Leland Stanford Junior University, Stanford, Palo Alto ( * ) Notice: Subject to any disclaimer, the term of this patent is extended or adjusted under 35 U.S.C. 154(b) by 182 days.

(21) Appl. No.: 15/770,683

(22) PCT Filed: Oct. 27, 2016

(86) PCT No.: PCT/US2016/059205
§ 371 (c)(1),
(2) Date: Apr. 24, 2018

(87) PCT Pub. No.: WO2017/075275
PCT Pub. Date: May 4, 2017

(65) Prior Publication Data
US 2019/0056581 A1 Feb. 21, 2019

Related U.S. Application Data
(60) Provisional application No. 62/248,168, filed on Oct. 29, 2015.

(51) Int. Cl.
*G02B 21/36* (2006.01)
*G02B 21/00* (2006.01)
(Continued)

(52) U.S. Cl.
CPC ............ *G02B 21/367* (2013.01); *G01N 1/30* (2013.01); *G01N 1/312* (2013.01); *G01N 1/34* (2013.01);
(Continued)

(58) Field of Classification Search
CPC ............ G01N 1/30; G01N 1/312; G01N 1/34; G01N 33/5091; G02B 21/0032; G02B 21/0048; G02B 21/0076; G02B 21/367
(Continued)

(56) References Cited

U.S. PATENT DOCUMENTS
| | | |
|---|---|---|
| 4,734,578 A | 3/1988 | Horikawa |
| 8,178,496 B2 | 5/2012 | Trauner et al. |

(Continued)

FOREIGN PATENT DOCUMENTS
| | | | |
|---|---|---|---|
| CN | 110109239 A | * | 8/2019 |

OTHER PUBLICATIONS
Baker et al. (2008) "Genetically Encoded Fluorescent Sensors of Membrane Potential" Brain Cell Biol, 36:53-67.
(Continued)

*Primary Examiner* — Fernando Alcon
(74) *Attorney, Agent, or Firm* — Edward J. Baba; Bozicevic, Field & Francis LLP

(57) ABSTRACT

Provided herein is a method and system for imaging a biological sample. The method may include scanning a biological sample using one or more light sheets, where the biological sample is in a field of view of a microscope that includes an objective and a direction of observation of the objective defines a z-axis, where a point spread function of the microscope is elongated in the z-axial direction, and the biological sample is at a z-axial distance from the objective, thereby illuminating a plurality of z-axial slices of the biological sample, and recording a plurality of images
(Continued)

corresponding to a plurality of z-axial slices of the sample, where the images are generated by light patterns emitted from the scanned biological sample, thereby generating an image stack that includes a plurality of images of the biological sample.

38 Claims, 34 Drawing Sheets

(51) Int. Cl.
    *G01N 1/30*      (2006.01)
    *G01N 1/31*      (2006.01)
    *G01N 1/34*      (2006.01)
    *G01N 33/50*      (2006.01)

(52) U.S. Cl.
    CPC ..... *G01N 33/5091* (2013.01); *G02B 21/0032* (2013.01); *G02B 21/0048* (2013.01); *G02B 21/0076* (2013.01)

(58) Field of Classification Search
    USPC .................. 348/79; 359/381, 383, 385, 388
    See application file for complete search history.

(56) References Cited

U.S. PATENT DOCUMENTS

| | | | |
|---|---|---|---|
| 8,629,256 B2 | 1/2014 | Looger et al. | |
| 8,970,950 B2 | 3/2015 | Stelzer | |
| 9,110,301 B2 | 8/2015 | Lippert et al. | |
| 9,116,354 B2 | 8/2015 | Knebel et al. | |
| 9,134,521 B2 | 9/2015 | Huisken | |
| 2007/0171502 A1 | 7/2007 | Birk et al. | |
| 2009/0290156 A1* | 11/2009 | Popescu ............... | G02B 21/008 356/338 |
| 2010/0172020 A1 | 7/2010 | Price et al. | |
| 2011/0134521 A1 | 6/2011 | Truong et al. | |
| 2011/0279893 A1 | 11/2011 | Vizi et al. | |
| 2012/0034691 A1* | 2/2012 | Looger ............... | C07K 14/4728 435/348 |
| 2012/0154668 A1* | 6/2012 | Kimura ............... | G01C 3/32 348/348 |
| 2012/0264109 A1* | 10/2012 | Deka ............... | G01N 33/56972 435/5 |
| 2013/0148196 A1 | 6/2013 | Arnold | |
| 2013/0224756 A1 | 8/2013 | Cohen et al. | |
| 2014/0118524 A1* | 5/2014 | Munck ............... | G01N 21/6408 348/79 |
| 2015/0022881 A1* | 1/2015 | Loza Alvarez ........ | G02B 21/06 359/385 |
| 2015/0087001 A1* | 3/2015 | Gradinaru ............... | G01N 1/30 435/7.23 |
| 2015/0098126 A1* | 4/2015 | Keller ............... | G02B 21/0076 359/385 |
| 2016/0062098 A1* | 3/2016 | Brown ............... | G02B 21/0076 348/80 |

OTHER PUBLICATIONS

Berndt et al. (2014) "Structure-Guided Transformation of Channelrhodopsin Into a Light-Activated Chloride Channel" Science, 344:420-424.
Berndt et al. (2015) "Expanding the Optogenetics Toolkit" Science, 349:590-591.
Chung et al. (2013) "CLARITY for Mapping the Nervous System." Nature Methods, 10.6, 508-513.
Erttirk et al. (2012) "High-Resolution Imaging of Entire Organs by 3-Dimensional Imaging of Solvent Cleared Organs (3DISCO)." Experimental Neurology, 242, 57-64.
Guru et al. (2015) "Making Sense of Optogenetics" Intl. J. Neuropsychopharmacol, 1-8.
Hochbaum et al. (2014) "All-Optical Electrophysiology in Mammalian Neurons Using Engineered Microbial Rhodopsins" Nat Methods, 11:825-833.
Jiang et al. (2010) "Adaptive Optics Photoacoustic Microscopy" Optics Express, 18(21):21770-21776.
Keller et al. (2010) "Fast, High-Contrast Imaging of Animal Development With Scanned Light Sheet-Based Structured Illumination Microscopy" Nat. Methods, 7:637-642.
Mehta et al. (2011) "Reporting from the Field: Genetically Encoded Fluorescent Reporters Uncover Signaling Dynamics in Living Biological Systems" Annu Rev Biochem., 80: 375-401.
Mutoh et al. (2011) "Optogenetic Monitoring of Membrane Potentials" Exp Physiol, 96:13-18.
Noguchi et al. (2011) "In Vivo Two-photon Uncaging of Glutamate Revealing the Structure—Function Relationships of Dendritic Spines in the Neocortex of Adult Mice" J Physiol, 589:2447-2457.
Olivier et al. (2009) "Two-Photon Microscopy With Simultaneous Standard and Extended Depth of Field Using a Tunable Acoustic Gradient-Index Lens" Optics Letters 34(11)1684-1686.
Renier et al. (2014) "iDISCO: A simple, Rapid Method to Immunolabel-large Tissue Samples for Volume Imaging." Cell, 159.4, 896-910.
Silvestri et al. (2014) "Correcting Spherical Aberrations in Confocal Light Sheet Microscopy: A Theoretical Study" Microsc. Res. Tech, 77:483-491.
Stelzer et al. (2015) "Light-Sheet Fluorescence Microscopy for Quantitative Biology" Nat. Methods, 12:23-26.
Tainaka et al. (2014) "Whole-body Imaging With Single-Cell Resolution by Tissue Decolorization." Cell, 159.4, 911-924.
Tian et al. (2012) "Neural Activity Imaging With Genetically Encoded Calcium Indicators." Prog Brain Res, 196, 79-94.
Tomer et al. (2014) "Advanced CLARITY for Rapid and High-Resolution Imaging of Intact Tissues." Nature Protocols, 9, 1682-1697.

* cited by examiner

Standard Light Sheet Scanning | SPED-LS Scanning | SPED-LS implementation

Comparison of SPED-LS extended PSF and air PSF 20x 0.4 NA
12 mm WD 10x 0.3 NA
16 mm WD 10x 0.25 NA
21 mm WD 4x 0.28 NA
29.5 mm WD 100 μm xy-projections

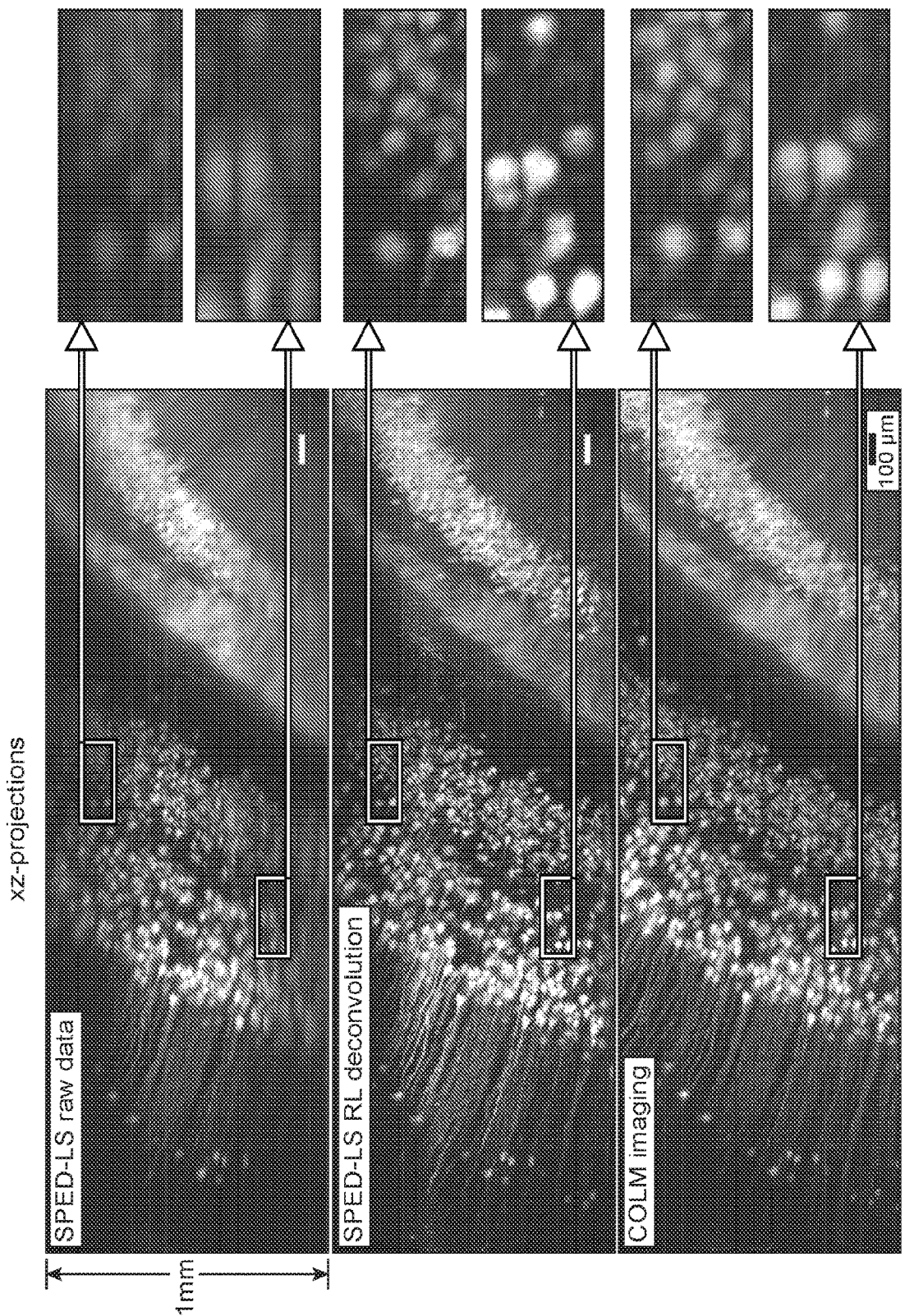

Cellular resolution whole nervous system imaging with SPED-LS

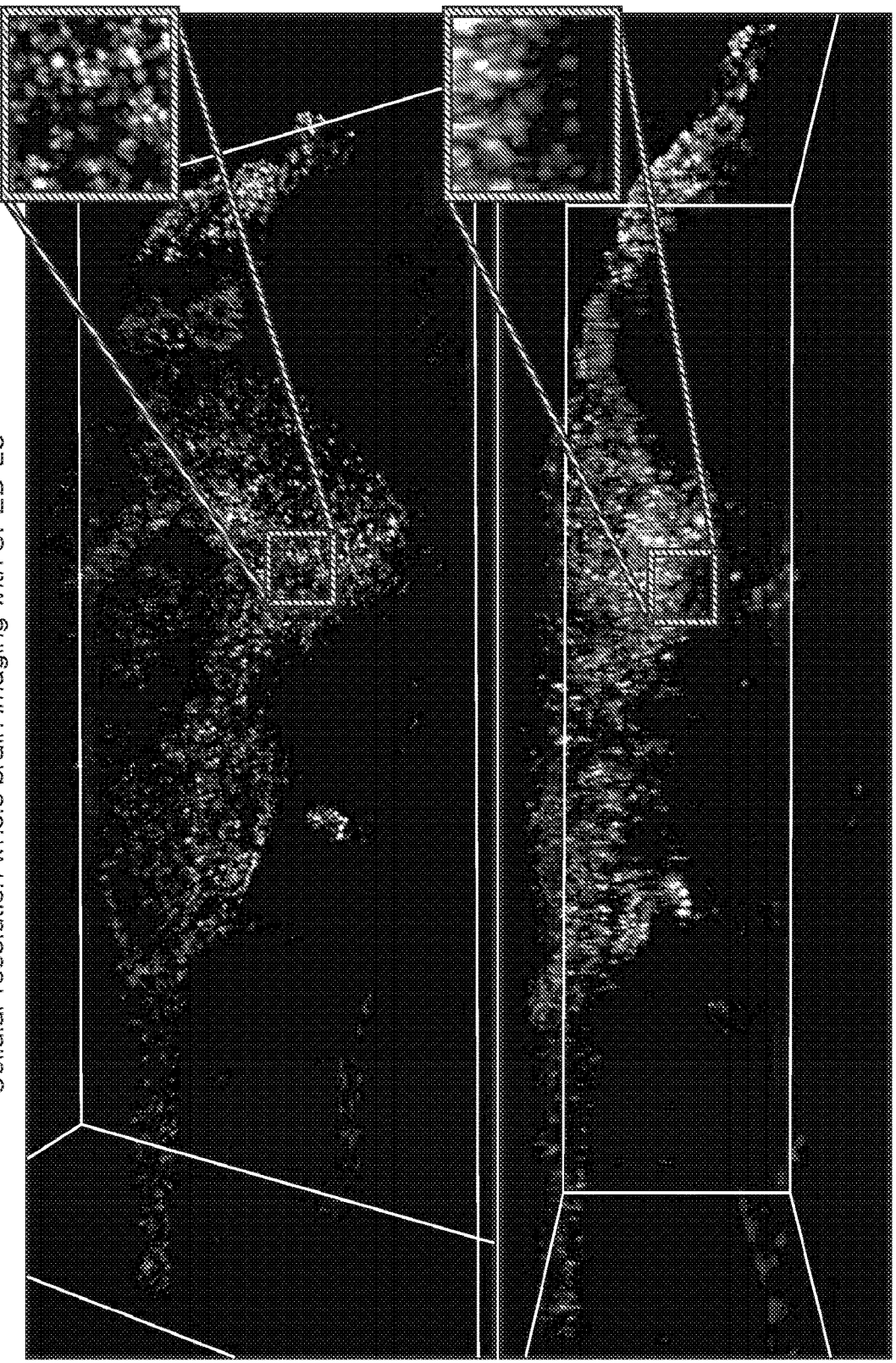
FIG. 3B Cellular resolution whole brain imaging with SPED-LS 100 sec

SPED-LS optical layout

SPED-LS prototyping on COLM framework

Sample mounted in thin-walled quartz cuvette

FIG. 9A
Zemax optical prescription used for SPED-LS PSF simulations
| | Comment | Radius | Thickness | Glass |
|---|---|---|---|---|
| OBJ | sample medium | inf | z+0.75 | 1.33 |
| 2 | cover glass | inf | 0.5 | 1.45 |
| 3 | RI material | inf | 10 to 50 | 1 to 1.7 |
| 4 | cover glass | inf | 0.1 | 1.45 |
| 5 | air gap | inf | 1 | 1.00 |
| 6 | objective | | f_obj | |
| STO | stop | inf | f_tl | 1.00 |
| 8 | tube lens | | sensor dist | |
| IMA | sensor | inf | | 1.00 |
FIG. 9B
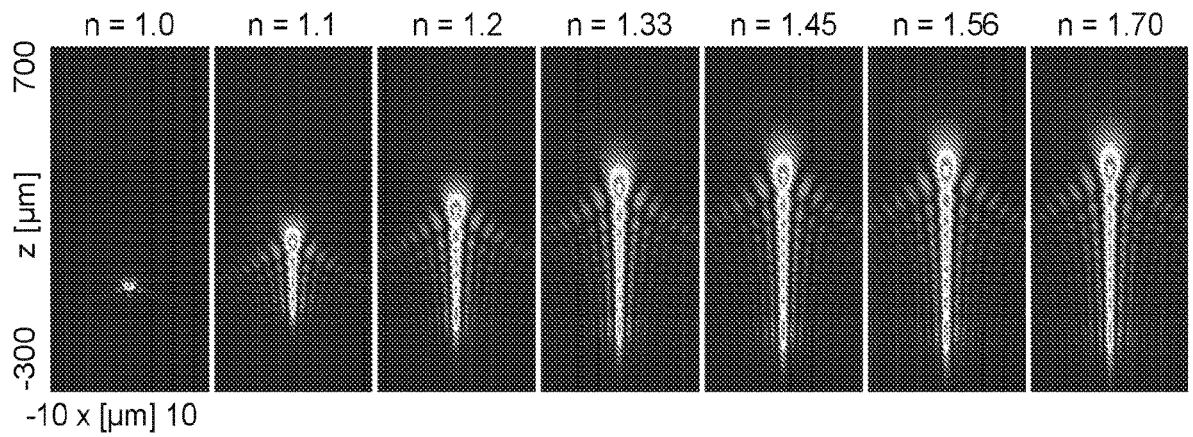
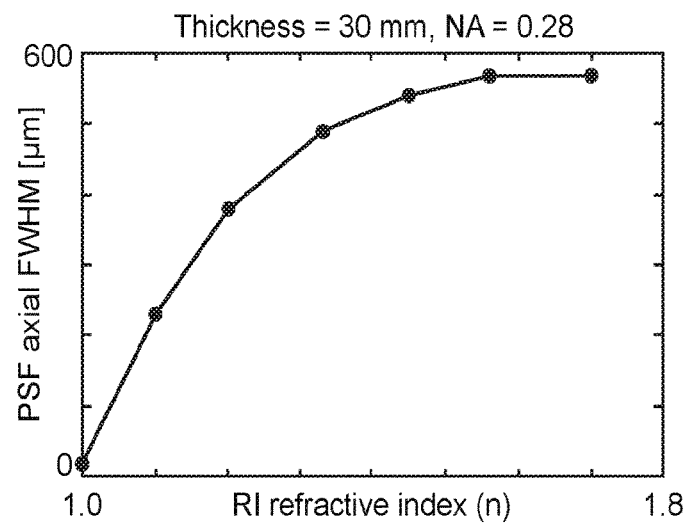

Activity time series traces of 99 most active neurons

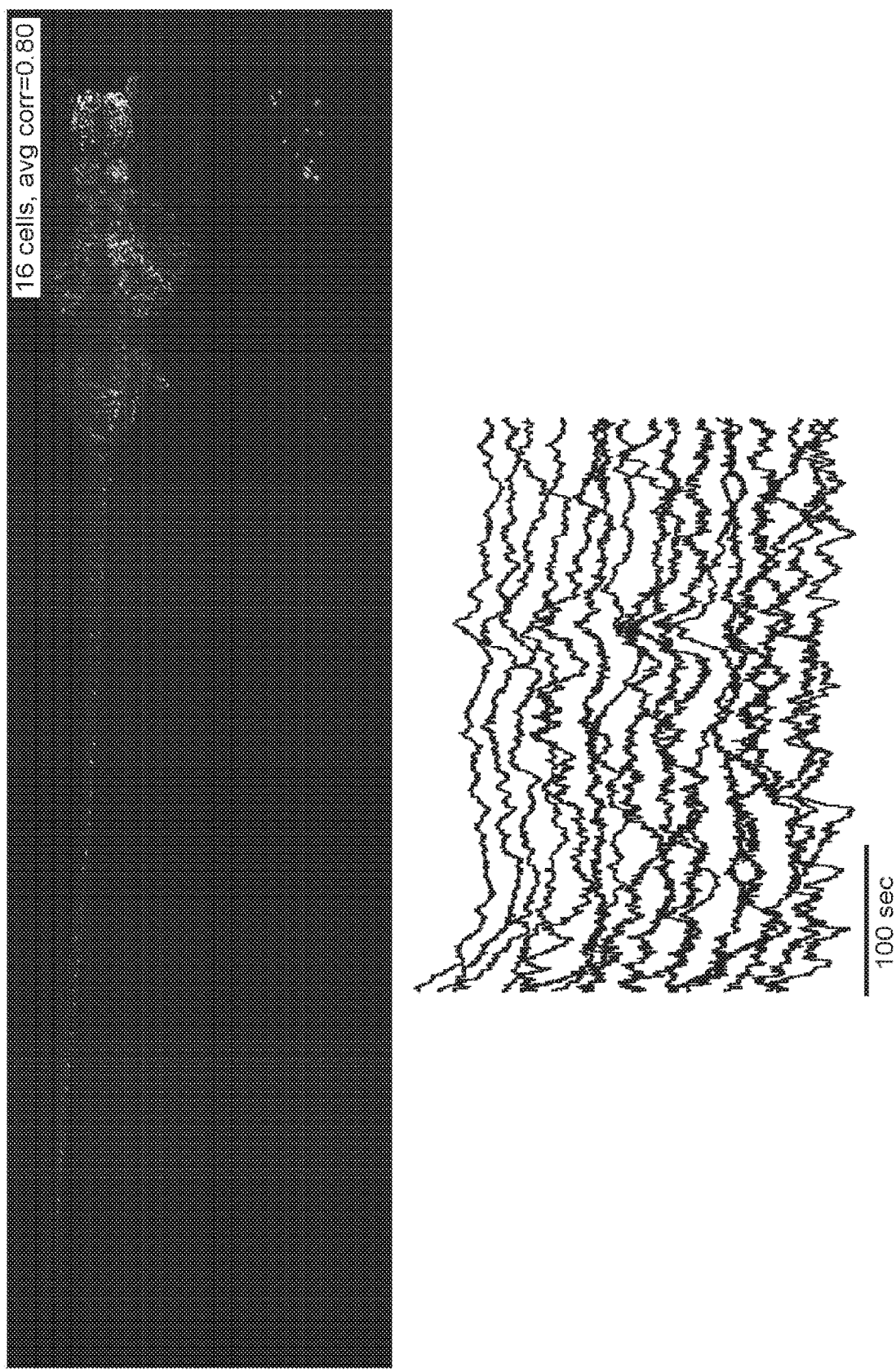

10 sec 10 sec

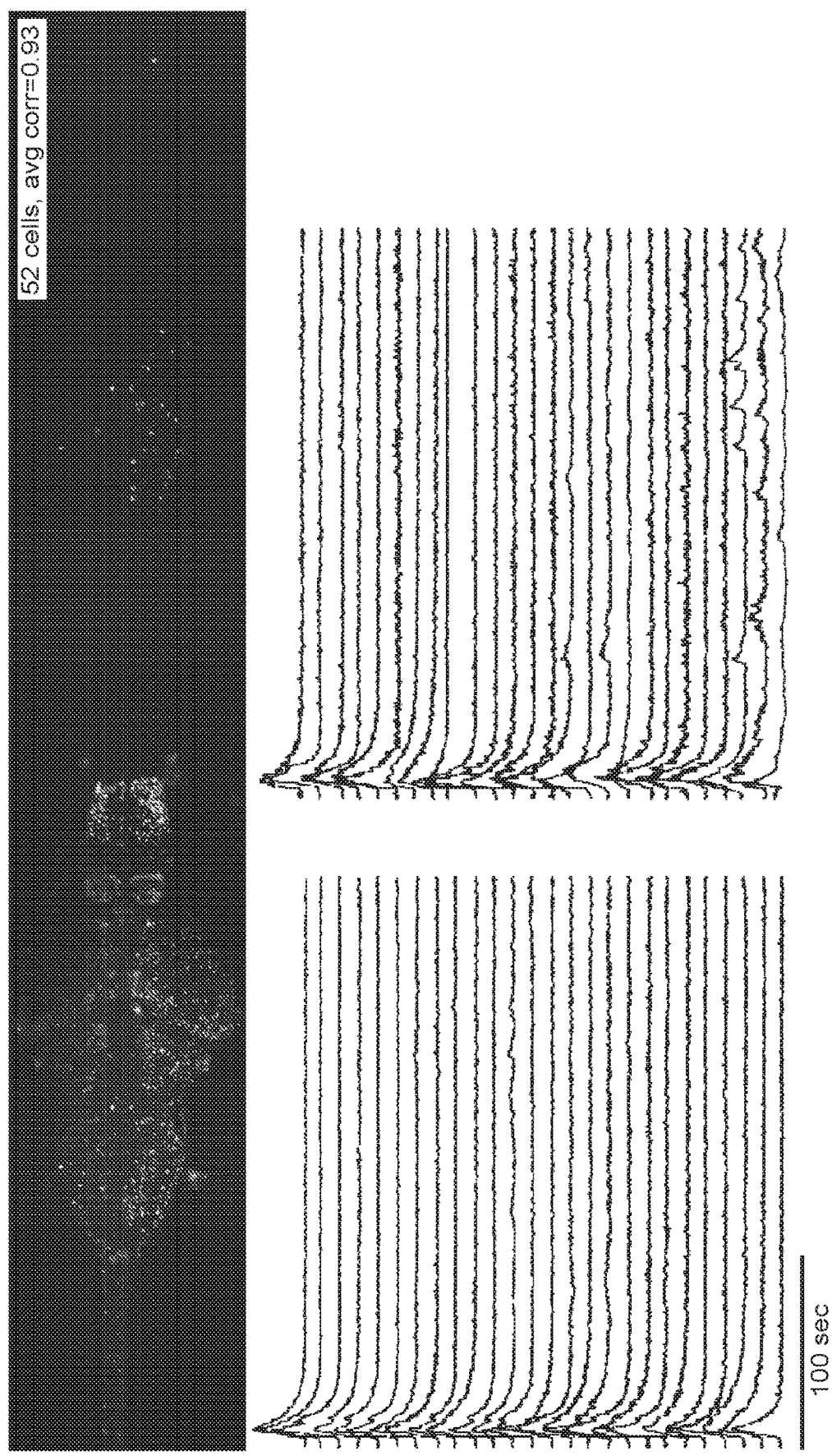

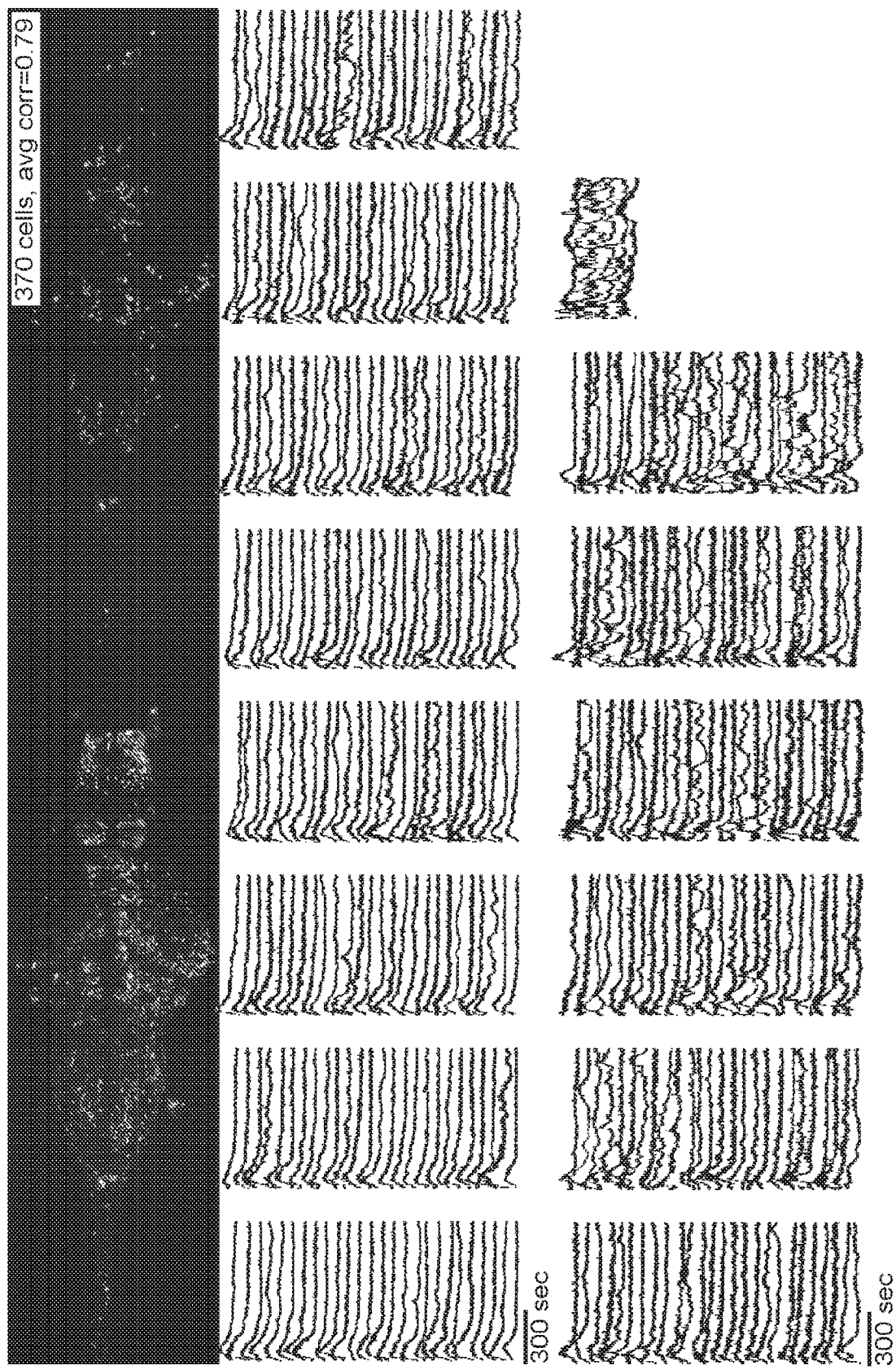

METHODS AND SYSTEMS FOR IMAGING A BIOLOGICAL SAMPLE

CROSS-REFERENCE TO RELATED APPLICATIONS

This application claims the benefit of U.S. Provisional Patent Application No. 62/248,168, filed Oct. 29, 2015, the disclosure of which is incorporated herein by reference in its entirety.

INTRODUCTION

Various optical and genetic tools have been developed to map cellular activity across entire vertebrate nervous systems at high spatiotemporal resolution. Fluorescent indicators of neuronal activity are increasingly used to optically measure neuronal activity in neurons. Methods for optical recording of neural activity at single cell resolution in three dimensions include serial scanning techniques such as two photon microscopy and wide field detection techniques such as light sheet and light field microscopy.

Two-photon microscopy is a multiphoton fluorescence technique, in which red-shifted excitation light is used to excite fluorescent molecules in a sample. In two-photon microscopy, two photons of light are absorbed for each excitation. In light field microscopy, a microlens array is inserted in to the optical path of a conventional microscope, which allows creation of focal stacks from a single image.

Light-sheet microscopy (LSM)-based approaches are used for functional imaging of ex-vivo mouse vomeronasal organ and small model organisms such as larval zebrafish brains, and are used in applications to developmental biology, cell biology, and high-resolution whole brain neuroanatomy. In carrying out light sheet microscopy, a thin slice of the sample is illuminated perpendicularly to the direction of observation, where the illumination is provided by a laser beam that is focused only in one direction (i.e., a light sheet).

SUMMARY

Provided herein is a method for imaging a biological sample, the method including a) scanning a biological sample using one or more light sheets, where the biological sample, or a portion thereof, is in a field of view of a microscope containing an objective a direction of observation of the objective defines a z-axis, where a point spread function of the microscope is elongated in the z-axial direction, and the biological sample is at a z-axial distance from the objective, thereby illuminating a plurality of z-axial slices of the biological sample; and b) recording a plurality of images corresponding to the plurality of z-axial slices of the sample, where the plurality of images are generated by a plurality of light patterns emitted from the scanned biological sample, thereby generating an image stack containing a plurality of images of the biological sample, or a portion thereof. In some embodiments, the microscope is configured to induce a spherical aberration in the recorded images.

Also provided herein is a method for imaging a biological sample, the method including a) scanning a biological sample using one or more light sheets, where the biological sample, or a portion thereof, is in a field of view of a microscope comprising an objective having an objective refractive index, where a direction of observation of the objective defines a z-axis and a medium is disposed between the sample and the objective, thereby illuminating a plurality of z-axial slices of the biological sample, each z-axial slice having an average slice thickness in the z-axial direction, where the medium has a refractive index that is different from the objective refractive index, and the biological sample is at a z-axial distance from the objective; and b) recording a plurality of images corresponding to the plurality of z-axial slices of the sample, where the plurality of images are generated by a plurality of light patterns emitted from the scanned biological sample, thereby generating an image stack comprising a plurality of images of the biological sample, or a portion thereof.

In some embodiments, the medium has a refractive index in the range of 1.0 to 2.0. In some embodiments, the medium has an average z-axial thickness in the range of 5 mm to 100 mm. In some embodiments, the refractive index of the medium is greater than objective refractive index. In some embodiments, the medium includes air, glass, water, glycerin, oil, or a combination thereof. In some embodiments, the objective has a numerical aperture in the range of 0.01 to 1.6. In some embodiments, the objective is an air objective.

In any embodiment, the scanning may include scanning the biological sample using two light sheets. In some embodiments, the biological sample is illuminated by the two light sheets from opposite sides of the biological sample. In some embodiments, the scanning includes using one or more mirror galvanometers to position the one or more light sheets at different z-axial positions of the biological sample. In some embodiments, the one or more light sheets illuminate a z-axial slice at the same z-axial position in the sample at a given time point during the scanning.

In any embodiment, the image stack may include a representation of a contiguous volume of the biological sample, wherein the volume has a z-axial depth greater than the average slice thickness of each of the plurality of z-axial slices.

In any embodiment, adjacent slices of the plurality of z-axial slices of the sample may be offset from each other by a distance in the range of 0.5 μm to 500 μm. In some embodiments, the one or more light sheets illuminates a z-axial slice having an average slice thickness in the range of 1 μm to 20 μm in the biological sample.

In any embodiment, the method may further include deconvolving each image of the image stack based on: i) a z-axial position of the image; and ii) a predetermined, z axis-dependent point spread function corresponding to the z-axial position of the image, thereby generating a deconvolved image stack comprising deconvolved images of the biological sample, or a portion thereof. In some embodiments, the predetermined, z axis-dependent point spread function is an empirically determined z axis-dependent point spread function. In some embodiments, the deconvolving comprises registering the image z-axial position with the predetermined, z axis-dependent point spread function. In some embodiments, the registering includes: deconvolving a reference image selected from an image of the image stack with a plurality of two-dimensional point spread functions at a plurality of z-axial positions of the predetermined, z axis-dependent point spread function, to generate a plurality of deconvolved reference images; and determining that the reference image z-axial position corresponds to a first z-axial position of a first two-dimensional point spread function when a first deconvolved reference image deconvolved by the first two-dimensional point spread function at the first z-axial position is optimized compared to other deconvolved reference images deconvolved by other two-dimensional point spread functions at other z-axial positions.

In any embodiment, the method may further include analyzing the one of more images of the image stack. In some cases, the analyzing includes registering, morphing, warping, aligning, counting and/or quantifying one or more properties associated with the one or more images.

In any embodiment, the recording may include detecting the light patterns with a charge-coupled device (CCD) or a complementary metal oxide semiconductor (CMOS) camera.

In any embodiment, the method may include scanning an area of the biological sample that is larger than the field of view of the microscope by horizontally translating the relative positions of the biological sample and the microscope.

In any embodiment, the biological sample may be labeled with a detectable label. In some embodiments, the biological sample is labeled with a labeled binding member that specifically binds to a cellular component in the biological sample. In some embodiments, the labeled binding member is a labeled antibody or a labeled nucleic acid.

In any embodiment, the biological sample may be a multicellular organism or a tissue. In some embodiments, the tissue is an animal tissue. In some embodiments, the tissue is diagnosed to be or is suspected of being a tumor, or a dysplastic, metaplastic or neoplastic growth. In some embodiments, the tissue is a biopsy tissue. In some embodiments, the tissue includes tissue from brain, eye, heart, liver, pancreas, muscle, bone, kidney, prostate, breast, cervix, lung, and/or ovary.

In any embodiment, the biological sample may be a clarified biological sample. In some embodiments, the method includes, before scanning the biological sample, clarifying the biological sample; and positioning the clarified biological sample in the field of view of the microscope. In some embodiments, the clarifying includes using CLARITY™; passive clarity technique (PACT); perfusion-assisted agent release in situ (PARS); SeeDB; ClearT; 3-dimensional imaging of solvent-cleared organs (3DISCO); immunolabeling-enabled 3-dimensional imaging of solvent-cleared organs (iDISCO); clear, unobstructed brain imaging cocktails and computational analysis (CUBIC); Scale and derivative methods thereof, hydrogel embedding, delipidation, or refractive index matching.

In any embodiment, the multicellular organism may be an animal. In some embodiments, the animal is a living animal.

In any embodiment, the biological sample includes one or more cells containing an indicator dye.

In some embodiments, the indicator dye is a genetically encoded indicator dye. In some embodiments, the indicator dye is a calcium indicator dye.

Also provided herein is a method of diagnosing a tissue sample, including obtaining a tissue sample from an individual; imaging the tissue sample according to a method of imaging a sample, as described herein, thereby generating an image stack comprising a plurality of images of the tissue sample, or a portion thereof; and analyzing, qualitatively or quantitatively, one or more images of the image stack for one or more features diagnostic of pathology, thereby diagnosing the tissue sample. In some embodiments, the pathology comprises immune infiltration, tissue rejection, tissue inflammation, and/or malignancy. In some embodiments, the one or more features include diagnostic molecular markers. In some embodiments, the analyzing includes determining a surgical margin. In some embodiments, the method is performed in one hour or less. In some embodiments, the method further includes imaging the tissue sample using confocal microscopy, two-photon microscopy, light-field microscopy, tissue expansion microscopy, and/or CLARITY™-optimized light sheet microscopy (COLM).

Also provided herein is a system for performing a method of the present disclosure. The system may include an optical element including a light microscope containing an objective, where a direction of observation of the objective defines a z-axis; a sample stage configured to hold a biological sample, or a portion thereof, in the field of view of the light microscope and at a z-axial distance from the objective; one or more illumination sources configured to generate one or more light sheets; one or more mirror galvanometers; and an image detector, where a point spread function of the optical element is elongated in the z-axial direction, where the system is configured to: scan the biological sample using one or more light sheets, where the light sheets are positioned, using the one or more mirror galvanometers, to illuminate a plurality of z-axial slices of the biological sample; direct, through the light microscope to the image detector, a plurality of light patterns emitted from the biological sample illuminated by the one or more light sheets; and record a plurality of images corresponding to the plurality of z-axial slices, where the plurality of images are generated by the plurality of light patterns, to generate an image stack comprising a plurality of images of the scanned biological sample, or a portion thereof. In some embodiments, the microscope is configured to induce a spherical aberration in the recorded images.

Also provided herein is a system for imaging a biological sample, including a light microscope containing an objective having an objective refractive index, where a direction of observation of the objective defines a z-axis; a sample stage configured to hold a biological sample, or a portion thereof, in the field of view of the light microscope and at a z-axial distance from the objective; one or more illumination sources configured to generate one or more light sheets; one or more mirror galvanometers; a medium having a refractive index different from the objective refractive index, where the medium is disposed between the sample and the objective; and an image detector, wherein the system is configured to: scan the biological sample using one or more light sheets, where the light sheets are positioned, using the one or more mirror galvanometers, to illuminate a plurality of z-axial slices of the biological sample; direct, through the light microscope to the image detector, a plurality of light patterns emitted from the biological sample illuminated by the one or more light sheets; and record a plurality of images corresponding to the plurality of z-axial slices, each z-axial slice having a slice thickness in the z-axial direction, where the plurality of images are generated by the plurality of light patterns, to generate an image stack comprising a plurality of images of the scanned biological sample, or a portion thereof.

In some embodiments, the medium has a refractive index in the range of 1.0 to 2.0. In some embodiments, the medium has a z-axial thickness in the range of 5 mm to 100 mm. In some embodiments, the medium has a refractive index higher than the objective refractive index. In some embodiments, the medium includes air, glass, water, glycerin, oil, or a combination thereof.

In any embodiment, the objective may have a numerical aperture in the range of 0.1 to 1.6. In some embodiments, the objective is an air objective.

In any embodiment, the image stack may include a representation of a contiguous volume of the biological sample, wherein the volume has a z-axial depth greater than the thickness of the z-axial slices.

In any embodiment, the system may include two or more light sheet sources. In some embodiments, the system includes two light sheet sources configured to illuminate the sample from opposite sides.

In any embodiment, the light sheet sources may be configured to illuminate a z-axial slice having an average thickness in the range of 1 µm to 20 µm in the biological sample.

In any embodiment, the system may further include: a processor; and a computer-readable medium containing instructions that, when executed by the processor, deconvolves each image of the image stack based on: i) a z-axial position of the image; and ii) a predetermined, z axis-dependent point spread function corresponding to the z-axial position of the image, to generate a deconvolved image stack comprising deconvolved images of the biological sample, or a portion thereof.

In any embodiment, the image detector may be a charge-coupled device (CCD) or a complementary metal oxide semiconductor (CMOS) camera.

BRIEF DESCRIPTION OF THE DRAWINGS

FIGS. 2A-2C are a collection of images showing imaging depth for SPED light sheet microscopy, according to embodiments of the present disclosure.

FIGS. 3A-3B are a collection of images showing cellular-resolution imaging of a biological sample using SPED light sheet microscopy, according to embodiments of the present disclosure.

FIGS. 9A-9D are a collection of a table, images and graphs showing SPED light sheet PSF simulation parameters and results, according to embodiments of the present disclosure.

FIGS. 16A-16B are collections of images and graphs showing synchronously active neuronal ensembles in whole-nervous system time series data measured using SPED light sheet microscopy, according to embodiments of the present disclosure.

FIGS. 18A-18B are additional collections of images and graphs showing synchronously active neuronal ensembles in whole-nervous system time series data measured using SPED light sheet microscopy, according to embodiments of the present disclosure.

DEFINITIONS

Figure 1A:
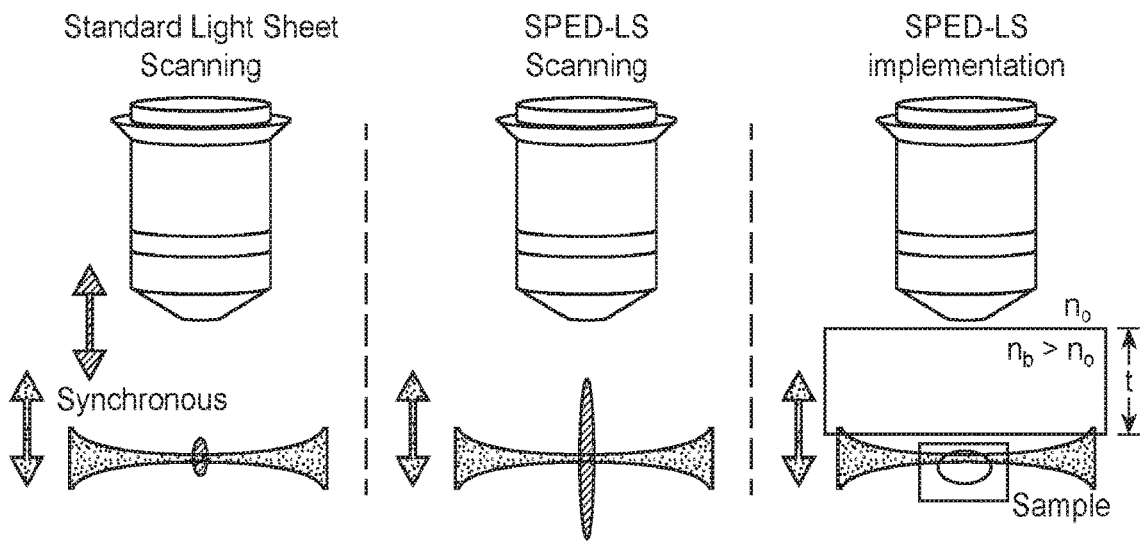
FIGS. 1A-1D are a collection of diagrams, images and graphs depicting parameters of a point spread function in Spherical-aberration-assisted Extended Depth-of-field (SPED) light sheet microscopy, according to embodiments of the present disclosure.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

"Substantially" as used herein, may be applied to modify any quantitative representation that could permissibly vary without resulting in a change in the basic function to which it is related. For example, a light sheet and a direction of observation defining a z-axis may permissively have a somewhat non-perpendicular orientation relative to each other if the images generated by the light patterns emitted from the sample upon illumination by the light sheet are not materially altered.

The term "genetic modification" refers to a permanent or transient genetic change induced in a cell following introduction into the cell of a heterologous nucleic acid (i.e., nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

"Field of view," as used herein, refers to the maximum area over the surface of a sample that can be accessed optically by a component of the present microscope system at a given relative position of the sample and the component.

"Image detector," as used herein, refers to any device that includes an optical sensor for detecting a two dimensional image formed by the incident electromagnetic radiation. Thus the image detector may detect in two dimensions the electromagnetic radiation impinging upon a focal plane positioned on the optical sensor. In certain cases, an image detector excludes devices, e.g., photomultiplier tubes (PMTs), which are configured to detect electromagnetic radiation without regard to the location of the source of radiation within the imaged target.

"Biological sample" and "sample" are used interchangeably, and include a sample containing cells and/or tissue from an organism. The organism may be a multicellular organism. The organism may be an animal, e.g., nematode, insect, annelid, mollusc, fish, amphibian, reptile, bird, mammal, including mouse, rat, monkey, non-human primate, human, etc. The biological sample may be a living sample, or may be processed for microscopic imaging, e.g., fixed, stained, and/or clarified. An "individual" may be any suitable organism, as described above. In some cases, the individual is a patient, e.g., a human patient.

"Scanning" as used herein, refers to a translational movement of a light pattern, e.g., a light beam or light sheet, across a three-dimensional space along one dimension, where the light pattern at a first time point during the translational movement is substantially parallel to the light pattern at a second time point. Scanning may be achieved by a unidirectional movement of the light pattern, or may involve one or more changes in direction of the movement of the light pattern. Scanning may be achieved by a continuous, quasi-continuous, or pulsed light pattern, or combinations thereof.

A "light sheet" refers to a light beam that is focused in only one direction to have a substantially rectangular cross-section, perpendicular to the illumination direction, that is thin in a first cross-sectional direction (e.g., a thickness) in comparison to a longer second cross-sectional direction (e.g., a width), perpendicular to the first cross-sectional direction. The light sheet may be a static light sheet, e.g., generated by cylindrical lens system, or may be a quasi-static light sheet, e.g., generated by scanning the plane with a light beam, where the scanning is achieved within an integration time of an image detector. "Scanning using a light sheet" is meant to indicate translating the light sheet along a direction substantially perpendicular to a plane defined by the longer cross-sectional direction (e.g., the width) and the illumination direction of the light sheet. A "slice" of a sample illuminated by a light sheet refers to a three-dimensional area of the sample at which the light sheet is focused to have the substantially rectangular cross-section. As the light sheet is focused to illuminate a thin volume, the three-dimensional area of the sample illuminated by the light sheet may be described as a planar section, e.g., a planar section having thickness, defining a plane. A "z-axial slice" refers to a slice having an orientation, where the plane of the slice is substantially perpendicular to a z-axis.

"Objective", as used herein, refers to an optical component, e.g., of a light microscope, which optical component can gather and focus light rays. A detection objective may gather light from a sample that is being observed, to produce a real image. An illumination objective may focus a light source to generate a light sheet that illuminates a slice, e.g., planar section, of the sample. In some cases, an objective may include one or more optical elements (e.g., lens, mirror, and/or combinations thereof).

"Objective refractive index" refers to the refractive index of a light microscope objective, for which refractive index the objective is designed to function optimally.

"Medium refractive index" refers to the refractive index of a medium disposed in the space between a light microscope objective and a sample to be observed. The medium refractive index may be the refractive index of the medium that induces a spherical aberration in images recorded by a device or system of the present disclosure.

"Front lens", as used herein, refers to an optical element (e.g., lens) of a microscope objective that is positioned closest to a sample being observed.

"Elongated", as used in reference to a point spread function (PSF), is meant to indicate a lengthening in the shape of a three-dimensional PSF preferentially in one dimension (e.g., the z-direction) compared to the extent of the PSF in the other two dimensions (e.g., the x- and y-directions), in comparison to a PSF optimized towards a diffraction-limited PSF (i.e., towards the theoretical limit of the optical instrument).

"Asynchronous", as used herein, is meant to indicate that two or more actions are individually taken at different times, i.e., not simultaneously. The two or more actions may be taken in sequence, or may be intervened by other events.

"Z axis-dependent" as used in reference to a point spread function is meant to denote a planar point spread function that is a component of a three-dimensional point spread function and that is defined according to the z-axis position of the plane relative to the detection objective. The planar point spread function may be in an x-y plane that is perpendicular to the z axis.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an image" includes a plurality of such images and reference to "the objective" includes reference to one or more objectives and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

A method of imaging a biological sample is provided. The method may include a) scanning a biological sample using one or more light sheets, wherein the biological sample, or a portion thereof, is in a field of view of a microscope containing an objective and a direction of observation of the objective defines a z-axis, where a point spread function of the microscope is elongated in the z-axial direction, and the biological sample is at a z-axial distance from the objective, thereby illuminating a plurality of z-axial slices of the biological sample; and b) recording a plurality of images corresponding to the plurality of z-axial slices of the sample, where the plurality of images are generated by a plurality of light patterns emitted from the scanned biological sample, thereby generating an image stack containing a plurality of images of the biological sample, or a portion thereof. Also provided is a system that finds use in performing the method as described herein.

Systems

A system of the present disclosure may be described with reference to FIGS. 1A and 7A. However, it is noted that the figures may show an example of the specific components of a system for imaging a biological sample, and that other embodiments of the present system are envisioned to be within the scope of this disclosure, by substituting the specific components with equivalent structural and/or equivalent functional components known in the art.

The present system for imaging a biological sample includes a light microscope. The light microscope may be any suitable light microscope. The light microscope may include a sample stage for holding a biological sample, and one or more objectives, e.g., detection objectives, for observing the sample, where the refractive index of the medium ($n_b$) between the objective front lens and the sample is different (e.g., greater than or less than) from the objective refractive index ($n_o$). In some cases, the objective is designed to function optimally when the refractive index of the medium ($n_b$) between the objective front lens and the sample is different (e.g., greater than or less than) from the objective refractive index ($n_o$). In the present system, the optical component of the system (e.g., microscope body, light source(s), lens(es), mirror(s), mirror galvanometer(s), filter(s), objective(s), camera, etc.) may be configured such that the point spread function (PSF) of the optical component as a whole is elongated in the direction of observation of the objective (e.g., elongated along the z-axis). In some cases, as shown in FIGS. 1A and 7A, a medium with a refractive index ($n_b$) that is different from (e.g., greater than or less than) the objective refractive index ($n_o$) is positioned between the sample and the detection objective to elongate the PSF. By increasing or reducing the refractive index of the medium ($n_b$) relative to $n_o$, the thickness of the medium (t), and/or the numerical aperture of the objective (NA), the PSF of the microscope may be elongated along the direction of observation of the detection objective (e.g., z-axis) while maintaining a relatively constant lateral extent of the PSF (e.g., in the x-y plane). In other words, in some cases, light emitted from the biological sample, e.g., upon illuminating with a light sheet, as described further below, travels through a medium having a refractive index that is different (e.g., higher or lower) than the objective refractive index along a suitable distance between the objective and the biological sample to induce spherical aberration and/or elongate the PSF of the microscope.

A system of the present disclosure may include an illumination source to generate a light sheet and illuminate the biological sample with the light sheet. The illumination source may include a light source as well as additional optical elements (e.g., illumination objective, tube lens, mirror, filter, collimator, etc.) to generate a light sheet that illuminates a slice, e.g., planar section, of the sample. A plane defined by the longer cross-sectional direction (e.g., width) and the illumination of direction of the light sheet may be substantially perpendicular to the direction of observation (e.g., the z-axis). Thus, the plane defined by the light sheet may be aligned in a substantially parallel orientation with the x-y plane of observation. FIG. 7B shows an example of the relative positions and orientations of a detection objective, sample, and illumination objectives, which are configured to generate light sheets that illuminate the sample.

In certain embodiments, the system includes one or more illumination sources, such as two illumination sources in some cases. The system may include an illumination objective associated with each illumination source. Thus, the system may include one or more illumination objectives, such as two illumination objectives. In some instances, the illumination objectives are placed opposite to each other relative to the sample, and two light sheets are directed to the sample from opposite sides of the sample. Thus, in some instances, the sample is illuminated by two light sheets from opposite sides of the sample.

The path of the light beam from the light source may be adjustable, e.g., using a mirror galvanometer, such that the generated light sheet can scan the biological sample and illuminate different z-axial slices of the sample. However, as planar sections with different z-axial positions are illuminated in the sample, the position of the detection objective relative to the sample may not need to be adjusted because of the elongated PSF of the microscope. Thus, the present system can image a biological sample in three-dimensions by scanning a biological sample in the z-direction using light sheet illumination through different sample depths (along the z axis), and capturing the light patterns emitted from the sample, while maintaining a constant distance between the detection objective and the sample (i.e., the distance between any given illuminated z-axial slice of the sample and the objective can be different from one position of the light sheet to another during the scanning process).

The light pattern emitted by the biological sample upon illumination with the light sheet is collected by the detection objective and directed through the light microscope to an image detector (e.g., a complementary metal oxide semiconductor (CMOS), such as a scientific complementary metal oxide semiconductor (sCMOS) camera, or a charge-coupled device (CCD), and the like), where a two-dimensional image is recorded. The present system can include a suitable computer to store, view, process, and/or analyze the recorded image.

In some embodiments, the ratio of the PSF full width at half-maximum (FWHM) in the z-axial direction of the present system is elongated by 2 fold or more, e.g., 3 fold or more, 4 fold or more, 5 fold or more, 10 fold or more, 20 fold of more, 50 fold or more, including 100 fold or more, and is elongated by 1000 fold or less, e.g., 300 fold or less, 200 fold or less, 100 fold or less, 50 fold or less, 20 fold or less, 10 fold or less, 8 fold or less, including 5 fold or less, relative to the PSF FWHM in the z-axial direction of a comparable system that has a substantially diffraction-limited PSF in three dimensions. In some embodiments, the ratio of the PSF FWHM in the z-axial direction of the present system is elongated by a range of 2 to 1000 fold, e.g., 3 to 300 fold, 4 to 100 fold, including 5 to 50 fold, relative to the PSF FWHM in the z-axial direction of a comparable system that has a substantially diffraction-limited PSF in three dimensions. The lateral spread (i.e., FWHM in the x-y plane) of the elongated PSF of the present system may be less than 2 fold of the lateral spread of the PSF of a comparable system that has a substantially diffraction-limited PSF in three dimensions, along at least about 30% or more, e.g., about 40% or more, about 50% or more, about 60% or more, 70% or more, 80% or more, 90% or more, including 95% or more, or the z-axial length of the elongated PSF.

In some embodiments, the ratio of the PSF FWHM in the z-axial direction of the present system, in which the space between the objective and the biological sample is substantially occupied by a medium having a refractive index different from the objective refractive index, is elongated by 2 fold or more, e.g., 3 fold or more, 4 fold or more, 5 fold or more, 10 fold or more, 20 fold of more, 50 fold or more, including 100 fold or more, and is elongated by 1000 fold or less, e.g., 300 fold or less, 200 fold or less, 100 fold or less, 50 fold or less, 20 fold or less, 10 fold or less, 8 fold or less, including 5 fold or less, relative to the PSF FWHM in the z-axial direction of a comparable system in which the space between the objective and the biological sample is substantially occupied by a medium having a refractive index matching the objective refractive index. In some embodiments, the ratio of the PSF FWHM in the z-axial direction of the present system, in which the space between the objective and the biological sample is substantially occupied by a medium having a refractive index different from the objective refractive index, is elongated by a range of 2 to 1000 fold, e.g., 3 to 300 fold, 4 to 100 fold, including 5 to 50 fold, relative to the PSF FWHM in the z-axial direction of a comparable system in which the space between the objective and the biological sample is substantially occupied by a medium having a refractive index matching the objective refractive index. The lateral spread (i.e., FWHM in the x-y plane) of the elongated PSF of the present system, in which the space between the objective and the biological sample is substantially occupied by a medium having a refractive index different from the objective refractive index, may be less than 2 fold of the lateral spread of the PSF of a comparable system that has a substantially diffraction-limited PSF in three dimensions, along at least about 30% or more, e.g., about 40% or more, about 50% or more, about 60% or more, 70% or more, 80% or more, 90% or more, including 95% or more, or the z-axial length of the elongated PSF.

In some embodiments, the elongated PSF is characterized by an average PSF FWHM of a 1 µm fluorescent bead in the z-axial direction of 2 µm or more, e.g., 3 µm or more, 4 µm or more, 5 µm or more, 10 µm or more, 50 µm or more, 100 µm or more, 500 µm or more, including 1,000 µm or more, and an average PSF FWHM of a 1 µm fluorescent bead in the z-axial direction of 10,000 µm or less, e.g., 5,000 µm or less, 2,000 µm or less, 1,000 µm or less, 900 µm or less, 800 µm or less, 700 µm or less, including 500 µm or less. In some embodiments, the elongated PSF is characterized by an average PSF FWHM of a 1 µm fluorescent bead in the z-axial direction in the range of 2 µm to 10,000 µm, e.g., 3 µm to 5,000 µm, 4 µm to 2,000 µm, 5 µm to 1,000 µm, 10 µm to 900 µm, 50 µm to 800 µm, 100 µm to 700 µm, including 100 µm to 500 µm.

As used herein, the term "average" refers to the arithmetic mean.

The PSF of the present system may be elongated using any suitable method. In some embodiments, the system includes adaptive optics (AO) to elongate the PSF (e.g., using a deformable mirror and a Shack-Hartmann wavefront sensor, as described in Jiang et al., *Opt Express.* 2010 Oct. 11; 18(21):21770-6, which is incorporated herein by reference).

In some cases, the system is configured to elongate the PSF by inducing spherical aberration in the optical path of the system. The system may be configured in any suitable way to induce the spherical aberration and elongate the PSF. In certain embodiments, one or more lenses used in the illumination path and/or the detection path is configured to induce a spherical aberration (e.g., a suitably configured refractive indices of the lenses, a suitably configured combination of concave and/or convex lenses, a suitably configured curvature of the lenses, etc.). In some cases, a medium with a refractive index that is different from (e.g., greater than or less than) the objective refractive index is positioned in between the sample and the detection objective to elongate the PSF, as described further herein. For example, a medium with a refractive index that is greater than the objective refractive index may be positioned between the sample and the detection objective to elongate the PSF.

In some embodiments, where a medium is positioned in between the sample and the detection objective to elongate the PSF, the medium may be composed of a suitable material and occupy a sufficiently dimensioned space between the sample and the objective so as to induce spherical aberration in the recorded image of the light pattern that is emitted from the sample when illuminated with a light sheet illumination of the present system, and passes through the medium before entering the detection objective. In other words, the material of the medium and the dimension of space in between the objective and the biological sample occupied by the medium may together be sufficient to elongate the point spread function (PSF) of the microscope preferentially in the z-axial direction, while maintaining a relatively constant lateral extent of the PSF (in the x-y plane), compared to a comparable microscope system in which the space between the objective and the biological sample is substantially occupied by a medium having a refractive index matching the objective refractive index.

The refractive index of the medium disposed between the detection objective and the sample may be 1.0 or greater, e.g., 1.1 or greater, 1.2 or greater, 1.3 or greater, 1.4 or greater, including 1.5 or greater, and may be 2.0 or less, e.g., 1.9 or less, 1.8 or less, 1.7 or less, 1.6 or less, including 1.5 or less. In some cases, the refractive index of the medium disposed between the detection objective and the sample is in the range of 1.0 to 2.0, e.g., 1.1 to 1.8, 1.2 to 1.7, 1.3 to 1.6, including 1.4 to 1.5. In certain embodiments, the refractive index of the medium disposed between the detection objective and the sample is in the range of 1.0 to 2.0. In certain embodiments, the refractive index of the medium disposed between the detection objective and the sample is in the range of 1.4 to 1.5.

The refractive index of the medium disposed between the detection objective and the sample may be different from the objective refractive index by a value of 0.1 or more, e.g., 0.2 or more, 0.3 or more, 0.4 or more, including 0.5 or more, and may be different by a value of 1.0 or less, 0.9 or less, 0.8 or less, 0.7 or less, 0.6 or less, including 0.5 or less. In some cases, the refractive index of the medium disposed between the detection objective and the sample may be different from the objective refractive index by a range of 0.1 to 1.0, e.g., 0.2 to 0.8, 0.2 to 0.6, including 0.3 to 0.5. The refractive index of the medium disposed between the detection objective and the sample may be greater than the objective refractive index by a value of 0.1 or more, e.g., 0.2 or more, 0.3 or more, 0.4 or more, including 0.5 or more, and may be different by a value of 1.0 or less, 0.9 or less, 0.8 or less, 0.7 or less, 0.6 or less, including 0.5 or less. In some cases, the refractive index of the medium disposed between the detection objective and the sample may be greater than the objective refractive index by a range of 0.1 to 1.0, e.g., 0.2 to 0.8, 0.2 to 0.6, including 0.3 to 0.5. The refractive index of the medium disposed between the detection objective and the sample may be less than the objective refractive index by a value of 0.1 or more, e.g., 0.2 or more, 0.3 or more, 0.4 or more, including 0.5 or more, and may be different by a value of 1.0 or less, 0.9 or less, 0.8 or less, 0.7 or less, 0.6 or less, including 0.5 or less. In some cases, the refractive index of the medium disposed between the detection objective and the sample may be less than the objective refractive index by a range of 0.1 to 1.0, e.g., 0.2 to 0.8, 0.2 to 0.6, including 0.3 to 0.5.

The medium may be any suitable medium having the desired refractive index for use in the present system. In some cases, the medium includes air, glass, water, glycerin, oil, or a combination thereof. In some cases, the medium includes a liquid material interposed between two layers of glass, e.g., between a side wall of a quartz cuvette sample holder and a quartz coverslip positioned adjacent the objective front lens. The oil may be any suitable oil, including synthetic and natural oils. Suitable synthetic oils include, but are not limited to, silicone oil, Moiwol®, as well as those provided by Cargille Laboratories, Inc. (NJ). Suitable natural oils include paraffin oil, Canada balsam and cedarwood oil. Other suitable medium materials include anisole, bromonaphthalene, and methylene iodide. In some cases, the medium includes a solid transparent material having a refractive index that is different (e.g., greater than or less than as described herein) from the objective refractive index. The solid transparent material may include any suitable material, including, but not limited to, quartz glass, plastic, sapphire or aluminum oxide. Any transparent plastic may be used including, but not limited to, acrylic, polyacrylic, polypropylene, polycarbonate, and silicone.

The thickness of the medium in between the objective and the biological sample may be of a sufficient thickness to induce spherical aberration in the recorded image of the light pattern emitted from the sample when illuminated with light sheet illumination. When referring to the medium between the objective and the biological sample, the term "thickness" refers to the dimension of the medium along the z-axial direction. The thickness of the medium in between the objective and the biological sample may be a sufficient thickness to elongate the PSF of the microscope in the z-axial direction. The thickness of the medium in between the objective and the biological sample may be 5 mm or more, e.g., 8 mm or more, 10 mm or more, 11 mm or more, including 15 mm or more, or 20 mm or more, or 25 mm or more, or 30 mm or more, or 40 mm or more, or 50 mm or more, and may be 100 mm or less, e.g., 90 mm or less, 80 mm or less, 70 mm or less, 60 mm or less, 50 mm or less, 40 mm or less, including 35 mm or less. In some embodiments, the thickness of the medium in between the objective and the biological sample is in the range of 5 mm to 100 mm, e.g., 8 mm to 80 mm, 10 mm to 60 mm, 10 mm to 40 mm, including 10 mm to 35 mm. The medium may span the space in between the objective and the sample for 50% or more, e.g., 75% or more, 80% or more, 85% or more, 90% or more, 95% or more, and up to about 100% of the total distance between the objective and the sample.

The distance between the objective and the biological sample may be referred to as the working distance (WD). The distance between the objective and the biological sample (working distance) may be a sufficient distance for use in the present system. When referring to the working distance between the objective and the biological sample, the working distance refers to the distance between the objective and the biological sample along the z-axial direction. The working distance may be 5 mm or more, e.g., 8 mm or more, 10 mm or more, 11 mm or more, including 15 mm or more, or 20 mm or more, or 25 mm or more, or 30 mm or more, or 40 mm or more, or 50 mm or more, and may be 100 mm or less, e.g., 90 mm or less, 80 mm or less, 70 mm or less, 60 mm or less, 50 mm or less, 40 mm or less, including 35 mm or less. In some embodiments, the distance between the objective and the biological sample (working distance) is in the range of 5 mm to 100 mm, e.g., 8 mm to 80 mm, 10 mm to 60 mm, 10 mm to 40 mm, including 10 mm to 35 mm. In certain embodiments, the distance between the objective and the biological sample (working distance) is 12 mm. In certain embodiments, the distance between the objective and the biological sample (working distance) is 16 mm. In certain embodiments, the distance between the objective and the biological sample (working distance) is 21 mm. In certain embodiments, the distance between the objective and the biological sample (working distance) is 29.5 mm.

The objective (e.g., detection objective) may be any suitable objective for use in the present system. The objective may be an air objective, oil objective, water objective, a water and air objective, and the like. In some cases, the objective is a custom designed objective or a commercially sold objective. In some instances, the objective is an air objective. In some cases, the objective has an objective refractive index of 1.0 or more, e.g., 1.1 or more, 1.2 or more, 1.3 or more, 1.4 or more, including 1.5 or more, and has an objective refractive index of 2.0 or less, 1.9 or less, 1.8 or less, 1.7 or less, 1.6 or less, 1.5 or less, 1.4 or less, 1.3 or less, including 1.2 or less. The objective may have an objective refractive index in the range of 1.0 to 2.0, e.g., 1.0 to 1.7, including 1.1 to 1.6.

The objective (e.g., detection objective) may have any suitable numerical aperture (NA) for use in the present system. In some cases, the objective has a numerical aperture of 0.01 or more, e.g., 0.05 or more, 0.1 or more, 0.2 or more, including 0.3 or more, and has a numerical aperture of 1.6 or less, e.g., 1.5 or less, 1.4 or less, 1.3 or less, 1.2 or less, 1.0 or less, 0.9 or less, 0.8 or less, 0.7 or less, 0.6 or less, including 0.5 or less. In some cases, the objective has a numerical aperture in the range of 0.01 to 1.6, e.g., 0.1 to 1.2, 0.1 to 0.8 0.1 to 0.6, including 0.1 to 0.5. In certain embodiments, the objective has a numerical aperture of 0.4. In certain embodiments, the objective has a numerical aperture of 0.3. In certain embodiments, the objective has a numerical aperture of 0.25. In certain embodiments, the objective has a numerical aperture of 0.28.

The light source may be any suitable light source. The light source may be a laser light source that emits a laser beam having a wavelength in the infrared range, near-infrared range, visible range, and/or ultra-violet range. The light source may be configured to produce a continuous wave, a quasi-continuous wave, or a pulsed wave light beam. In certain embodiments, a laser light source is a gas laser, solid state laser, a dye laser, semiconductor laser (e.g., a diode laser), or a fiber laser. In some instances, the light source is configured to generate a light sheet as described herein.

The present system may be configured in any suitable manner to generate a light sheet for imaging a biological sample. In some cases, the system is configured to direct a light beam from a light source and focus the light beam with a cylindrical lens to generate a light sheet. In some cases, the system is configured to rapidly scan a beam (for example using galvanometer scanners) to generate the light sheet. In some cases, the system includes an illumination objective that is configured to focus a light beam so that a slice of the sample is illuminated. In some cases, the system includes two or more illumination paths, such that two or more illumination objectives illuminate a slice of the sample and at the same z-axial position. In some cases, two or more illumination paths illuminate different slices of the sample at different z-axial positions.

The cross-sectional dimensions of the illuminated slice of the sample may be any suitable dimensions. In some cases, the light sheet illuminates in the sample a slice having an average thickness (i.e., length along the z-axis) of 1 µm or more, e.g., 2 µm or more, 3 µm or more, 4 µm or more, including 5 µm or more, and illuminates a slice having an average thickness of 20 µm or less, e.g., 15 µm or less, 10 µm or less, including 8 µm or less. The light sheet may illuminate a slice having an average thickness (i.e., length along the z-axis) in the range of 1 µm to 20 µm, e.g., 2 µm to 15 µm, 3 µm to 10 µm, including 4 µm to 8 µm.

The mirror galvanometer may be any suitable mirror galvanometer for use in the present system. Suitable mirror galvanometers include those used in scanning laser microscopes described in, e.g., U.S. Pat. No. 4,734,578; U.S. App. Pub. Nos. 2007/0171502, and 2011/0279893, the disclosures of each of which are incorporated herein by reference.

The image detector may be any suitable image detector for use in the present system. In some instances, the image detector is a digital camera, such as a CMOS camera, e.g., a sCMOS camera, or a charge-coupled device (CCD) camera, e.g., an electron-multiplying CCD (EMCCD) camera.

The present system may include one or more suitable controllers to control and/or coordinate the different components of the system. The present system may include non-optical components to store, process and/or analyze the images recorded by the optical components of the system. The non-optical components may include a computer, including a processor and a computer-readable medium containing instructions that, when executed by the processor, causes the controller to scan the biological sample and/or record a plurality of images, as described herein. The instructions contained in the computer-readable medium, when executed, may process and/or analyze the images captured by the image detector and/or stored in a memory location associated with the computer. The computer-readable medium may include any suitable instructions for the processor to control the controller, and/or process and/or analyze the images, e.g., according to an algorithm for performing a method of imaging a biological sample, as described herein. In some cases, the computer-readable medium includes instructions for deconvolving each image of the image stack based on a z-axial position of the planar section at which the image is recorded, and a predetermined, z axis-dependent point spread function corresponding to the planar section z-axial position. The predetermined, z axis-dependent point spread function may be an empirically determined z axis-dependent point spread function, or may be a z axis-dependent point spread function determined by modeling, or a combination of the two. The system may include a memory location associated with the computer, where the z axis-dependent point spread function may be stored in the memory location and may be accessible by the processor when deconvolving the images.

In some cases, the computer-readable medium includes instructions for the processor to segment the images to identify cells (in two dimensions or three dimensions), measure the level of fluorescence from a functional indicator as a function of time, and/or cluster the cells according to the pattern of activity measured.

Examples of storage media include CD-ROM, DVD-ROM, BD-ROM, a hard disk drive, a ROM or integrated circuit, a magneto-optical disk, a solid-state memory device, a computer readable flash memory, and the like, whether or not such devices are internal or external to the computer. A file containing information may be "stored" on computer readable medium, where "storing" means recording information such that it is accessible and retrievable at a later date by a computer (e.g., for offline processing). Examples of media include, but are not limited to, non-transitory media, e.g., physical media in which the programming is associated with, such as recorded onto, a physical structure. Non-transitory media for storing computer programming does not include electronic signals in transit via a wireless protocol.

In certain embodiments, the computer programming includes instructions for directing a computer to analyze the acquired image data qualitatively and/or quantitatively. Qualitative determination includes determinations in which a simple yes/no or present/not present result is provided to a user. Quantitative determination includes both semi-quantitative determinations in which a rough scale result, e.g., low, medium, high, is provided to a user and fine scale results in which an exact measurement is provided to a user.

With respect to computer readable media, "permanent memory" refers to memory that is not erased by termination of the electrical supply to a computer or processor. Computer hard-drive, CD-ROM, DVD-ROM, BD-ROM, and solid state memory are all examples of permanent memory. Random Access Memory (RAM) is an example of non-permanent memory. A file in permanent memory may be editable and re-writable. Similarly, a file in non-permanent memory may be editable and re-writable.

Methods

Method of Imaging a Biological Sample

Also provided herein is a method for imaging a biological sample. An implementation of the method may include: a) scanning a biological sample using one or more light sheets, where the biological sample is in a field of view of a microscope that includes an objective, where a direction of observation of the objective defines a z-axis and a point spread function of the microscope is elongated in the z-axial direction, thereby illuminating a plurality of z-axial slices of the biological sample, where the biological sample is at a z-axial distance from the objective; and b) recording a plurality of images corresponding to a plurality of z-axial slices of the sample, where the images are generated by light patterns emitted from the scanned biological sample, thereby generating an image stack comprising a plurality of images of the biological sample.

The PSF of the microscope used in the present method may be elongated using any suitable method for use with the light sheet illumination, as described above. In certain embodiments, the microscope PSF is elongated by using a medium having a refractive index different (e.g., greater than or less than) from the objective refractive index as described herein. In some cases, the PSF is elongated by inducing a spherical aberration in the images generated by the light microscope, e.g., by altering the refractive index of the medium in one or more portions of the microscope optical path away from the design specification of the microscope that normally minimizes spherical aberration.

As discussed above, the PSF may be elongated preferentially in the z-axial direction, while maintaining a relatively constant lateral extent of the PSF. In some embodiments, the ratio of the PSF full width at half-maximum (FWHM) in the z-axial direction of the microscope, when used in the present method, is elongated by 2 fold or more, e.g., 3 fold or more, 4 fold or more, 5 fold or more, 10 fold or more, 20 fold of more, 50 fold or more, including 100 fold or more, and is elongated by 1000 fold or less, e.g., 300 fold or less, 200 fold or less, 100 fold or less, 50 fold or less, 20 fold or less, 10 fold or less, 8 fold or less, including 5 fold or less, relative to the PSF FWHM in the z-axial direction of a comparable microscope that has a substantially diffraction-limited PSF in three dimensions. In some embodiments, the ratio of the PSF FWHM in the z-axial direction of the microscope, when used in the present method, is elongated by a range of 2 to 1000 fold, e.g., 3 to 300 fold, 4 to 100 fold, including 5 to 50 fold, relative to the PSF FWHM in the z-axial direction of a comparable microscope that has a substantially diffraction-limited PSF in three dimensions. The lateral spread (i.e., FWHM in the x-y plane) of the elongated PSF of the microscope, when used in the present method, may be less than 2 fold of the lateral spread of the PSF of a comparable microscope that has a substantially diffraction-limited PSF in three dimensions, along at least about 30% or more, e.g., about 40% or more, about 50% or more, about 60% or more, 70% or more, 80% or more, 90% or more, including 95% or more, or the z-axial length of the elongated PSF.

In some embodiments, the elongated PSF is characterized by an average PSF FWHM of a 1 μm fluorescent bead in the z-axial direction of 2 μm or more, e.g., 3 μm or more, 4 μm or more, 5 μm or more, 10 μm or more, 20 μm or more, 50 μm or more, 100 μm or more, 500 μm or more, including 1,000 μm or more, and an average PSF FWHM of a 1 μm fluorescent bead in the z-axial direction of 10,000 μm or less, e.g., 5,000 μm or less, 2,000 μm or less, 1,000 μm or less, 900 μm or less, 800 μm or less, 700 μm or less, 600 μm or less, including 500 μm or less. In some embodiments, the elongated PSF is characterized by an average PSF FWHM of a 1 μm fluorescent bead in the z-axial direction in the range of 2 μm to 10,000 μm, e.g., 3 μm to 5,000 μm, 4 μm to 2,000 μm, 5 μm to 1,000 μm, 10 μm to 900 μm, 50 μm to 800 μm, 100 μm to 700 μm, including 100 μm to 500 μm.

An implementation of the method of the present disclosure includes: a) scanning a biological sample using one or more light sheets, where the biological sample, or a portion thereof, is in a field of view of a microscope including an objective having an objective refractive index, where a direction of observation of the objective defines a z-axis and a medium is disposed between the sample and the objective, thereby illuminating a plurality of z-axial slices of the biological sample, each z-axial slice having an average slice thickness in the z-axial direction; and b) recording a plurality of images corresponding to the plurality of z-axial slices of the sample and generated by a plurality of light patterns emitted from the scanned biological sample, thereby generating an image stack including a plurality of images of the biological sample, or a portion thereof. As shown in FIG. 1A and FIG. 7A, a biological sample may be in front of a detection objective of the microscope, and the distance between the objective and the sample (e.g., the distance between the front lens of the objective and the sample; i.e., the working distance) may be kept at a constant value throughout the imaging process. The medium occupies a space between the objective and the sample, where the medium has a refractive index ($n_b$) greater than (as shown here, or alternatively, smaller than) the objective refractive index ($n_o$), and the combination of the refractive index difference and the thickness of the medium along the direction of observation (e.g., along the z-axis) is sufficient to induce a spherical aberration and/or elongate the PSF function of the microscope in the z-direction compared to a comparable microscope wherein light emitted from the sample travels through a medium having a refractive index matching the objective refractive index substantially along the distance between the objective and the biological sample. The biological sample may be scanned by one or more light sheets that illuminate slices, e.g., planar sections, within the sample that are substantially rectangular in cross section with a shorter vertical (e.g., z-axial) dimension than the lateral (e.g., x- or y-axial) dimension, and are aligned parallel to each other. By capturing the emitted light pattern from different slices, an image of the sample corresponding to the z-axial position of the light sheet that illuminated that slice can be generated.

The medium for use in the present method may have a refractive index that, in combination with the length of the medium through which light emitted from the sample travels to reach the objective, is sufficient to induce spherical aberration and/or elongate the point spread function of the microscope. The refractive index of the medium disposed between the detection objective and the sample may be 1.0 or greater, e.g., 1.1 or greater, 1.2 or greater, 1.3 or greater, 1.4 or greater, including 1.5 or greater, and may be 2.0 or less, e.g., 1.9 or less, 1.8 or less, 1.7 or less, 1.6 or less, including 1.5 or less. In some cases, the refractive index of the medium disposed between the detection objective and the sample is in the range of 1.0 to 2.0, e.g., 1.1 to 1.8, 1.2 to 1.7, 1.3 to 1.6, including 1.4 to 1.5. In certain embodiments, the refractive index of the medium disposed between the detection objective and the sample is in the range of 1.4 to 1.5.

The refractive index of the medium disposed between the detection objective and the sample may be different from the objective refractive index by a value of 0.1 or more, e.g., 0.2 or more, 0.3 or more, 0.4 or more, including 0.5 or more, and may be different by a value of 1.0 or less, 0.9 or less, 0.8 or less, 0.7 or less, 0.6 or less, including 0.5 or less. In some cases, the refractive index of the medium disposed between the detection objective and the sample may be different from the objective refractive index by a range of 0.1 to 1.0, e.g., 0.2 to 0.8, 0.2 to 0.6, including 0.3 to 0.5. The refractive index of the medium disposed between the detection objective and the sample may be greater than the objective refractive index by a value of 0.1 or more, e.g., 0.2 or more, 0.3 or more, 0.4 or more, including 0.5 or more, and may be different by a value of 1.0 or less, 0.9 or less, 0.8 or less, 0.7 or less, 0.6 or less, including 0.5 or less. In some cases, the refractive index of the medium disposed between the detection objective and the sample may be greater than the objective refractive index by a range of 0.1 to 1.0, e.g., 0.2 to 0.8, 0.2 to 0.6, including 0.3 to 0.5. The refractive index of the medium disposed between the detection objective and the sample may be less than the objective refractive index by a value of 0.1 or more, e.g., 0.2 or more, 0.3 or more, 0.4 or more, including 0.5 or more, and may be different by a value of 1.0 or less, 0.9 or less, 0.8 or less, 0.7 or less, 0.6 or less, including 0.5 or less. In some cases, the refractive index of the medium disposed between the detection objective and the sample may be less than the objective refractive index by a range of 0.1 to 1.0, e.g., 0.2 to 0.8, 0.2 to 0.6, including 0.3 to 0.5.

The medium may be any suitable medium for use in the present method. In some cases, the medium includes, without limitation, air, glass, water, glycerin, oil, or a combination thereof. In some cases, the medium includes a liquid material interposed between two layers of glass, e.g., between a side wall of a quartz cuvette sample holder and a quartz coverslip positioned adjacent the objective front lens. The oil may be any suitable oil, including synthetic and natural oils. Suitable synthetic oils include, but are not limited to, silicone oil, Moiwol®, as well as those provided by Cargille Laboratories, Inc. (NJ). Suitable natural oils include, but are not limited to, paraffin oil, Canada balsam and cedarwood oil. Other suitable medium materials include, without limitation, anisole, bromonaphthalene, and methylene iodide. In some cases, the medium includes a solid transparent material having a refractive index that is different from the objective refractive index. The solid transparent material may include any suitable material, including, but not limited to, quartz glass, plastic, sapphire or aluminum oxide. Any transparent plastic may be used including, but not limited to, acrylic, polyacrylic, polypropylene, polycarbonate, and silicone.

The thickness of the medium in between the objective and the biological sample may be of a sufficient thickness to induce spherical aberration in the recorded image of the light pattern emitted from the sample when illuminated with a light sheet illumination. When referring to the medium between the objective and the biological sample, the term "thickness" refers to the dimension of the medium along the z-axial direction. The thickness of the medium in between the objective and the biological sample may be a sufficient thickness to elongate the PSF of the microscope in the z-axial direction. The thickness of the medium in between the objective and the biological sample may be 5 mm or more, e.g., 8 mm or more, 10 mm or more, 11 mm or more, including 15 mm or more, or 20 mm or more, or 25 mm or more, or 30 mm or more, or 40 mm or more, or 50 mm or more, and may be 100 mm or less, e.g., 90 mm or less, 80 mm or less, 70 mm or less, 60 mm or less, 50 mm or less, 40 mm or less, including 35 mm or less. In some embodiments, the thickness of the medium in between the objective and the biological sample is in the range of 5 mm to 100 mm, e.g., 8 mm to 80 mm, 10 mm to 60 mm, 10 mm to 40 mm, including 10 mm to 35 mm. The medium may span the space in between the objective and the sample for at least 10%, e.g., 25% or more, 50% or more, 75% or more, 80% or more, 85% or more, 90% or more, 95% or more, and up to about 100% of the total distance between the objective and the sample.

The distance between the objective and the biological sample may be referred to as the working distance (WD). The distance between the objective and the biological sample (working distance) may be a sufficient distance for use in the present system. When referring to the working distance between the objective and the biological sample, the working distance refers to the distance between the objective and the biological sample along the z-axial direction. The working distance may be 5 mm or more, e.g., 8 mm or more, 10 mm or more, 11 mm or more, including 15 mm or more, or 20 mm or more, or 25 mm or more, or 30 mm or more, or 40 mm or more, or 50 mm or more, and may be 100 mm or less, e.g., 90 mm or less, 80 mm or less, 70 mm or less, 60 mm or less, 50 mm or less, 40 mm or less, including 35 mm or less. In some embodiments, the distance between the objective and the biological sample (working distance) is in the range of 5 mm to 100 mm, e.g., 8 mm to 80 mm, 10 mm to 60 mm, 10 mm to 40 mm, including 10 mm to 35 mm. In certain embodiments, the distance between the objective and the biological sample (working distance) is 12 mm. In certain embodiments, the distance between the objective and the biological sample (working distance) is 16 mm. In certain embodiments, the distance between the objective and the biological sample (working distance) is 21 mm. In certain embodiments, the distance between the objective and the biological sample (working distance) is 29.5 mm.

The objective (e.g., detection objective) may be any suitable objective for use in the present method. The objective may be an air objective, oil objective, water objective, a water and air objective, etc. In some cases, the objective is a custom designed objective or a commercially sold objective. In some instances, the objective is an air objective. The objective (e.g., detection objective) may have any suitable numerical aperture (NA) for use in the present method. In some cases, the objective has a numerical aperture of 0.01 or more, e.g., 0.05 or more, 0.1 or more, 0.2 or more, including 0.3 or more, and has a numerical aperture of 1.6 or less, e.g., 1.5 or less, 1.4 or less, 1.3 or less, 1.2 or less, 1.1 or less, 1.0 or less, 0.9 or less, 0.8 or less, 0.7 or less, 0.6 or less, including 0.5 or less. In some cases, the objective has a numerical aperture in the range of 0.01 to 1.6, e.g., 0.1 to 1.2, 0.1 to 0.8 0.1 to 0.6, including 0.1 to 0.5.

Scanning the sample with light sheet may include moving a light sheet along a dimension across the sample. Moving the light sheet may be carried out in any suitable manner for the present method. In some cases, the scanning includes using one or more mirror galvanometers to translate a light sheet along the z-axial direction. The mirror galvanometer may be any suitable mirror galvanometer, as described above. The scanning speed is sufficient to allow for the image detector to obtain an image of the slice at any given z-axial position, and to allow for recording multiple z-axial slices of the sample in a short time period. The scanning may be step-wise, or may be substantially continuous in the z-direction.

The recording of the image of the illuminated slice in the sample may include recording multiple images, each image corresponding to a slice at specific z-axial position along the sample, using a suitable image detector. The image detector may be any suitable image detector, as described above. Thus, the image detector may be exposed to a light pattern emitted from a sample illuminated with a light sheet at a specific z-axial position for sufficient amount of time to obtain an image of the z-axial slice of the sample. The exposure time per z-axial position may vary. In some cases, the exposure time per z-axial position is 0.1 ms or more, e.g., 0.5 ms or more, 1 ms or more, 2 ms or more, 3 ms or more, including 5 ms or more, and is 100 ms or less, e.g., 50 ms or less, 20 ms or less, 15 ms or less, 10 ms or less, including 8 ms or less. In some embodiments, the exposure time per z-axial position is in the range of 0.1 ms to 100 ms, e.g., 0.5 ms to 50 ms, 1 ms to 20 ms, including 1 ms to 10 ms.

In some cases, light sheets emitted by multiple sources illuminate a slice of the sample at the same z-axial position in the sample at a given time point. The biological sample may be illuminated simultaneously at a given z-axial position using any suitable configuration of light sheets (e.g., any suitable number of light sheet sources, orientation of the light sheet sources, etc.). In some cases, the sample is illuminated by one or more, e.g., two or more, light sheets simultaneously at a given z-axial position. Where there is more than one light sheet illuminating the sample simultaneously at a given z-axial position, the light sheets may be positioned relative to each other and the sample in any suitable manner. In some cases, two light sheets are projected onto the sample at a given z-axial position simultaneously from opposite sides of the biological sample (see, e.g., FIG. 7B).

Alternatively, multiple light sheets illuminating different slices in the sample at different z-axial positions may be projected simultaneously, in as much as the point spread functions (i.e., 2-dimensional PSFs in the x-y plane) at the corresponding z-axial positions are not substantially different from each other.

The light sheet used to scan the sample illuminates a slice of the sample having a rectangular cross-section, as described above. The cross-sectional thickness of the illuminated slice may be any suitable dimensions for obtaining a desired depth resolution. In some cases, the light sheet illuminates in the sample a slice having an average thickness (i.e., length along the z-axis) of 1 µm or more, e.g., 2 µm or more, 3 µm or more, 4 µm or more, including 5 µm or more, and illuminates a slice having a thickness of 20 µm or less, e.g., 15 µm or less 10 µm or less, including 8 µm or less. The light sheet may illuminate a slice having an average thickness (i.e., length along the z-axis) in the range of 1 µm to 20 µm, e.g., 2 µm to 15 µm, 3 µm to 10 µm, including 4 µm to 8 µm.

Each pair of adjacent slices of the z-axial slices of the biological sample imaged by the present method may be offset from each other by a distance along the z-axis, e.g., as measured between the z-axial position of the center of a first slice to the z-axial position of the center of a second slice adjacent the first slice, to generate a three-dimensional image of the sample. Adjacent slices of the z-axial slices may be offset by any suitable distance. In some cases, the z-axial slices are offset by a distance of 0.5 µm or more, e.g., 1 µm or more, 2 µm or more, 5 µm or more, 10 µm or more, 50 µm or more, including 100 µm or more, and offset by a distance of 500 µm or less, e.g., 200 µm or less, 100 µm or less, 50 µm or less, 10 µm or less, 7 µm or less, including 5 µm or less. In certain embodiments, the z-axial slices are offset by a distance in the range of 0.5 µm to 500 µm, e.g., 1 µm to 100 µm, 2 µm to 50 µm, including 2 µm to 10 µm.

Figure 11:
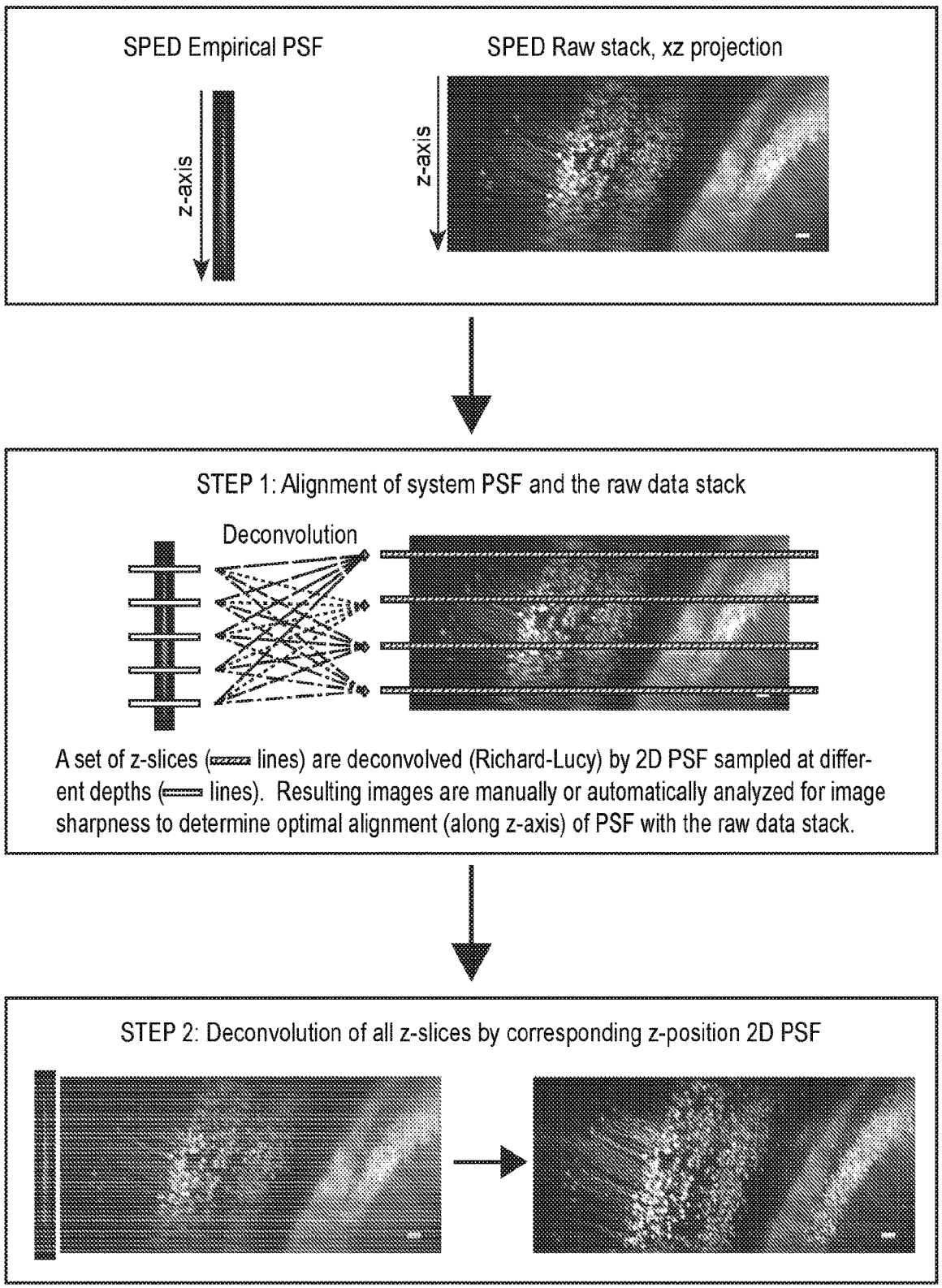
FIG. 11 is a collection of images and schematic diagrams depicting the SPED light sheet data deconvolution pipeline, according to embodiments of the present disclosure.

In some embodiments, the present method includes deconvolving the z-axial slice images of the biological sample to improve the quality of the images. An implementation of the deconvolving may involve, for each image recorded, using the z-axial position of the image and deconvolving the image with a predetermined, z axis-dependent point spread function corresponding to the z-axial position of the image. In some embodiments, the method may include registering the image stack with the predetermined, z axis-dependent point spread function, to identify the optimal two-dimensional PSF for the particular z-axial position of the image, for example as depicted in FIG. 11. The registering may involve selecting one or more images from the image stack, and for each selected image, deconvolving the selected image using a number of two-dimensional PSFs of the predetermined, z axis-dependent PSF at different z-axial depths. Then, the optimal z-axial position of the two-dimensional PSF for the selected image is chosen based on manual inspection and/or automatic evaluation of the deconvolved images for sharpness. Once the image stack is registered with the predetermined, z axis-dependent PSF, any remaining images of the image stack may be deconvolved based on the z-axial position of each image and the corresponding two-dimensional PSF of the predetermined, z axis-dependent PSF.

The predetermined, z axis-dependent PSF may be obtained using any suitable method. In some cases, the z axis-dependent PSF is known for the particular system used to carry out the method. In some cases, the z axis-dependent PSF is obtained empirically. A z axis-dependent PSF may be obtained empirically by imaging a point source of light (e.g., a fluorescent bead) illuminated by a light sheet, and obtaining images of the point source of light as the point source and the light sheet are translated along the direction of observation (e.g., z-direction) of the microscope.

The deconvolution may be performed using any suitable algorithm. In some cases, the deconvolution algorithm includes, without limitation, the Richardson-Lucy deconvolution, Wiener deconvolution, and the like.

The present method may include analyzing the images and/or image stack for further characterizing the biological sample. The analyzing may include any suitable processes and/or the use of any suitable algorithms on the images. In some cases, the analyzing includes registering, morphing, warping, aligning, counting and/or quantifying one or more properties associated with the one or more images. In some embodiments, the method includes segmenting the image stack, e.g., to identify and mark individual cells in the 3D image. The segmented image may then be used to track a feature of multiple cells in the imaged volume over time. In some cases, the segmented volumetric images may be tracked over time to measure the electrical activity of cells, e.g., neurons, over time. In some cases, the tracked cells may be clustered using a suitable clustering algorithm to group the cells by their activity pattern, thereby obtaining a global activity pattern of cells, e.g., neurons, in an imaged volume, e.g., a brain or portion thereof, over time.

In some embodiments, the biological sample imaged using the present method is a clarified biological sample. Thus, the present method may include, before scanning the biological sample, clarifying the biological sample; and positioning the clarified biological sample in the field of view of the microscope. The biological sample may be clarified using any suitable method. Suitable clarifying methods include, without limitation, CLARITY™; passive clarity technique (PACT); perfusion-assisted agent release in situ (PARS); SeeDB; ClearT; 3-dimensional imaging of solvent-cleared organs (3DISCO); immunolabeling-enabled 3-dimensional imaging of solvent-cleared organs (iDISCO); clear, unobstructed brain imaging cocktails and computational analysis (CUBIC); Scale and derivative methods thereof, hydrogel embedding, delipidation, or refractive index matching. Methods for clarifying a biological sample are described in, e.g., Chung, Kwanghun, and Karl Deisseroth. "CLARITY for mapping the nervous system." *Nature Methods,* 10.6 (2013): 508-513; Tomer, Raju, et al. "Advanced CLARITY for rapid and high-resolution imaging of intact tissues." *Nature Protocols,* 9.7 (2014): 1682-1697; Ertürk, Ali, and Frank Bradke. "High-resolution imaging of entire organs by 3-dimensional imaging of solvent cleared organs (3DISCO)." *Experimental Neurology,* 242 (2013): 57-64; Renier, Nicolas, et al. "iDISCO: a simple, rapid method to immunolabel large tissue samples for volume imaging." *Cell,* 159.4 (2014): 896-910; Tainaka, Kazuki, et al. "Whole-body imaging with single-cell resolution by tissue decolorization." *Cell,* 159.4 (2014): 911-924; the disclosures of each of which are incorporated herein by reference.

In some cases, the method further includes performing the scanning and recording on a plurality of fields of view of the microscope. In such cases, the method may include translating the sample along the x-y dimension so as to allow scanning and recording at multiple fields of view of the microscope. In some cases, the different fields of view may be positioned so as to generate images that are tiled across the biological sample x-y plane to cover a contiguous surface of the sample larger than the field of view of the microscope. In some cases, the tiled images are overlapping, and in other cases the tiled images are non-overlapping. The image stacks generated at different fields of view may be combined during analysis.

The present method may be implemented on any suitable light-sheet microscopy system, including the system described herein.

The present method can be a method of obtaining a volumetric image (i.e., a three-dimensional image) of a biological sample. Thus, the image stack generated by the present method may include a three-dimensional representation of a contiguous volume of the biological sample, where the imaged volume has a z-axial thickness that is greater than the z-axial thickness of a slice of the sample illuminated by a light sheet. In some cases, the volume imaged by the method has a thickness (i.e., length in the z-direction of observation) of 10 µm or more, e.g., 20 µm or more, 50 µm or more, 75 µm or more, 100 µm or more, 500 µm or more, 1,000 µm or more, such as 10.0 mm or more, including 100.0 mm or more and has a thickness of 100.0 mm or less, e.g., 10.0 mm or less, 5.0 mm or less, 1.0 mm or less, 0.5 mm or less, 0.3 mm or less, including 0.1 mm or less. In some cases, the volume imaged by the method has a thickness (i.e., length in the z-direction of observation) in the range of 10 µm to 100.0 mm, e.g., 20 µm to 10.0 mm, 75 µm to 5.0 mm, 0.1 mm to 1.0 mm, including 0.1 mm to 0.5 mm. The lateral dimension (i.e. length in the x- or y-directions horizontal to the direction of observation) of the volumetric image may be any suitable length. In some cases, the volumetric image has a lateral dimension in the range of 50 µm to 100.0 mm, e.g., 0.1 mm to 50.0 mm, including 0.1 mm to 10.0 mm.

The present method can be a rapid method of obtaining a volumetric image (i.e., a three-dimensional image) of a biological sample. In some cases, the method images a volume of the biological sample at a rate of 1 volume/sec or more, e.g., 2 volumes/sec or more, 4 volumes/sec or more, 7 volumes/sec or more, 10 volumes/sec or more, 12 volumes/sec or more, 20 volumes/sec or more, 50 volumes/sec or more, 100 volumes/sec or more, including 1,000 volumes/sec or more, and images a volume of the biological sample at a rate of 5,000 volumes/sec or less, e.g., 1,000 volumes/sec or less, 100 volumes/sec or less, 50 volumes/sec or less, 25 volumes/sec or less, 15 volumes/sec or less, including 10 volumes/sec or less. In certain embodiments, the method images a volume of the biological sample at a rate in the range of 1 to 5,000 volumes/sec, e.g., 2 volumes/sec to 1,000 volumes/sec, 2 volumes/sec to 100 volumes/sec, 4 volumes/sec to 50 volumes/sec, including 4 volumes/sec to 15 volumes/sec.

The present method can be a high-resolution method of obtaining a volumetric image (i.e., a three-dimensional image) of a biological sample, where the present method achieves single-cell resolution in the z-axial and lateral (x- and y-axial) directions.

Method of Diagnosing a Tissue Sample

Also provided herein is a method of diagnosing a tissue sample using an imaging method of the present disclosure. An implementation of the method of diagnosing the tissue sample may include obtaining a tissue sample from an individual, imaging the tissue sample according to a method of imaging a biological sample as described herein, thereby generating an image stack containing a plurality of images of the tissue sample, or a portion thereof, and analyzing, qualitatively or quantitatively, one or more images of the image stack for one or more features diagnostic of pathology, thereby diagnosing the tissue sample. Qualitative analysis may include determining the presence or absence of a diagnostic feature of a pathology. Quantitative analysis may include any number of ways to measure the diagnostic feature of a pathology, as appropriate. In some cases, the analysis includes determining a surgical margin based on the images of the tissue sample.

The pathology that can be diagnosed by the present method may include any suitable pathological state of the tissue. In some cases, the pathology is a malignancy or cancerous tissue. In some cases, the pathology is infiltration of immune cells characteristic of a pathological condition. In some cases, the pathology is tissue rejection of a transplanted tissue. In some cases, the pathology is inflammation of the tissue.

In some cases, the diagnostic feature of a pathology is indicated by the presence of diagnostic molecular markers in the tissue. Any suitable diagnostic molecular marker may be used to diagnose the tissue. In some cases, the diagnostic molecular marker is a diagnostic nucleic acid, diagnostic antigen, diagnostic peptide, diagnostic metabolite, etc. These diagnostic molecular markers may be detected using any suitable detection method (e.g., antibody staining, in situ hybridization, etc.).

The present diagnostic method may also include using other imaging techniques to image and characterize the tissue of interest. Any suitable imaging technique may be used. Suitable imaging techniques may include, but are not limited to, confocal microscopy, two-photon microscopy, light-field microscopy, tissue expansion microscopy, and/or CLARITY™-optimized light sheet microscopy (COLM), etc.

The present diagnostic method can be a rapid method of diagnosing a tissue of interest, such as a biopsy tissue. In some cases, the method may allow diagnosis of a tissue, from obtaining the tissue to identifying a pathological condition associated with the tissue, in an hour or less, e.g., 45 minutes or less, including 30 minutes or less. In some cases, the tissue may be a biopsy tissue obtained during surgery, where a medical decision related to the surgery is rendered based on the diagnosis of the biopsy tissue obtained by the carrying out the present method.

Biological Sample

The present methods and systems may be used to image a variety of biological samples. The biological sample may be a multicellular organism or a portion thereof, such a tissue, e.g., animal tissue, or organ. The tissue or organs may be whole or part of a brain, eye, heart, liver, pancreas, muscle, bone, kidney, prostate, breast, cervix, lung, and/or ovary. The biological sample may be a healthy sample, e.g., a healthy tissue from a healthy individual, or may be a pathological sample, e.g., a pathological tissue from an individual suspected of having or known to have a disease. The disease may be any suitable disease, including, but not limited to, cancer, inflammation, diabetes, etc. The biological sample may be a live sample, a processed sample (e.g., a clarified sample, as described above; a labeled sample, etc.), or a fixed sample. In some cases, the biological sample is an animal, such as a living animal. In some cases, the biological sample is a genetically modified sample (e.g., a genetically modified organism or tissue).

In some embodiments, the biological sample is labeled or stained with a detectable label. In some cases, the biological sample contains one or more cells that are associated with a detectable label, e.g., a fluorescent label, colorimetric label, etc. A fluorescent label may be a fluorescent dye or a fluorescent protein that enables the cells to emit fluorescence in response to an appropriate light sheet illumination (e.g., light sheet illumination having the appropriate wavelength and intensity of illumination). In some embodiments, the cells of the biological sample, e.g., neurons, include a fluorescent moiety, e.g., a fluorescent dye or a fluorescent protein, that enables the cells to emit fluorescence in response to an appropriate light sheet illumination. The cells of the biological sample may be made to associate with the fluorescent moiety by any suitable method, including being labeled directly or indirectly with a fluorescent dye or fluorescent protein, or expressing a genetically encoded fluorescent protein. Any suitable method may be used to indirectly label cells of the biological sample with a fluorescent moiety. In some cases, a binding member, e.g., an antibody, that specifically binds to a cellular component, e.g., a cell surface marker on the cells, may be conjugated with a detectable label, e.g., a fluorescent dye or protein, and the labeled binding member may be used to label the cells indirectly. In some cases, the binding member is a nucleic acid that includes a sequence that hybridizes with a target sequence in cells of the biological sample, and the nucleic acid may be conjugated to a detectable label.

The biological sample may be labeled with a detectable label at any suitable density. In some cases, substantially all cells of the sample are labeled with a detectable label. In some cases, substantially all cells of a cell type (e.g., substantially all neurons) are labeled with a detectable label. In some cases, where a detectable label is encoded genetically and expressed by cells of the biological sample, the detectable label is expressed under a promoter that drives expression in specific subsets of cells in the biological sample. In some cases, the promoter is a tissue-specific promoter. In some cases, the promoter is specific for cell types within a tissue.

Fluorescent dyes of interest include, but are not limited to, fluorescein, fluorescein isothiocyanate (FITC), rhodamine, tetramethylenerhodamine isothiocyanate (TRITC), sulforhodamine 101 acid chloride (Texas Red®), phycoerythrin (PE), allophycocyanin, phycoerythrin-Texas Red® (PETR), 4-methylumbelliferone, etc. Fluorescent proteins of interest, which may be genetically encoded, include green fluorescent protein, yellow fluorescent protein, cyan fluorescent protein, etc., and variants thereof.

In certain embodiments, the detectable label is a small molecule dye such as DAPI (4',6-diamidino-2-phenylindole), acridine orange, hydroethidine, etc. Other detectable labels may include Acid Fuchsin, Acridine Orange, Alcian Blue 8GX, Alizarin, Alizarin Red S, Alizarin Yellow R, Amaranth, Amido Black 10B, Aniline Blue Water Soluble, Auramine O, Azure A, Azure B, Basic Fuchsin Reagent A.C.S., Basic Fuchsin Hydrochloride, Benzo Fast Pink 2BL, Benzopurpurin 4B, Biebrich Scarlet Water Soluble, Bismarck Brown Y, Brilliant Green, Brilliant Yellow, Carmine, Lacmoid, Light Green SF Yellowish, Malachite Green Oxalate, Metanil Yellow, Methylene Blue, Methylene Blue Chloride, Methylene Green, Methyl Green, Methyl Green Zinc Chloride Salt, Methyl Orange Reagent A.C.S., Methyl Violet 2B, Morin, Naphthol Green B, Neutral Red, New Fuchsin, New Methylene Blue N, Nigrosin Water Soluble, Nigrosin B Alcohol Soluble, Nile Blue A, Nuclear Fast Red, Oil Red O, Orange II, Orange IV, Orange G, Patent Blue, 4-(Phenylazo)-1-naphthalenamine Hydrochloride, Phloxine B, Ponceau G R 2R, Ponceau 3R, Ponceau S, Procion Blue HB, Prussian Blue, Pyronin B, Pyronin Y, Quinoline Yellow SS, Rhodamine 6G, Rhodamine B Base Alcohol Soluble, Rhodamine B O, p-Rosaniline Acetate Powder, Rose Bengal, Rosolic Acid, Saffron, Safranine O, Stilbene Yellow, Sudan I, Sudan II, Sudan III, Sudan IV, Sudan Black B, Sudan Orange G, Tartrazine, Thioflavine T TG, Thionin, Toluidine Blue O, Tropaeolin O, Trypan Blue, Ultramarine Blue, Victoria Blue B, Victoria Blue R, Xylene Cyanol FF, Xylene Cyanol FF, Alizarin, Alizarin red S (sodium monosulfonate) monohydrate, Alum carmine, Amaranth, Arsenazo III, Basic red 2 (Cotton red; Gossypimine; Safranin A or O or Y), Bismark brown, Bromocresol green, Bromocresol purple, Bromophenol blue, Bromophenol red, Bromothymol blue, Calcein, Calcon (Eriochrome black B), Clayton yellow (Thiazole yellow), Coomassie blue (Brilliant blue), Cotton Red (Basic red 2; Gossypimine; Safranin A or O or Y), Cresol red sodium salt, Cupferron, 2',7'-Dichloro fluorescein, Dicyanobis (1,10-phenanthroline)Iron, Diethyldithiocarbamic acid silver salt, 4,7-Diphenyl-1,10-phenanthroline-x.x-disulfonic acid diNa salt, Diphenylthiocarbazone, Dithizone, Eosin bluish, Eosin Y, Eriochrome black B (Calcon), Eriochrome black T, Eriochrome blue, Eriochrome blue black R, Eriochrome blue SE, Eriochrome gray SGL, Eriochrome red B, Erionglaucine (A), Erythrosin B, Fast Green FCF, Fuchsin acid, Fuchsin basic (Pararosaniline HCl), Gentian Violet, Gossypimine (Basic red 2; Cotton red; Safranin A or O or Y), Hematoxylin, Hydroxy Naphthol blue, Indigo blue pigment, Janus green B, Methyl orange, Methyl orange, Methyl red, Methyl thymol blue, Methyl violet B (Aniline violet; Dahlia violet B), Methyl violet base (Solvent violet 8), Methylene blue, Murexide indicator, Neutral red, Orange G, Orange IV, Owen's blue, Patent blue (Acid blue 1), Pararosaniline HCl (Basic fuchsin), Phenolphthalein, Phenol red, Phlorglucinol dihydrate, Pyronine Y (or G), Safranin, Safranin A or O or Y (Basic red 2; Cotton red; Gossypimine), Solvent violet 8 (Methyl violet base), Sudan III, Sudan IV, Thiazole yellow (Clayton yellow), Thymol blue, Thymolphthalein pH indicator 9.4-10.6, Wright's stain, Xylene cyanole FF, Chromotrope 2B, Chromotrop 2R, Clayton Yellow; Cochineal Red A, Congo Red, Coomassie® Brilliant Blue G-250, Coomassie® Brilliant Blue R-250, Cotton Blue, Crocein Scarlet 3B, Curcumin, Diazo Blue B, Eosin B, Eosin B Water Soluble, Eosin Y, Eriochrome Black A, Eriochrome Black T Reagent A.C.S., Eriochrome Blue Black R, Eriochrome Cyanine R, Erioglaucine, Erythrosin B, Ethyl Eosin, Ethyl Violet, Evans Blue, Fast Garnet GBC Base, Fast Garnet GBC Salt, Fast Green FCF, Fluorescein Alcohol Soluble U.S.P., Fluorescein Alcohol Soluble, Fluorescein Water Soluble, Hematoxylin, 8-Hydroxy-136-pyrenetrisulfonic Acid Trisodium Salt; Indigo Synthetic, Indigo Carmine, Indophenol Blue, Indulin Water Soluble, and Janus Green B. In other embodiments, the detectable label may include labeled or unlabeled antibodies specific for a particular protein or antigen such p53, p38, p43, fos, c-fos, jun, NF-κB, anillin, SC35, CREB, STET3, SAMD, FKHD, D4G, calmodulin, calcineurin, actin, microtubulin, ribosomal proteins, receptors, cell surface antigens such as CD4, etc.

In some cases, the biological sample contains cells that contain an indicator dye, such as a functional indicator dye. The indicator dye may be a genetically encoded indicator dye. The genetically encoded indicator may be configured to be expressed in specific subsets of cells in the biological sample using specific promoters to drive expression of the indicator dye, as described above. The indicator dye may be adapted to emit fluorescence in response to cellular electrical activity, e.g., neuronal activity, muscle contraction, etc. Fluorescent moieties whose fluorescence properties are sensitive to cellular electrical activity include genetically encoded ratiometric/non-ratiometric dyes and fluorescent proteins. Fluorescent moieties whose fluorescence properties are sensitive to cellular electrical activity may be a fluorescence resonance energy transfer (FRET)-based reporter. Fluorescent moieties whose fluorescence properties are sensitive to cellular electrical activity may be sensitive to changes in intracellular concentration of ions such as calcium, sodium and protons or to changes in membrane potential. In such cases, fluorescent dyes of interest include, but are not limited to, calcium indicator dyes (Indo-1, Fura-2, and Fluo-3, Calcium Green®, Fluo-4, etc.); sodium indicator dyes (sodium-binding benzofuran isophthalate (SBFI), Sodium Green™, CoroNa™ Green, CoroNa™ Red, etc.); and proton indicator dyes (2',7'-bis-(carboxyethyl)-5-(and-6)-carboxyfluorescein (BCECF), etc.). Cellular electrical activity-sensitive fluorescent proteins of interest include, but are not limited to, calcium indicators (Cameleon, GCaMP1, GCaMP2, GCaMP3, GCaMP6 and derivatives thereof, as well as those cited in U.S. Pat. No. 8,629,256, and Tian et al. 2012 Prog Brain Res., 196:79, the disclosures of each of which are incorporated herein by reference); and voltage indicators (QuasAr1, QuasAr2, VSFP, and derivatives thereof, as well as those cited in U.S. App. Pub. No. 2013/0224756, Hochbaum et al., Nat Methods, 2014, 11:825, Baker et al. Brain Cell Biol., 2008, 36:53; and Mutoh et al., Exp Physiol., 2011, 96:13, the disclosures of each of which are incorporated herein by reference). In some cases, the fluorescent moiety may be sensitive to biochemical changes in the excitable cell, such as changes in enzymatic activity (e.g., activation of kinases); changes in binding interactions (e.g., binding of transcription factors to DNA); changes in subcellular localization of proteins; etc. Exemplary fluorescent moieties are further described in, e.g. Mehta et al., Annu Rev Biochem., 2011; 80: 375, the disclosure of which is incorporated herein by reference.

In some embodiments, the biological sample contains cells that are adapted to hyperpolarize and/or depolarize in response to an extrinsic stimulus, e.g., a laser light stimulus applied to the sample. In some embodiments, the biological sample may contain a photo-sensitive caged compound, e.g., a caged neurotransmitter, that, when uncaged by a light stimulus, binds to a receptor on an excitable cell nearby and contributes to hyperpolarizing or depolarizing the excitable cell, depending on the neurotransmitter and the receptor. In some cases, the caged neurotransmitter may be glutamate, dopamine, serotonin, GABA, etc., available from, e.g., Tocris, as well as those caged neurotransmitters described in, e.g., U.S. Pat. No. 8,178,496, the disclosure of which is incorporated herein by reference. Suitable methods of using caged neurotransmitters to stimulate neurons is described in, e.g., Noguchi et al., J Physiol., 2011, 589:2447, the disclosure of which is incorporated herein by reference.

In some embodiments, the biological sample contains cells that are genetically modified to express a light-responsive polypeptide that, when stimulated by an appropriate light stimulus, hyperpolarizes or depolarizes the cell, e.g., excitable cell, such as a neuron or muscle cell. In some instances, the light-responsive polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the cell when activated by light of an activating wavelength. In some embodiments, the light-responsive polypeptide hyperpolarizes the cell when activated by light of an activating wavelength. Suitable hyperpolarizing and depolarizing polypeptides are known in the art and include, e.g., a channelrhodopsin (e.g., ChR2), variants of ChR2 (e.g., C128S, D156A, C128S+D156A, E123A, E123T), iC1C2, C1C2, GtACR2, NpHR, eNpHR3.0, C1V1, VChR1, VChR2, SwiChR, Arch, ArchT, KR2, ReaChR, ChiEF, Chronos, ChRGR, and the like. Hyperpolarizing and depolarizing opsins have been described in various publications; see, e.g., Berndt and Deisseroth (2015) Science, 349:590; Berndt et al. (2014) Science, 344:420; and Guru et al. (Jul. 25, 2015) Intl. J. Neuropsychopharmacol., pp. 1-8 (PMID 26209858).

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Materials and Methods

The following materials and methods were used in the Examples.

SPherical Aberration-Assisted Extended Depth-of-Field (SPED) Light Sheet Implementation A SPED light sheet (LS) microscopy system was built on a CLARITY™-Optimized Light-sheet Microscope (COLM) device. Briefly, two light-sheets were generated from two opposite illumination arms that included a laser source, filter wheel, shutter, x-y galvanometer scanner, scan lens, tube lens, mirror and an illumination objective (Olympus Macro 4x/0.28 NA). The emitted signal was detected with an orthogonally arranged wide-field detection arm, including a detection objective, emission filter wheel, tube lens and scientific complementary metal oxide semiconductor (sC-MOS) camera (Hamamatsu Orca Flash 4.0 V2). Refractive index (RI) blocks to induce spherical aberration-based axial point spread function (PSF) elongation (SPED) were implemented by filling the sample chamber (FIGS. 7A and 7B) with specific refractive index liquids (1.454 was used for the most of the experiments described herein). The RI block thickness was specified using variable lengths of lens tubes (Thorlabs, 2" diameter) in the sample chamber (FIGS. 7A and 7B). This was equivalent to using solid transparent material of varying thickness. Samples were mounted in custom thin-walled (0.5 mm thick) quartz glass cuvettes (Starna Cells). The imaging procedures for rapid light-sheet scanning (while keeping all the other parts stationary) and time lapse experiments data logging were implemented using COLM software and electronics control framework.

Figure 7A:
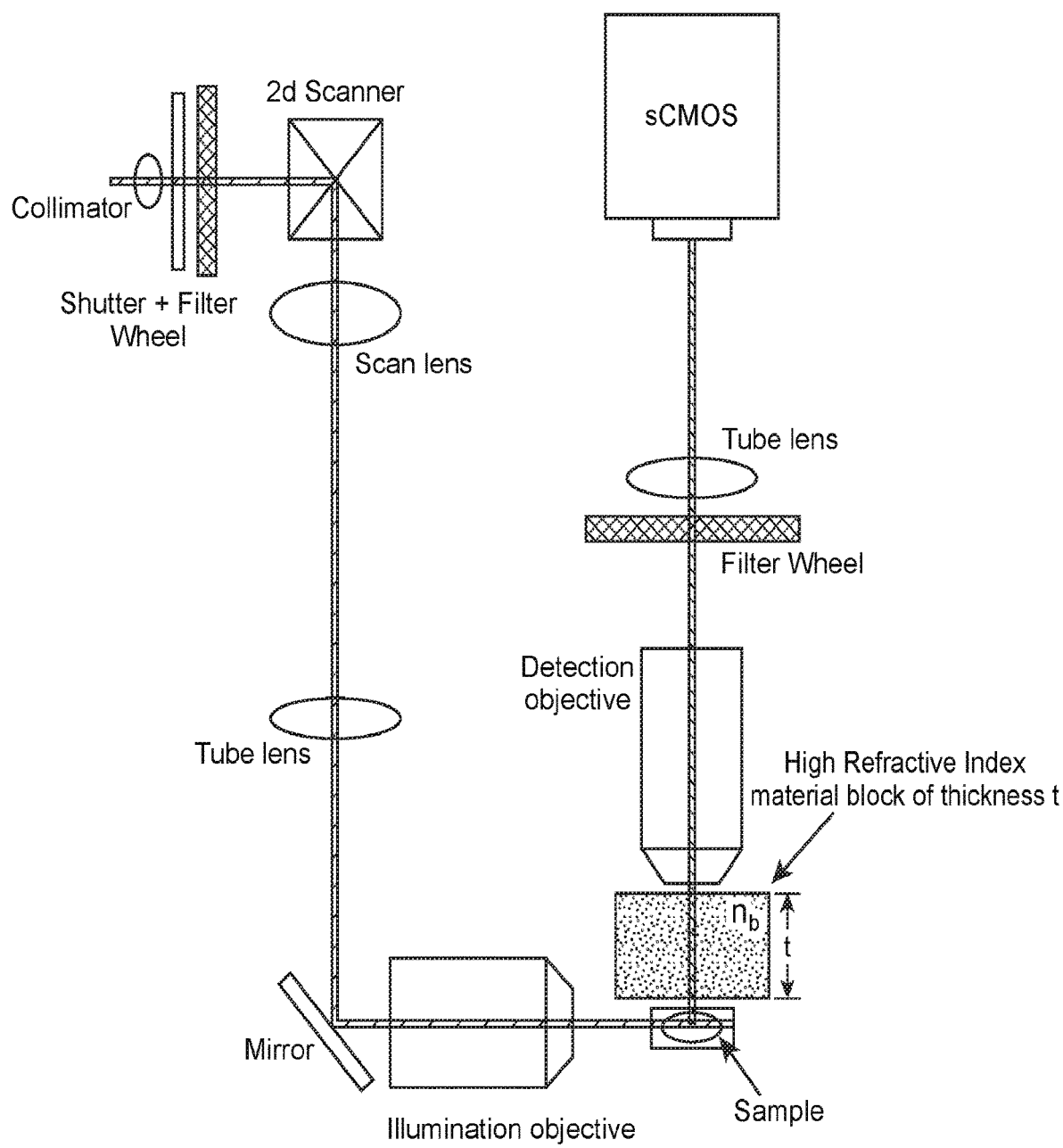
FIGS. 7A-7B are a collection of diagrams and graphs showing the layout of a SPED light sheet microscope, according to embodiments of the present disclosure.
Figure 7B:
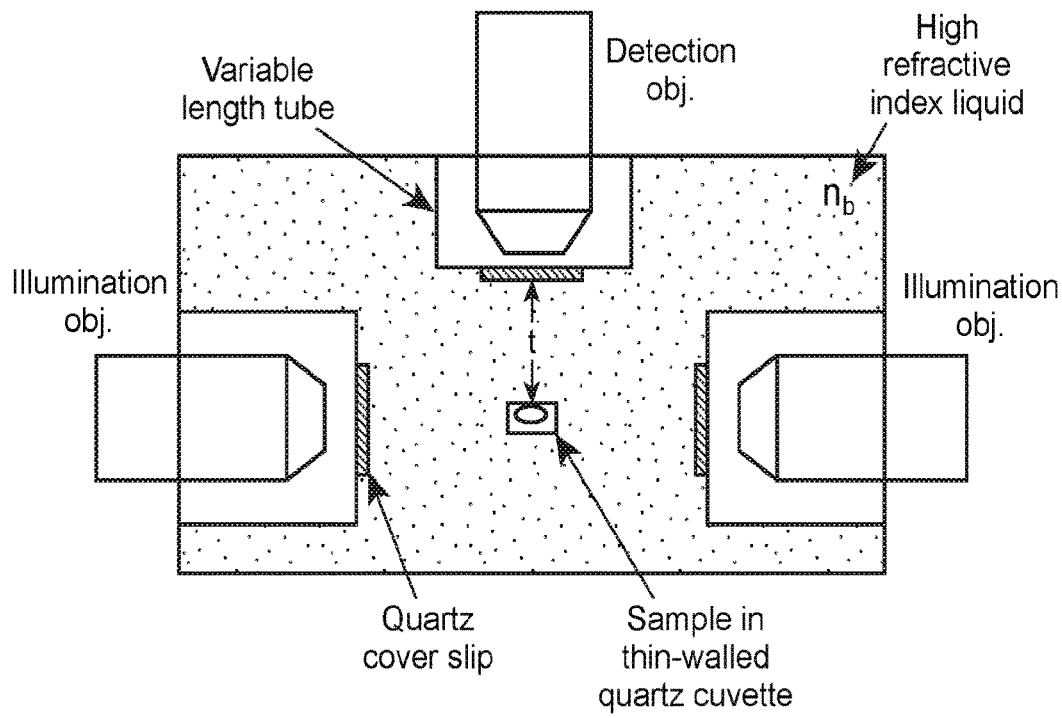

FIGS. 7A and 7B. Optical layout of the SPherical-aberration-assisted Extended Depth-of-field (SPED) light sheet microscope; related to FIGS. 1A-1B. (FIG. 1A) One or two light-sheets (second identical light-sheet illumination path is not shown in the figure) were produced from opposite sides, and the emitted signal was detected with an orthogonal wide-field detection arm. In addition, a block of higher refractive index material was placed between the objective and the sample to induce uniform spherical aberrations for PSF elongation. The illumination arm included laser source, filter wheel, shutter, x-y galvanometer scanner, scan lens, tube lens, mirror and an illumination objective. The detection arm contained a detection objective, filter wheel, tube lens and sCMOS camera. All parts were as described in detail above for COLM. (FIG. 1B) A SPED system was implemented on a CLARITY™-optimized Light-sheet Microscopy (COLM) device. The large horizontal COLM sample chamber was filled with a specific refractive index ($n_b$) liquid (1.454 was used for the most of the experiments described herein) to produce the refractive index blocks for inducing spherical aberration-based PSF extension. Lens tubes (containing quartz glass cover slips for separating the objectives from RI liquid) of varying lengths were used to achieve varying RI block thickness (t). The samples were mounted in custom thin-walled (0.5 mm thick) quartz glass cuvettes. All parts were as described in detail above for the COLM device. Although the SPED system was implemented on the COLM device, SPED was easily adaptable to any light sheet microscope by incorporating a solid block of transparent material of a defined thickness and refractive index to achieve the desired axial elongation of system PSF.

Experimental PSFs and Analysis

1 µm diameter beads were used to assess the PSF of various objectives in the SPED light sheet vs. standard air imaging configurations. PSFs were recorded by synchronously moving the beads and the light-sheet (typically in a z-step of 4 µm), so that the beads remained constantly and uniformly illuminated throughout the image stacks. Beads were manually identified and cropped using Fiji, and were aligned rigidly (with 6 parameters: 3 for translation and 3 for rotation) in Amira Final average PSFs were generated by taking an average of the normalized intensity profiles of all beads (n≥5). Lateral PSF FWHMs as a function of z-position were calculated subtracting the average background level, identifying the bead center in each slice center, and then averaging the FWHM of four cross sections through this center position.

SPED Light Sheet PSF Simulations

The effect of various SPED light sheet system parameters on the PSF extension was assessed by optical simulations performed using Zemax OpticStudio™ 13 (Kirkland, Wash.). The fast Fourier transform (FFT) PSF function, which included the influence of wave-optics for numerical apertures up to approximately 0.4, was used for all simulations. The optical prescription is presented in FIG. 9A. In brief, the objective and the tube lens were approximated as ideal (paraxial) lenses, and focal lengths were set according to the working distance and the overall system magnification. The Numerical Aperture (NA) was set as a system parameter that controlled the size of an aperture stop at the back focal plane of the objective lens. This optical prescription allowed access to all the system parameters: (a) the refractive index of the material in which the sample was embedded and the sample z-position, (b) the thickness and the refractive index of the coverglass separating the sample from the RI liquid, (c) the thickness and refractive index of the RI liquid block, (d) the thickness and refractive index of a coverglass between the RI liquid and the objective, and (e) the thickness of the air gap between the objective and the cover glass. All the surfaces, before the objective, were set to infinite flat curvature. The distance between the tube lens and the sensor was varied for refocusing the position of the camera sensor. A custom macro was used to sequentially step the z-position of the object (in 10 microns steps) to generate the 3D PSF, and custom Python scripts were used to process the Zemax output files.

Figure 9C:
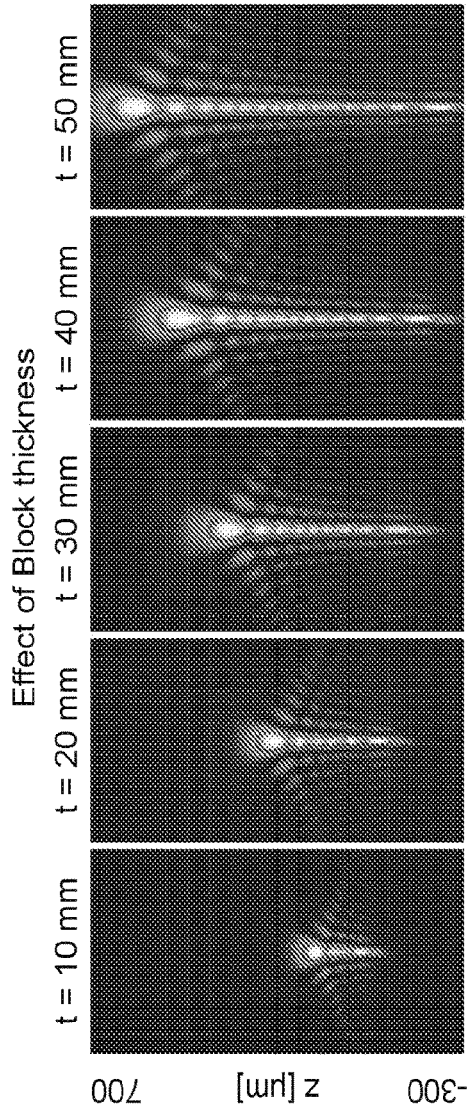
Figure 9D:
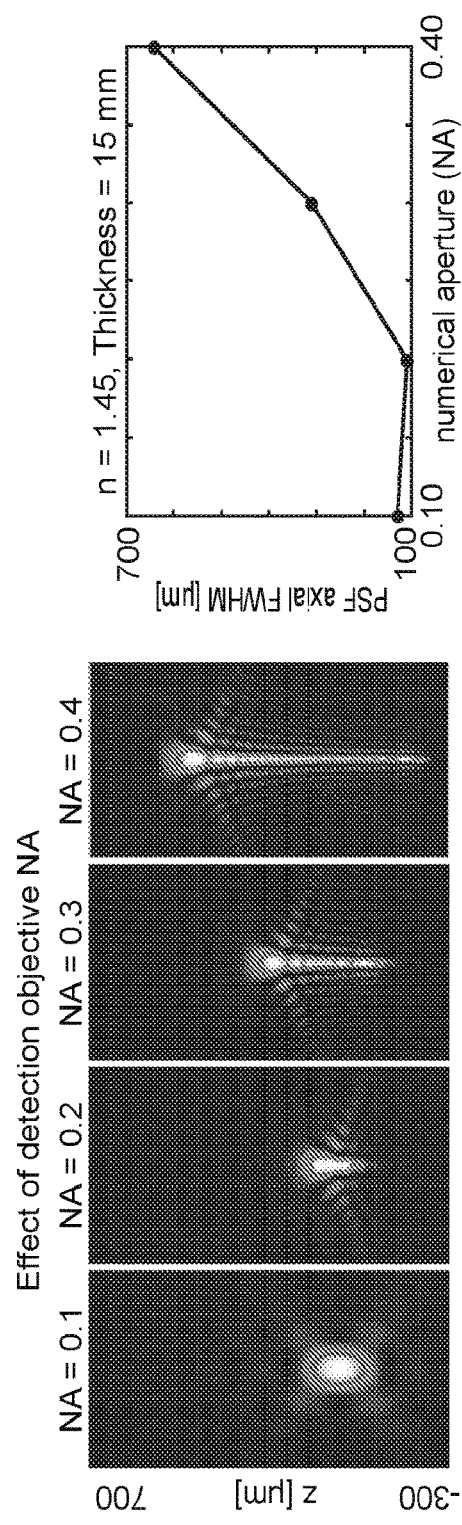

FIGS. 9A-9D. SPED light sheet PSF simulations to identify tuning parameters; related to FIGS. 1A-1D. The detection arm of SPED-LS was modelled in Zemax using the optical prescription shown in (FIG. 9A). FIGS. 9B-9D show images and graphs used to assess the effects of changing the refractive index (RI) of the block, the thickness of the block, and the numerical aperture (NA) of the detection objective, respectively. As summarized in the graphs, the PSF elongation increased with corresponding increases in all the three parameters: linearly with the block thickness, and non-linearly with the RI and the detection objective NA.

Imaging Experiments

A clarified adult mouse brain sample was generated from a Thy1-eYFP transgenic mouse. The sample was incubated in 65% glycerol, and mounted in a quartz cuvette for SPED light sheet (SPED-LS) and standard COLM imaging. Live 10 dpf larval zebrafish, expressing nuclear-localized GCaMP6s Tg(elav13:H2B-GCaMP6s), were mounted in a quartz cuvette and immobilized in a layer of 1% agarose in the corner of the cuvette. SPED light sheet microscopy under different configurations was performed by step-wise rapid scanning of the light-sheet and detecting the corresponding illuminated planes with an sCMOS (Orca™ Flash 4.0 V2) camera. A z-step of 5 μm was used to cover the entire depth in 40 slices. A z-step of 2 μm or 4 μm was used for anatomy images shown in FIG. 3. 4 to 6 microns thick light-sheets were used for the imaging experiments. For light field microscopy (LFM) sample collection, 10 dpf Tg(elav13:H2B-GCaMP6s) larvae were immobilized in 2% low melting point agarose and placed on a standard petri dish filled with fish water. LFM was performed on a modified Leica SP5 using a 10×/0.6 NA Olympus water-dipping objective, 250 mm focal length tube lens, f/11.36 100 μm pitch microlens array (Jenoptics), and Andor® Zyla sCMOS camera. Volumes were collected at 2 Hz.

Deconvolution Pipeline

The SPED data deconvolution pipeline is described in detail in FIG. 11. Standard Richardson-Lucy implementation in Matlab® (Matlab® R2015a, The MathWorks Inc., Natick, Mass.) was used for performing deconvolution. As a first step, the system empirical PSF (for a given objective) was aligned (along the z-axis) with the raw image stack. To achieve this, a subset of z-slices (typically separated by 100 μm) were deconvolved with a set of 2-dimensional (2D) PSFs uniformly sampled across the depth (along z-axis, typically separated by 10 μm) of the 3-dimensional (3D) system PSF. The resulting images were inspected manually for sharpness to determine global mapping of the system PSF with the raw image stack (FIG. 11: step 1). The aligned PSF was then used to deconvolve all the z-slices by 2D PSF image at corresponding mapped z-positions (FIG. 11: step 2). Typically 10-20 iterations were used for the Richardson-Lucy deconvolution. For the time lapse recordings, step 1 of aligning the PSF to the dataset was performed using the first time point. The resulting mapped PSF was then used to deconvolve all the time points (second step).

FIG. 11. SPED light sheet data deconvolution pipeline; related to FIGS. 2A-2C. The schematics summarize the SPED data deconvolution pipeline. In the first step, the empirically determined system PSF was aligned (along z-axis) with the raw data stack. This was achieved by performing deconvolution (Richardson-Lucy) of a small number of z-slices (typically separated by 100 μm) of data with a set of 2D PSFs sampled at different depths (typically separated by 10 μm). The resulting deconvolved images were analyzed (manually or automatically) for sharpness to determine the global z-axis alignment of the system PSF and the raw data stack. In the second step, all the z-slices of the image stack were deconvolved using 2D PSFs sampled from system PSF at correspondingly aligned z-positions. For time lapse datasets, PSF and stack alignment was calculated using the first time point data, which was then used to deconvolve all the time points (second step).

Image Segmentation and Quantitative Analysis

All image segmentation and quantitative analysis were performed using Matlab® (R2015a, The MathWorks Inc., Natick, Mass.), and the DIPimage toolbox (version 2.7) and R. ΔF/F of live functional imaging datasets was calculated as follows. First, a reference 3D image (corresponding to F) was generated by averaging all the time points. ΔF/F was then calculated by subtracting and dividing by the average signal (F). Image segmentation, to identify all cells, was performed on the standard deviation (voxel-wise, across entire time series) of the deconvolved datasets. In brief, a local intensity normalization operation was applied to image volume, and a marker based watershed approach was then used to label all the cells. Traces for all the identified cells were calculated by overlapping the labeled (after segmentation) volumes over the time-lapse datasets. These traces were then subjected to clustering analysis using Hopach package in R. The top 75% (for datasets shown in FIGS. 6A-6B) or 50% (for datasets shown in FIG. 6C) traces (according to variance) were used in the clustering analyses, yielding in best results of 7, 10 and 13 significant clusters (average correlation≥0.75, with at least 10 cluster members).

Example 2: SPED Light Sheet Microscopy

Extension of depth-of-field was combined with the optical sectioning of light sheet microscopy (LSM) to develop SPED light sheet (FIGS. 1A-1D; FIGS. 7A-7B). To implement this approach, a scalable method for extending the depth of field of an objective used to image a large intact tissue volume was sought. Building upon the observation that spherical aberration in optical systems resulted in PSF elongation, a simple and robust strategy to use a thick block of higher refractive index material (beyond the design specifications of the objective), between objective and sample was devised, thereby introducing significant but uniform spherical aberration (FIG. 1A). This approach extended the depth-of-field by orders of magnitude while substantially maintaining lateral extent of the PSF (FIGS. 8A-8C), since peripheral rays traveled a longer distance in the higher refractive index material compared to central rays, and thus focused on different points along the axis, resulting in an elongated PSF (FIGS. 8A-8C).

Figure 1B:
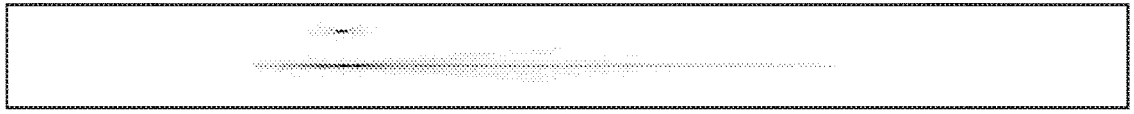
Figure 1B:
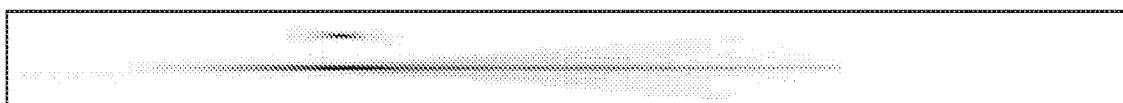
Figure 1B:
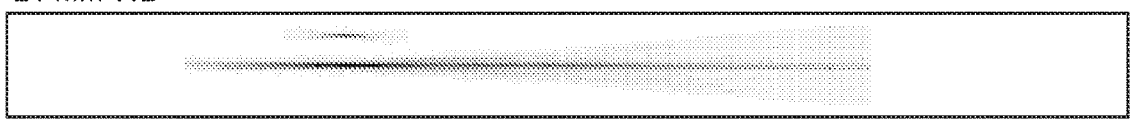
Figure 1B:
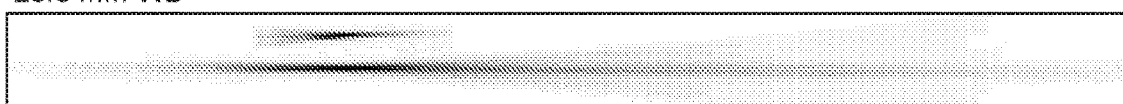
Figure 1C:
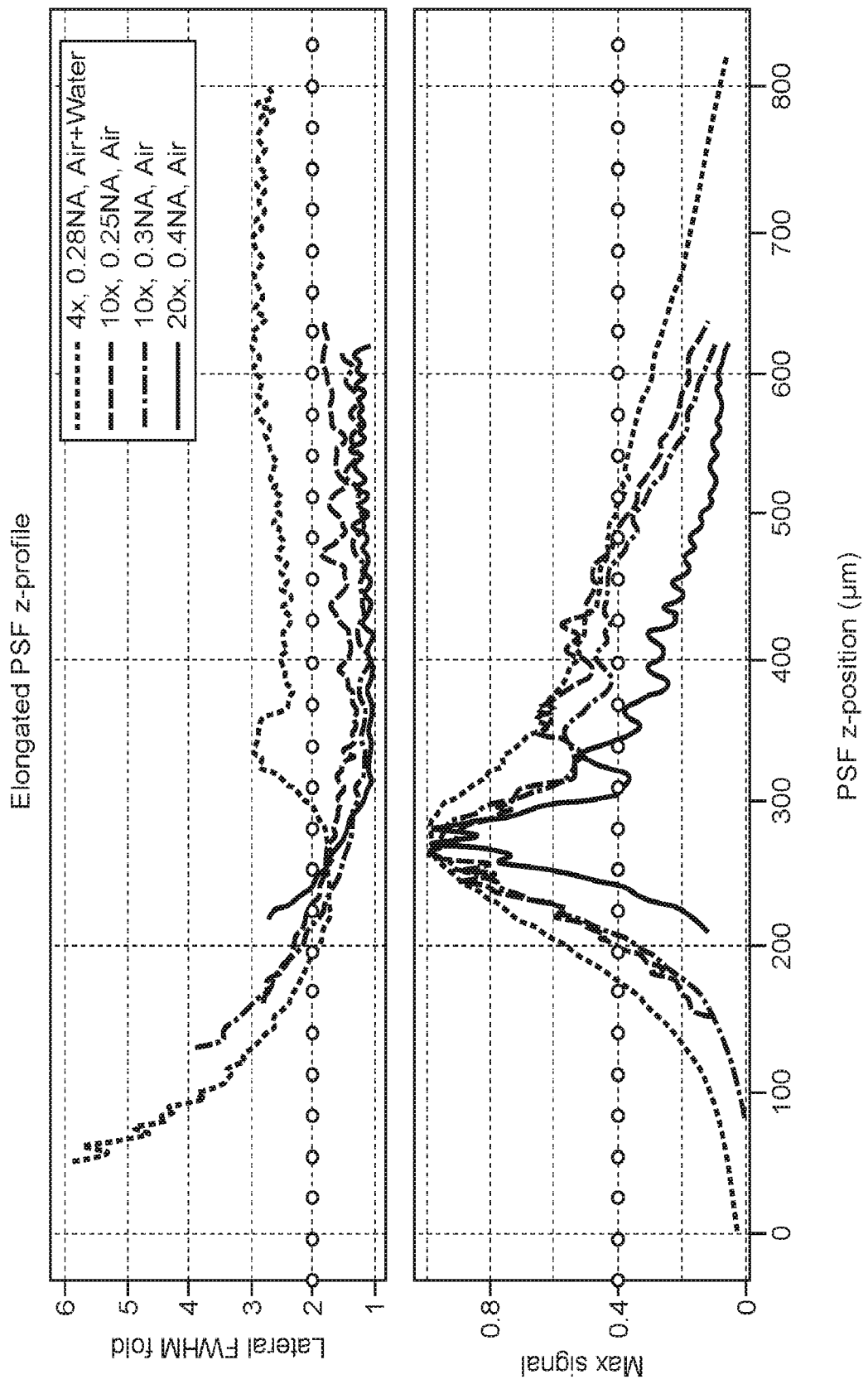
Figure 1D:
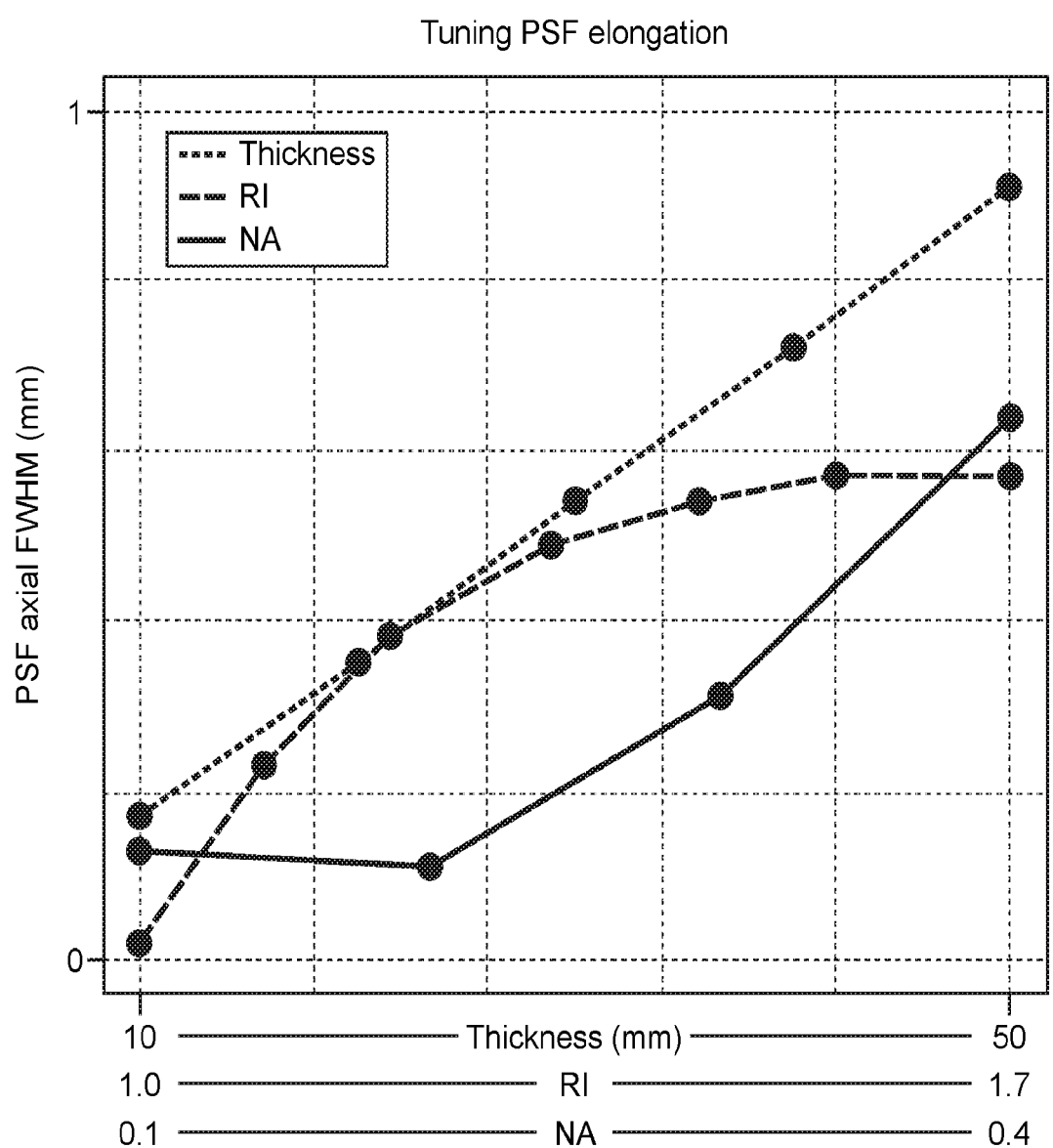

FIG. 1A-1D. SPherical-aberration-assisted Extended Depth-of-field (SPED) light sheet microscopy. (FIG. 1A) SPED light sheet concept compared with standard light-sheet microscopy (FIG. 1A, left). In standard light-sheet scanning (left), the light-sheet and the detection objective are moved synchronously to acquire a 3-dimensional volume. The detection objective is typically mounted on a piezo motor for synchronous z-scanning. This design limits the speed of imaging (1-3 volumes per second) because of the mass of the objective and also limits the depth coverage to piezo travel range (typically a few hundred microns). SPED light sheet scanning (FIG. 1A, middle) combines a greatly extended depth of field with the optical sectioning of light sheet to provide the capacity to scan thousands of volumes per second. A simple and scalable method according to the present disclosure (FIG. 1A, right) was developed to extend the PSF by more than an order of magnitude. The method according to the present disclosure involved placing of a block of higher refractive index ($n_b$) material between the objective and the sample to induce spherical aberrations that elongated the PSF. As shown in FIG. 1A, t, was the thickness of the higher refractive index block. (FIG. 1B) A comparison of the native PSF of an objective (measured in air) with the elongated PSF, for four different objectives: Olympus 20×/0.4 NA/12 mm working distance (WD)/Air, Nikon 10×/0.3 NA/16 mm WD/Air, Olympus 10×/0.25 NA/21 mm WD/Air and Olympus 4× 0.28 NA/29.5 mm WD/Air+Water (5 mm). The working distance (WD) of the objective was the space between the objective and the sample. The 3-dimensional SPED light sheet empirical PSF measurements for each objective were obtained (see Methods above) by scanning 1 μm-diameter beads and the light sheet synchronously (thus maintaining the uniform illumination of beads) along the z-axis, while keeping the detection objective stationary. Individual bead images (n≥5) were manually extracted from the 3D image volume to generate the final average PSFs. A block of refractive index (1.454) liquid was used to span the entire available working distance of the objective (see FIGS. 7A-7B for further details). As shown in FIG. 1B, the scale bar is 100 µm. (FIG. 1C) Characterization of PSF elongation. The top graph in FIG. 1C plots the fold change in lateral FWHM of the PSF as function of z-position relative to the minimum FWHM of the non-extended air PSF of the same objective. The distribution shows that the lateral extent of PSF (i.e., lateral resolution) remained largely unchanged for several hundred microns. Note: 4×/0.28 NA objective was designed for air and 5 mm thick water layer, because of which the PSF measured in air showed aberrations. The bottom graph in FIG. 1C plots the maximum intensity of the PSF as a function of depth. (FIG. 1D) Simulations of the SPED microscope were performed to assess the effect of the SPED-LS system parameters: Refractive Index (RI) of the block, thickness of the block (t), and the NA of the detection objective used. The PSF elongation increased rapidly and reached saturation with increasing RI of the block, increased linearly with the RI block thickness, and increased non-linearly with the increasing NA of the detection objective used. See also FIGS. 7A-7B, 8A-8C, 9A-9D for details of SPED-LS implementation and PSF simulations.

Figure 8A:
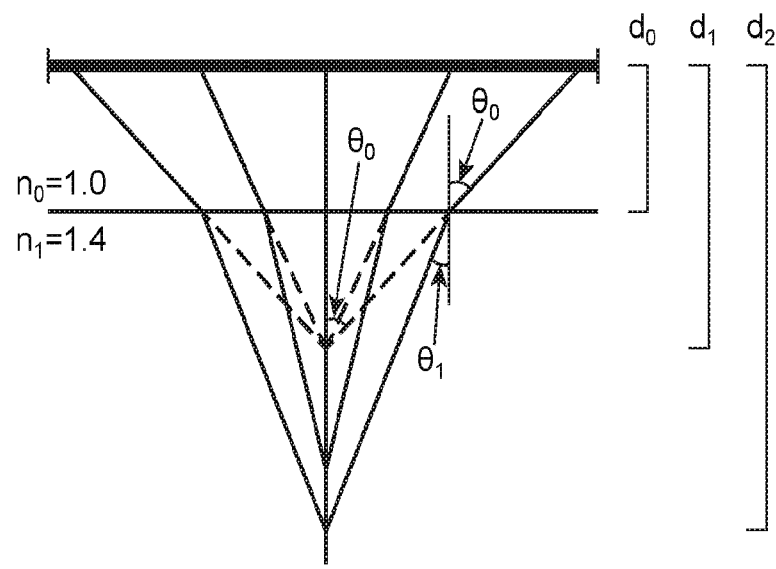
FIGS. 8A-8C are a collection of diagrams and graphs showing an optical mechanism underlying SPED light sheet microscopy, according to embodiments of the present disclosure.
Figure 8B:
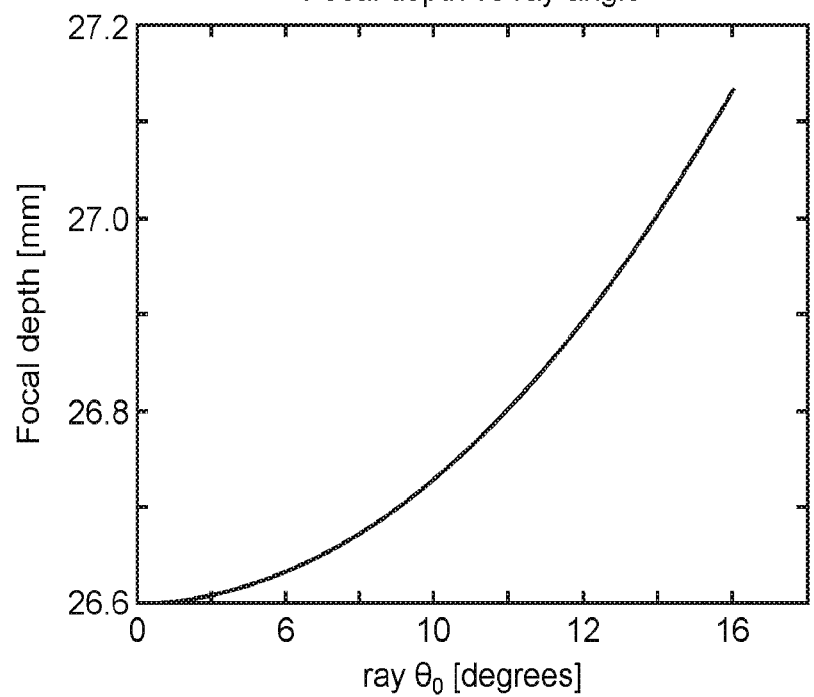
Figure 8C:
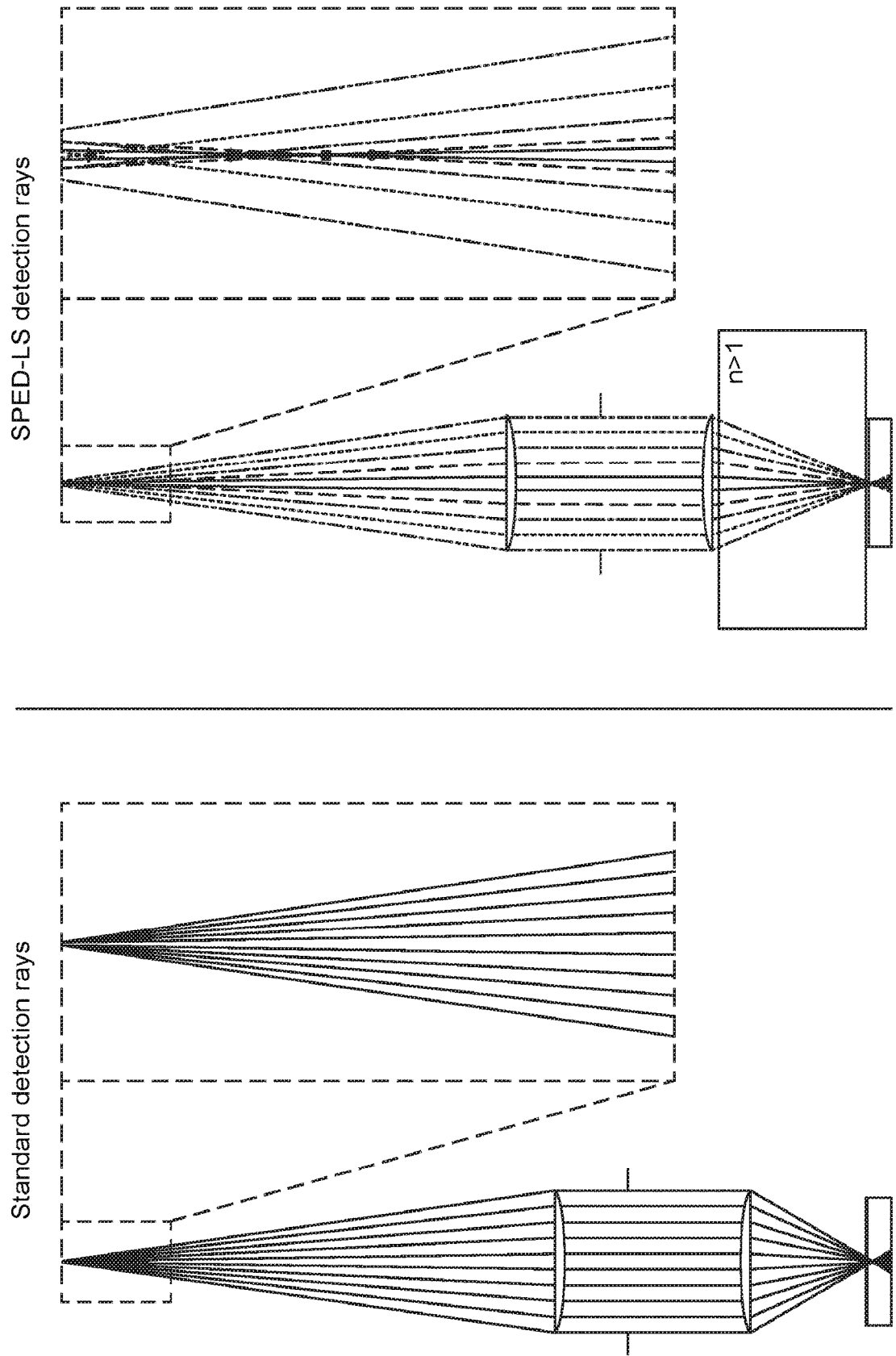

FIG. 8A-8C. Optical mechanisms underlying SPED light sheet microscopy; related to FIGS. 1A-1D. Spherical aberrations elongated the PSF by focusing rays that pass through different parts of the objective aperture at different distances. (FIG. 8A) Ray tracing example to demonstrate the extension of depth of focus caused by introduction of a high refractive index material in the optical path. (FIG. 8B) Relationship between the incidence ray angle (the sine of which defines the numerical aperture) and the focal depth, demonstrating PSF elongation by the introduction of a block of high refractive index material. (FIG. 8C) Comparative ray tracing of a normal (aberration-free; FIG. 8C, left) and SPED detection systems (FIG. 8C, right), demonstrating the elongation of the PSF achieved in SPED light sheet, compared to normal.

Figure 7B:
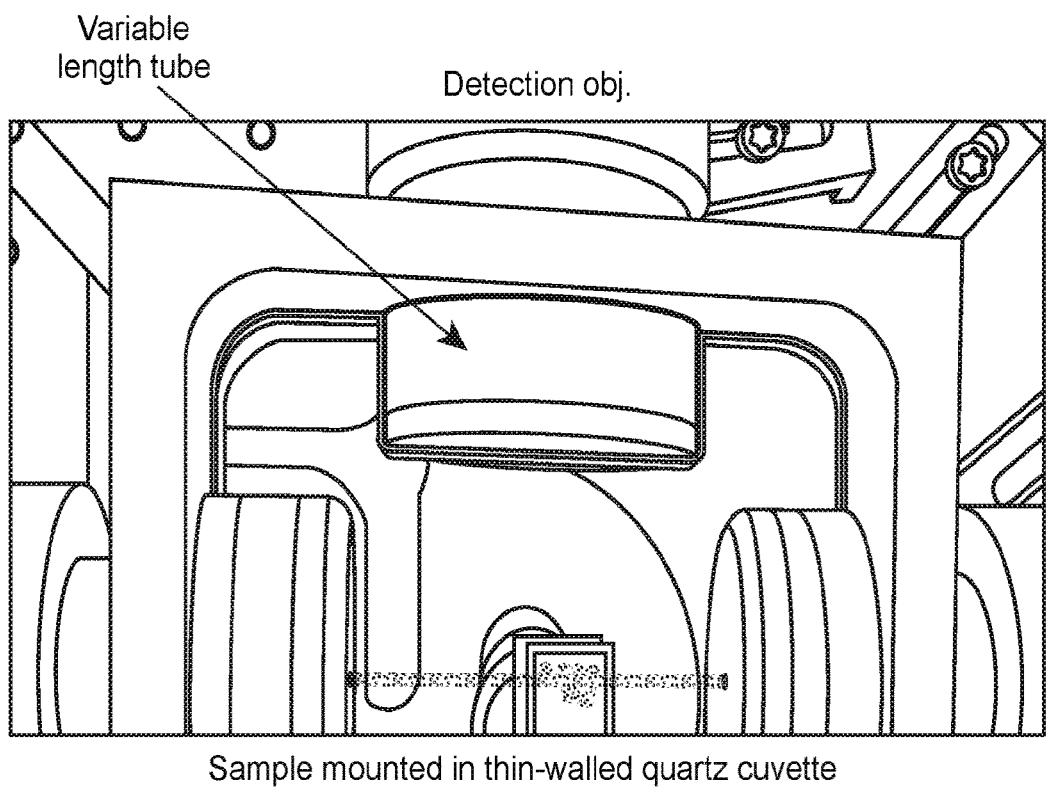

Four different objectives were tested, which spanned a broad range of specifications: (a) 4×, 0.28 NA, 29.5 mm working distance (WD), air+5 mm water; (b) 10×, 0.25 NA, 21 mm WD, air; (c) 10×, 0.3 NA, 17 mm WD, air; and (d) 20×, 0.4 NA, 11 mm WD. The WD of the objectives (i.e., the space between the objective and the sample) was filled with a column of liquid with a refractive index of 1.454 (FIG. 1C; FIG. 7; Example 1). As shown in FIG. 1B, this approach yielded substantial PSF elongation, compared to the native PSF of each objective in air, while maintaining the lateral extent of the PSF (note that the 4×/0.28 NA objective was designed for air and 5 mm of water column, therefore, the measured PSF in air alone, shown in FIG. 1B, had spherical aberrations as expected.) FIG. 1C shows quantification of the elongated PSFs showing that the lateral extent remained largely unchanged (FIG. 1C, top) and that several hundred microns of the elongated PSFs were usable for volumetric imaging (FIG. 1C, bottom).

Next, parameters that can be tuned to generate a desired depth of PSF were sought and assessed. For this the SPED system was first modeled and simulations were performed (see FIG. 9A-9C and Example 1 for Zemax modeling and simulation details). As summarized in FIG. 1D and FIGS. 9B-9D, PSF elongation was dependent on three parameters of the system, namely the thickness of the refractive index block, the refractive index of the block, and the NA of the detection objective. An increase in the refractive index of the block was found to give rise to linear elongation that saturated as the refractive index approached 1.7 (FIG. 9B).

The PSF also could be elongated linearly by increasing the block thickness, the maximum of which was dictated by the WD of the objective (FIG. 9C). Finally, an increase in the NA of the detection objective gave rise to a large non-linear elongation of the PSF (FIG. 9D). These results generally were concordant with measured experimental PSFs for the four different objectives, indicating that this framework could serve as a resource for choosing objectives with desired PSF properties, and for customizing objectives to induce spherical aberrations.

Figure 2A:
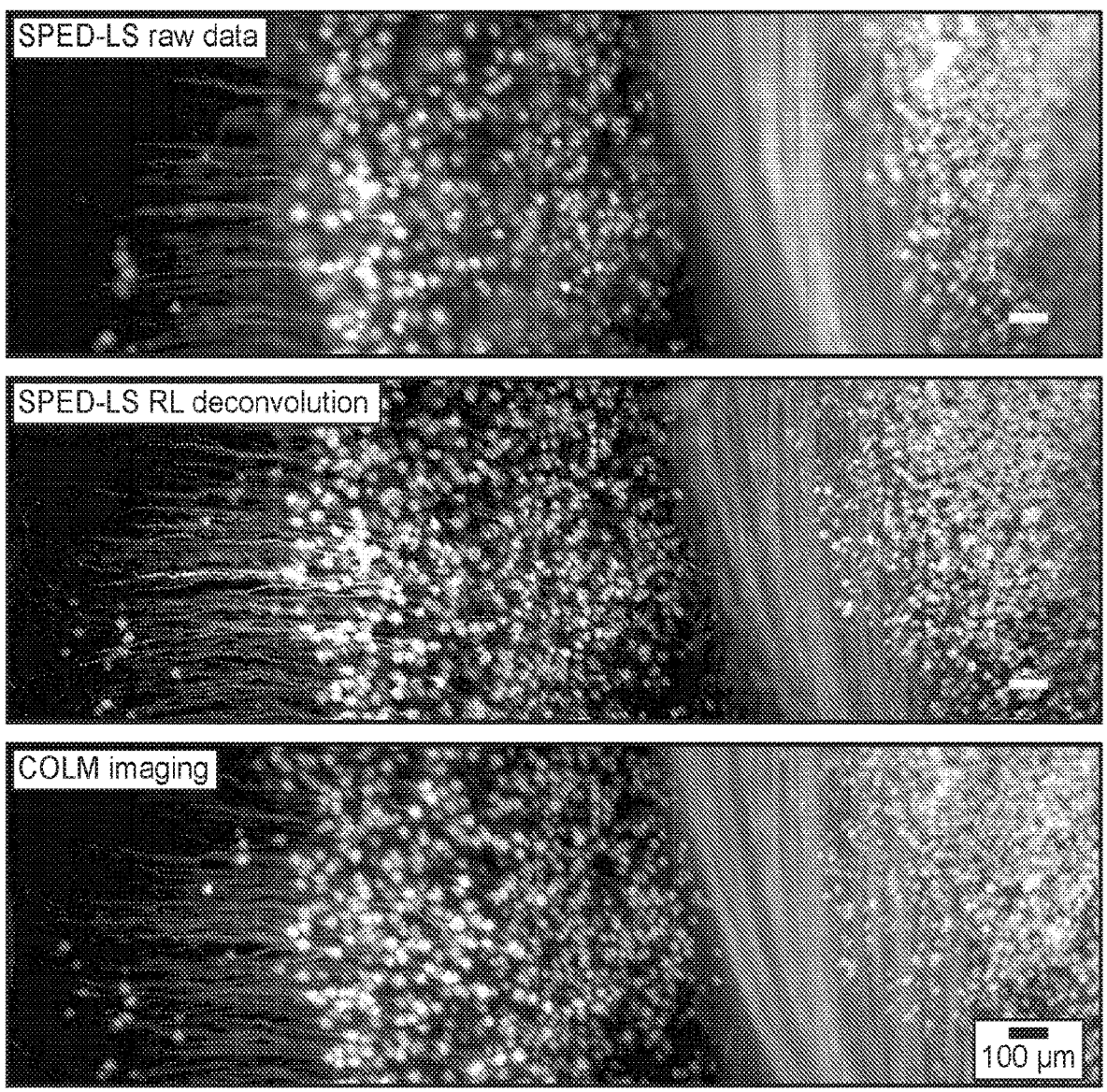

Example 3: Deep Cellular and Neurite-Resolution Volumetric Imaging with SPED Light Sheet To assess the imaging depth and quality of SPED light sheet microscopy, imaging of a relatively homogenous Thy1-eYFP mouse brain sample, clarified using the passive CLARITY™ protocol, was performed. The intact brain sample was imaged using a 4×/0.28 NA objective, with the entire WD filled with a block of RI 1.454 liquid. FIGS. 2A and 2B show signal collected from a 1 mm thick tissue block; the image quality was reduced at the top and the bottom slices of the stack due in part to the lateral broadening of the PSF at its axial limits. Therefore, the standard Richardson-Lucy deconvolution method was tested, using the experimentally-measured PSF, and it was found that much of the information (including neurite-resolution features) could be readily restored, as shown in the comparison of x-y and x-z projections of raw SPED, Richardson-Lucy deconvolved, and standard CLARITY™-optimized light sheet microscopy (COLM) imaging data (FIGS. 2A-2C, FIG. 10, FIG. 11).

Figure 2C:
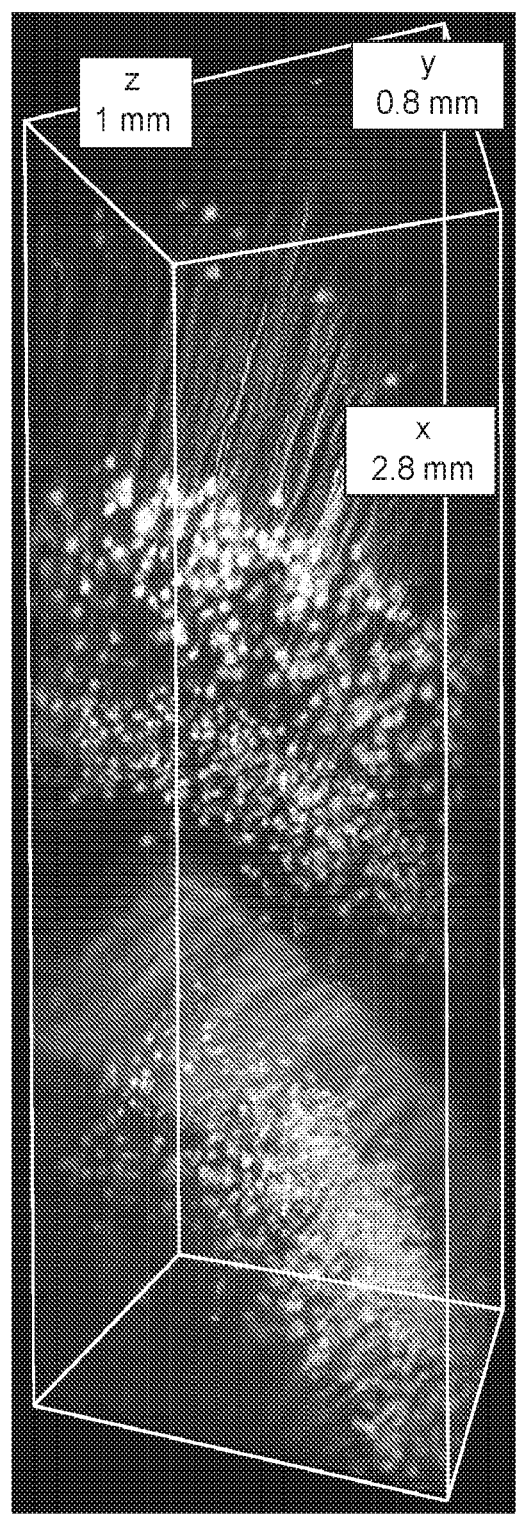

FIGS. 2A-2C. SPED light sheet imaging depth characterization. 1 mm deep volumes of clarified Thy1-eYFP transgenic mouse brain were imaged with SPED light sheet microscopy and with CLARITY-optimized light sheet microscopy (COLM) to assess the SPED imaging depth. (FIG. 2A) compares the x-y projections and (FIG. 2B) the x-z projections of the raw SPED light sheet image volume, after deconvolution using standard Richardson-Lucy deconvolution with the empirically measured PSF and the standard COLM imaging by moving the sample through stationary light-sheet and in-focus detection objective. (FIG. 2C) Volume rendering of the SPED light sheet volume. See also FIG. 10 for detailed comparison of SPED raw and deconvolved data with the COLM imaging, and FIG. 11 for a detailed description of the deconvolution pipeline.

Figure 10:
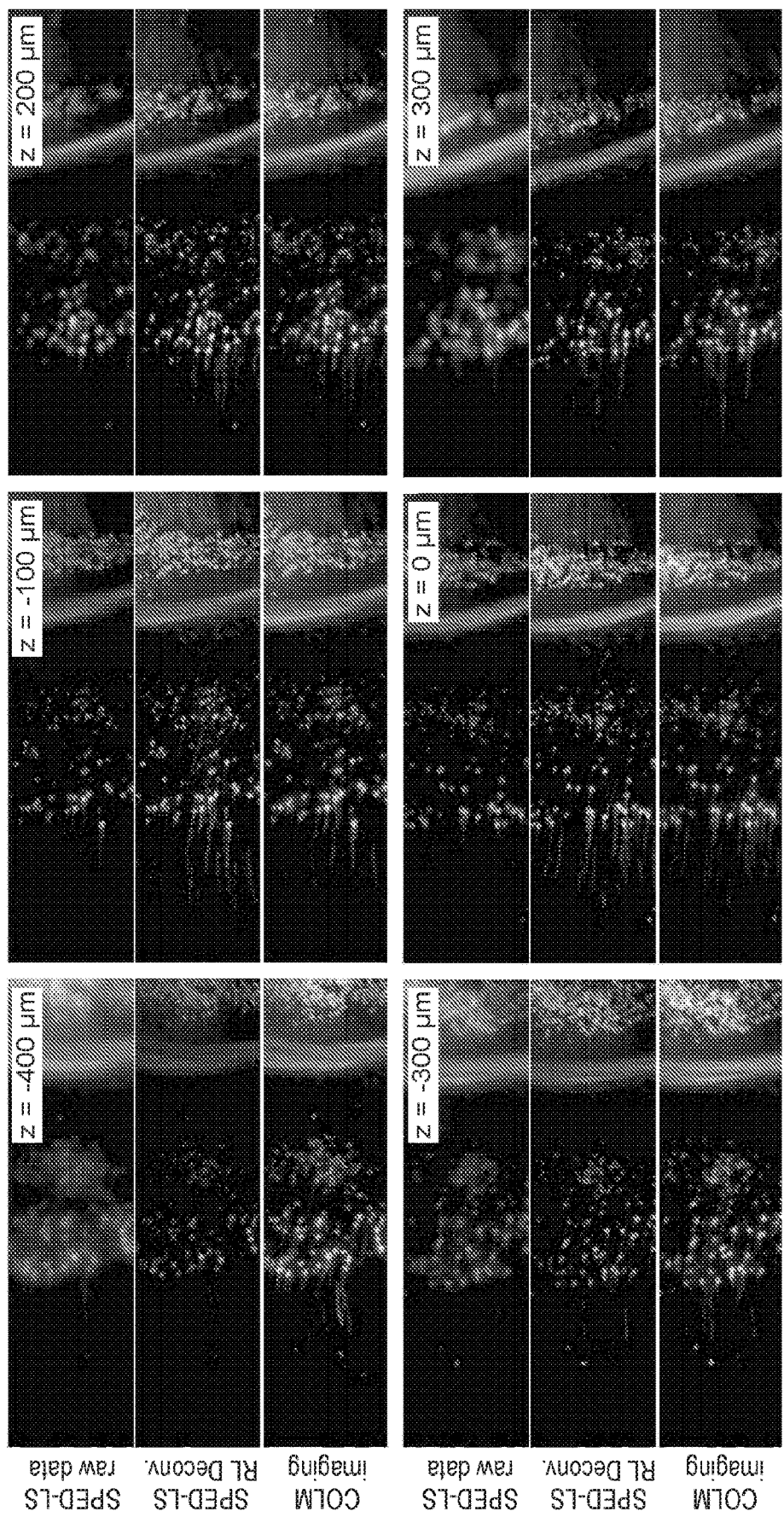
FIG. 10 is a collection of images comparing SPED light sheet microscopy with standard CLARITY™-optimized Light-sheet Microscopy (COLM) imaging, according to embodiments of the present disclosure.
Figure 10:
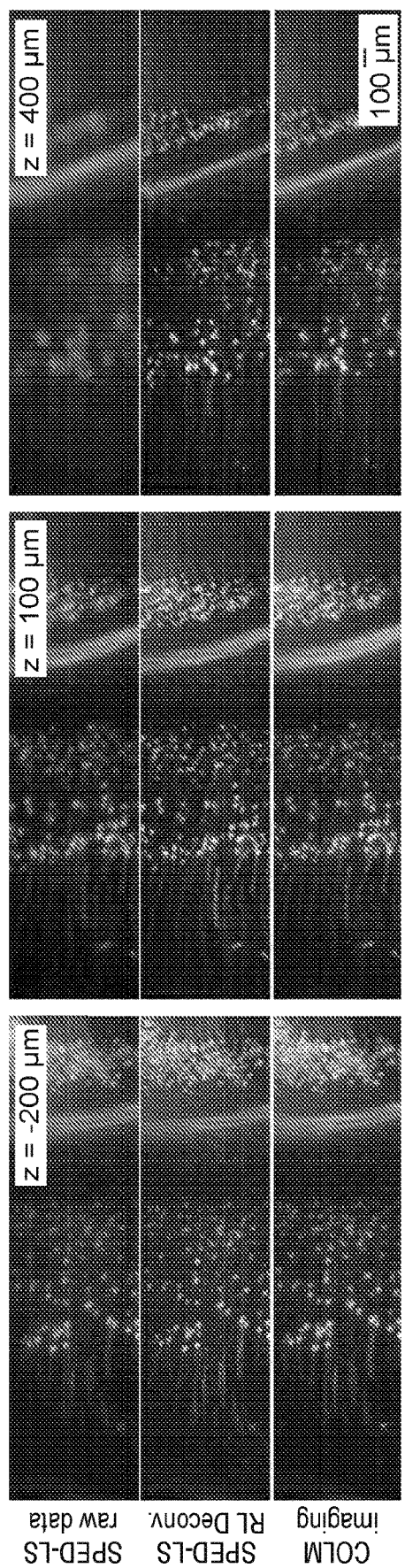

FIG. 10. Comparison of SPED light sheet microscopy with standard COLM imaging; related to FIGS. 2A-2C. A consecutive series of optical sections (100 µm thick) is shown to demonstrate the volumetric imaging capability of SPED light sheet microscopy. The image volumes were acquired by SPED and COLM, using 4×/0.28 NA detection objective, of the same sample volume of a clarified Thy1-eYFP transgenic mouse brain. Each panel shows SPED raw and deconvolved images and the corresponding optical sections from the COLM stack. The z-axis positions (the middle of the stack was set as 0 µm) are labelled in yellow, marking the position of the middle slice of the 100 µm thick optical sections. Detailed volume rendering of the image stack is shown in FIG. 2C. Scale bar is 100 µm.

Figure 12:
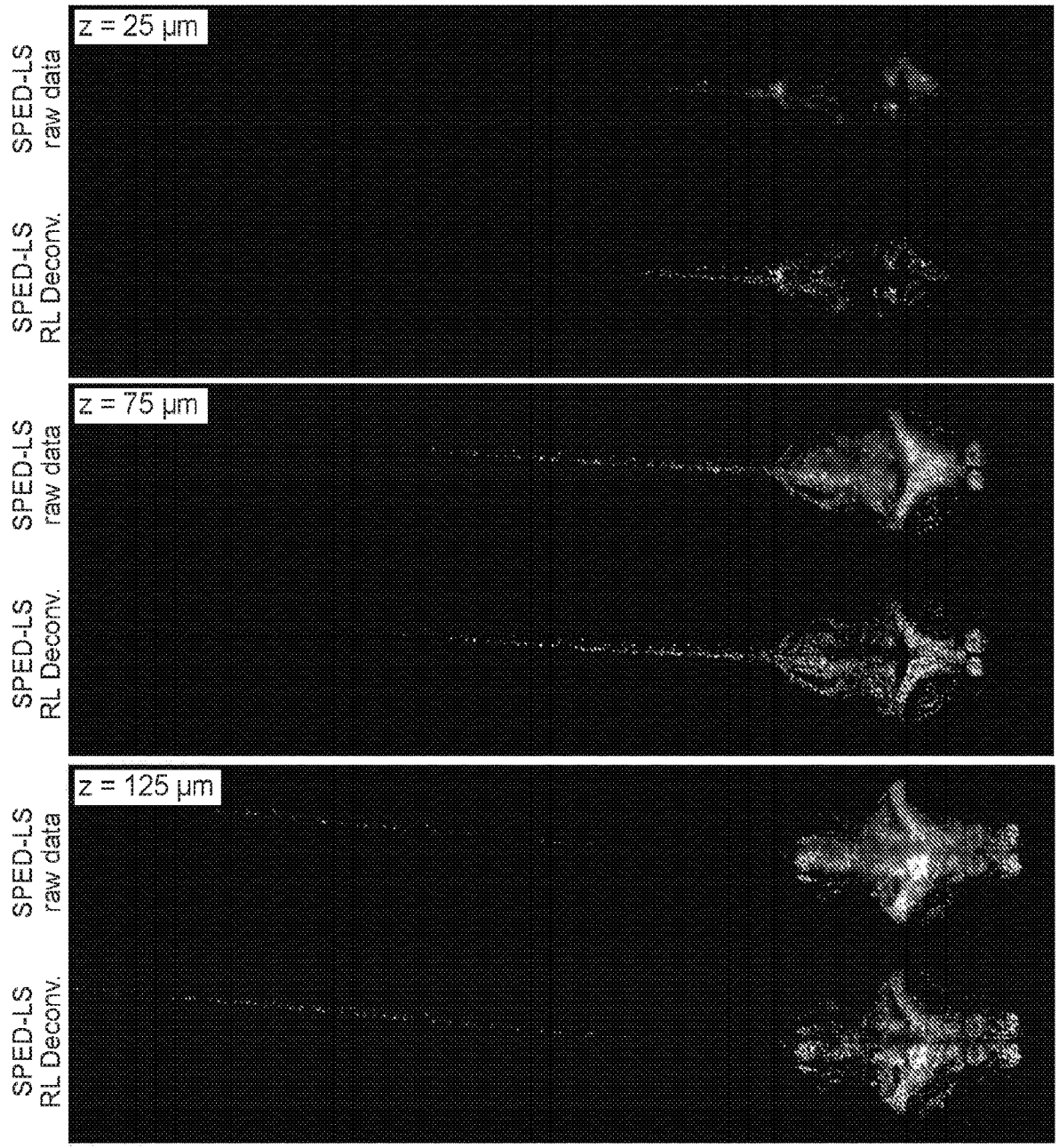
FIG. 12 is a collection of images showing a comparison of raw and deconvolved SPED light sheet data stack, according to embodiments of the present disclosure.
Figure 12:
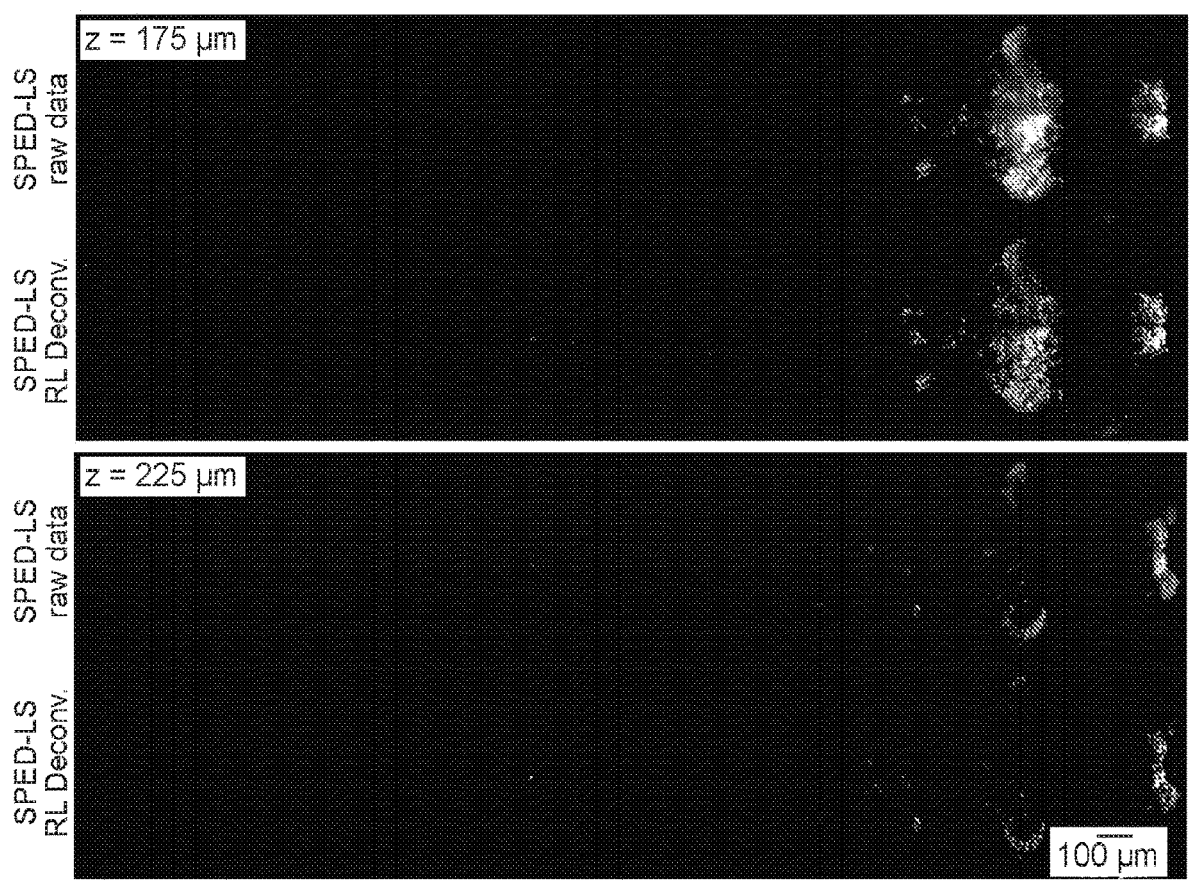

Next, imaging quality in live zebrafish larvae was assessed. Image stacks from live, unparalyzed zebrafish larvae (expressing nuclear localized GCaMP6s, Tg(elavl3: H2B-GCaMP6s)) were acquired with two different objectives: 4×/0.28 NA and 10×/0.25 NA. As demonstrated in FIGS. 3A-3B, FIG. 12, SPED light sheet allowed cellular resolution imaging of the entire zebrafish nervous system. Cellular resolution was demonstrated by automated image segmentation of the cell nuclei in live imaging datasets, as discussed below.

Figure 3A:
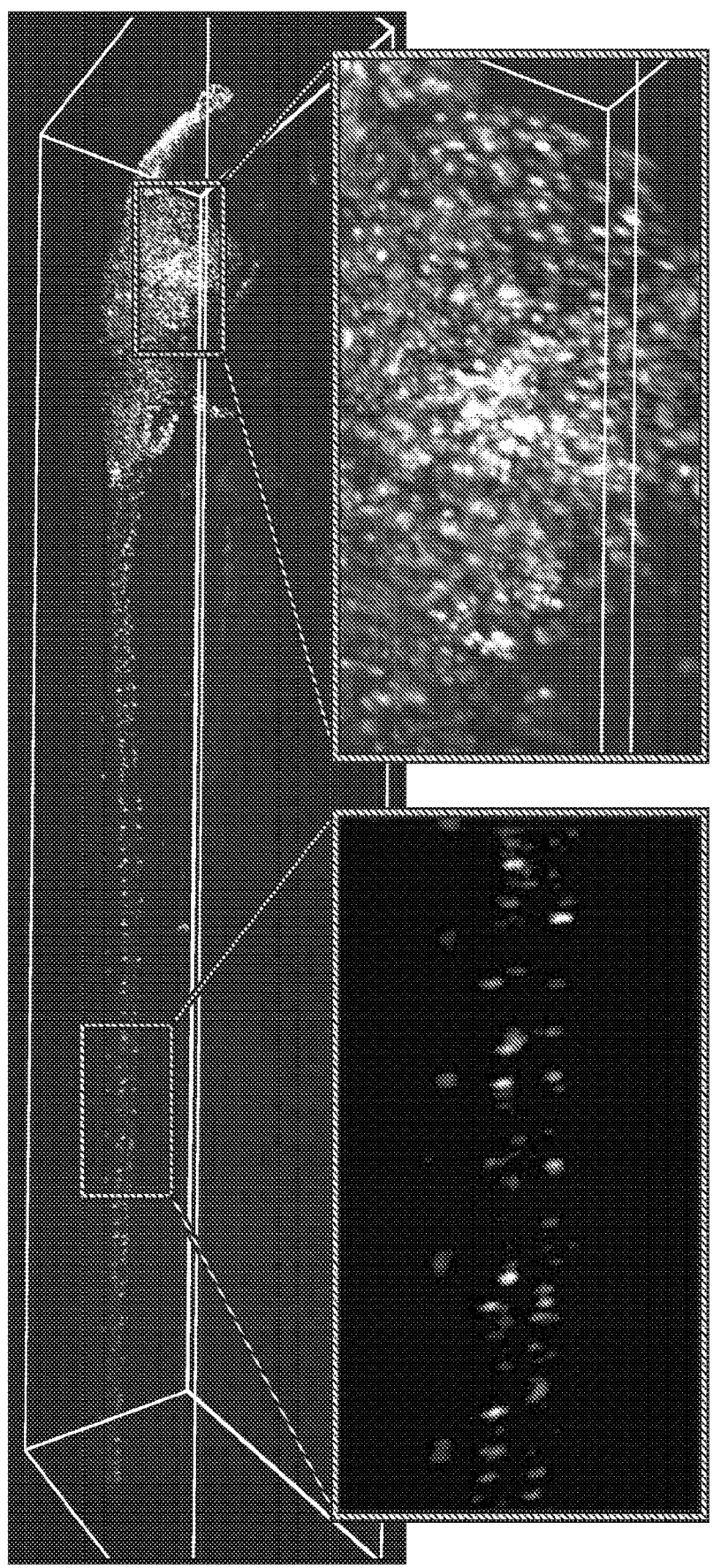

FIGS. 3A-3B. Cellular-resolution imaging of the entire larval zebrafish nervous system with SPED light sheet microscopy. Volume renderings of 10 dpf Tg(elav13:H2B-GCaMP6s) zebrafish larvae imaged with 4×/0.28 NA (FIG. 3A) and 10×/0.25 NA (FIG. 3B) objectives demonstrated the large field of view of SPED microscopy, while maintaining cellular resolution. As shown in FIG. 3A, cyan (left) and magenta (right) boxes provide magnified views. (FIG. 3A) Image volumes of 10 consecutive time points were collapsed into one volume by taking the maximum values voxel-wise across the recording duration. The bounding box size is 0.75 mm×2.99 mm×0.48 mm (FIG. 3B) Image volumes of 7 consecutive time points were collapsed into one volume by taking the maximum values voxel-wise across the recording duration. The bounding box size is 0.65 mm×1.20 mm×0.30 mm. See also FIG. 10 for comparison of raw and deconvolved data.

Example 4: Comparison of SPED with Light Field Microscopy

An implementation of SPED microscopy was performed using scanning of the light-sheet using only galvanometer scanners which can run at several KHz, which provided the ability to scan thousands of volumes (>1 mm deep) per second, while maintaining lateral (determined by detection objective NA) and axial (determined by light-sheet thickness) resolution. SPED volumetric imaging speed may be affected by the data acquisition rate of sCMOS cameras, which are fast and continuously improving.

Figure 4:
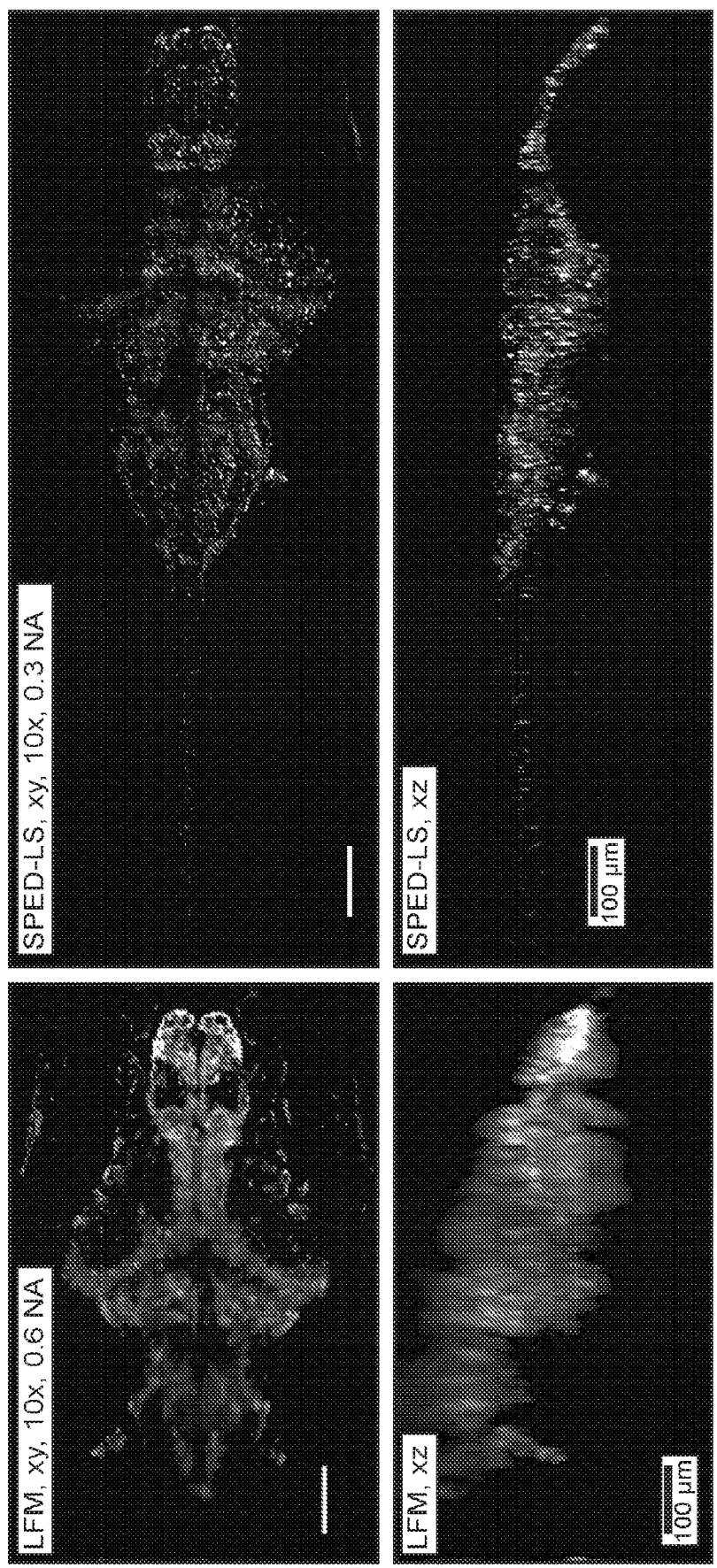
FIG. 4 is a collection of images showing a comparison between light field microscopy (LFM) and SPED light sheet methods, according to embodiments of the present disclosure.
Figure 5A:
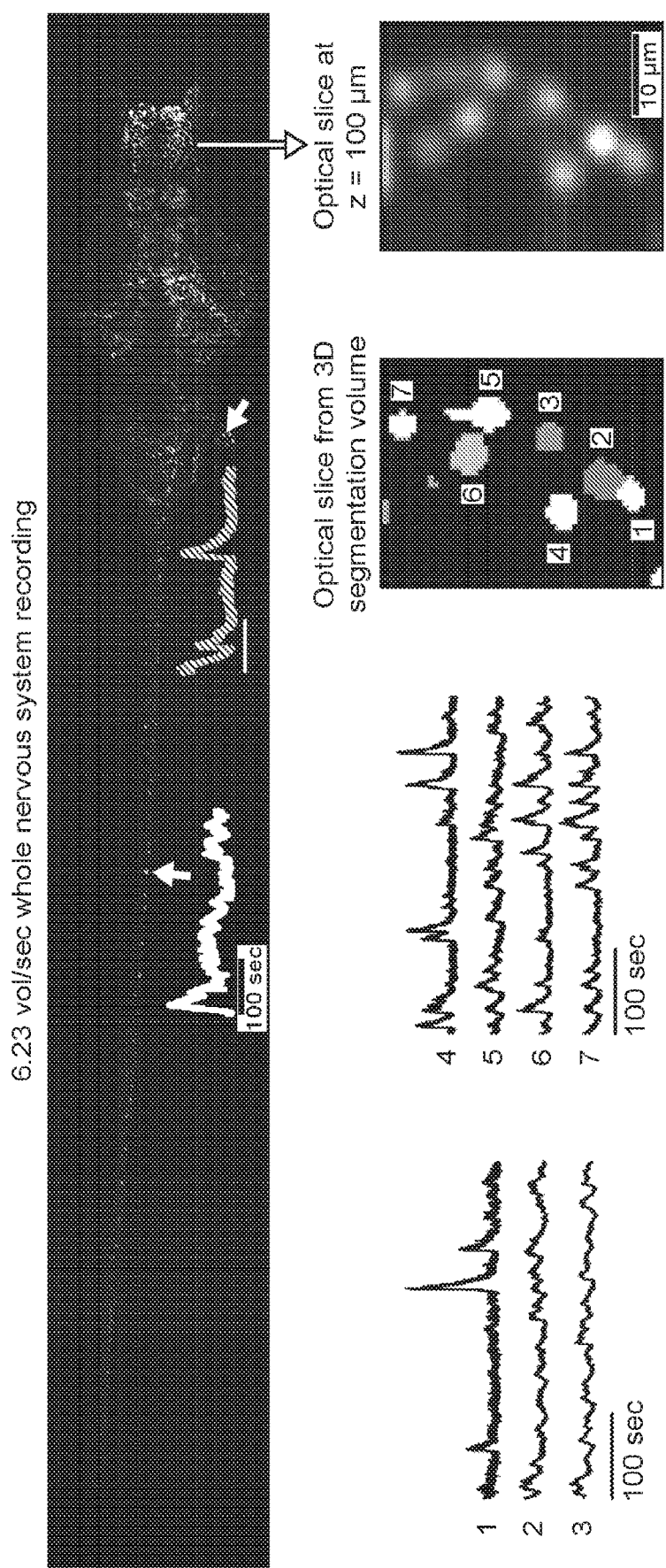
FIGS. 5A-5C are a collection of images and graphs depicting cellular resolution functional mapping of the nervous system of an entire animal using SPED light sheet microscopy, according to embodiments of the present disclosure.
Figure 5B:
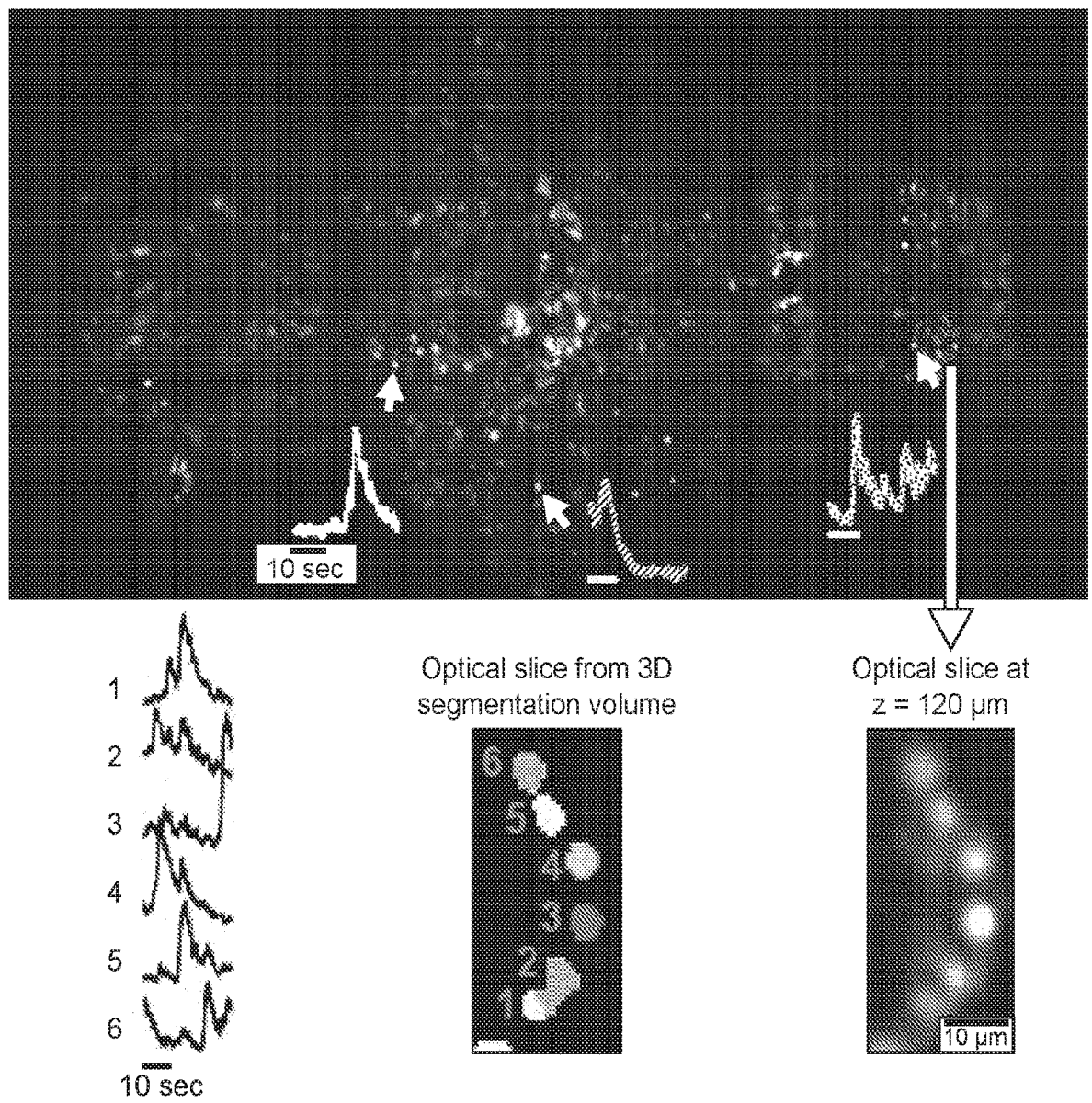
Figure 5C:
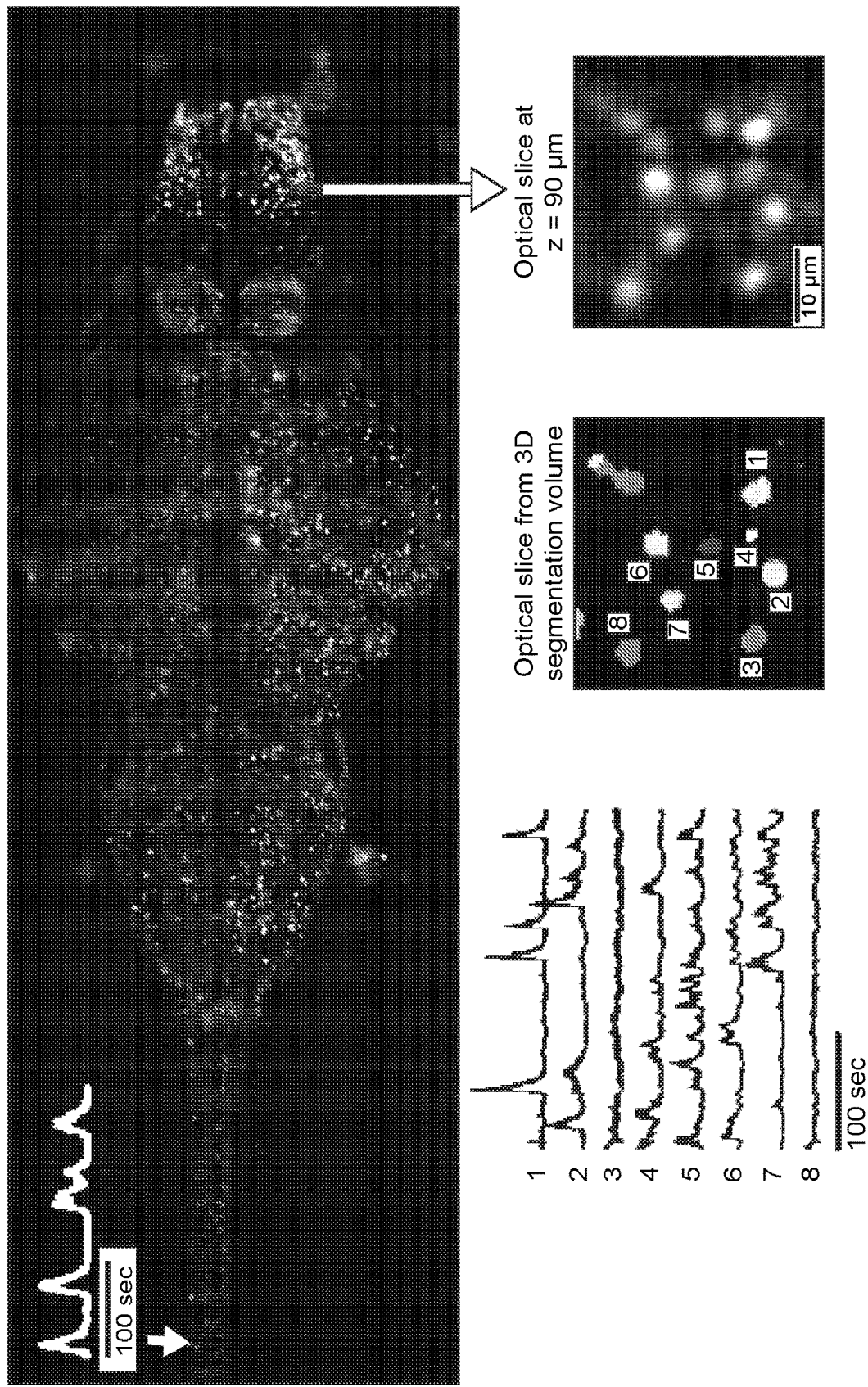

The quality of image volumes acquired with LFM and SPED light sheet microscopy were directly compared. An Tg(elav13:H2B-GCaMP6s) zebrafish larva sample was imaged with LFM methods, followed by SPED light sheet imaging, using comparable parameters. The LFM image stack was acquired with 500 ms exposure using a 10×/0.6 NA (Olympus) water immersion objective and f/11.36, 100 µm pitch lenslet array, whereas the SPED light sheet volume was acquired with 460 ms exposure at half the NA (10×/0.3 NA; Nikon), thus yielding comparable exposure times (500 ms for LFM, 460 ms for SPED light sheet). As shown in FIG. 4, SPED light sheet provided higher lateral and axial resolution, even at 12 volumes per second (40 z-slices, <100 ms exposure per stack; FIG. 5A-5C). Both SPED light sheet and LFM volumetric imaging rates are affected by the camera acquisition speed (currently ~1000 images per second for smaller ROI)—LFM acquired the entire volume per snapshot, compared to the one plane per snapshot of SPED light sheet.

FIG. 4. Comparing resolution of light field microscopy (LFM) and SPED light sheet methods. Three-dimensional volumes were acquired from a 10 dpf Tg(elav13:H2B-GCaMP6s) zebrafish larvae with LFM and SPED light sheet microscopy, using 10×/0.6 NA (water immersion, Olympus) objective with 500 ms exposure and 10×/0.3 NA (air, Olympus) objectives with 460 ms exposure, respectively. SPED light sheet images in FIG. 5B were acquired with less than 100 ms exposure/volume, still yielding cellular resolution. Scale bars: 10 µm.

Example 5: Rapid Cellular-Resolution Functional Imaging of the Entire Larval Zebrafish Nervous System To demonstrate the high-speed, cellular-resolution and large field-of-view volumetric imaging capabilities of SPED light sheet, fast cellular-resolution spontaneous activity over the entire zebrafish larval brain, or the entire nervous system (including the brain and the fully extended spinal cord) was captured. Live imaging of Tg(elav13:H2B-GCaMP6s) zebrafish larvae were performed using two different objectives: 4×/0.28 NA and 10×/0.25 NA. In SPED light sheet microscopy, imaging speed is affected by camera acquisition speed, which with current sCMOS cameras is up to 100 full frames per second (but collecting smaller ROIs can provide ~10× higher imaging speed). It was found that with the 4× objective, the entire nervous system could be imaged in a single frame. As the larval zebrafish are longer rostro-caudally than they are wide, smaller ROIs (in the direction of the line-by-line readout of the sCMOS camera) could be used to achieve higher frame rates.

SPED light sheet capability was demonstrated in this context by performing 12 volumes/second (0.9 mm×0.4 mm×0.2 mm, 40 z-slices) imaging of the entire brain and 6.23 volumes/second (3 mm×0.5 mm×0.2 mm, 39 z-slices) imaging of the entire nervous system including the fully-extended spinal cord; moreover, with 10× magnification 4.14 volumes/second could be recorded over the whole brain and proximal spinal cord (FIGS. 5A-5C, FIGS. 13-15). Finally, it was possible to perform automated image segmentation to globally identify all labeled cells, resulting in datasets well-suited for advanced statistical analyses of time-series data. As an example, clustering analysis was performed based on the activity time-series of each segmented cell; FIGS. 6A-6C and FIGS. 16A-16B, 17A-17B, 18A-18B provide examples of statistically-identified modules of synchronously active neurons. This type of global functional segmentation may now enable in-depth analysis of functional connectivity and high-speed neuronal ensemble relationships at the whole-nervous system level.

FIGS. 5A-5C. Rapid cellular-resolution functional mapping of the entire larval zebrafish nervous system. The camera-frame-rate limited volumetric imaging speed of SPED light sheet was demonstrated by performing rapid cellular-resolution functional mapping of the nervous system of 10 dpf Tg(elav13:H2B-GCaMP6s) zebrafish larvae. Three smaller regions of interests (ROIs) of the camera frame were used to image: (FIG. 5A) the entire nervous system with a 4×/0.28 NA objective at 6.23 volumes per second (3 mm×0.5 mm×0.2 mm, 39 z-slices), (FIG. 5B) the whole brain with a 4×/0.28 NA objective at 12 volumes per second (0.9 mm×0.4 mm×0.2 mm, 40 z-slices), and (FIG. 5C) the whole brain and spinal cord with a 10×/0.25 NA objective at 4.14 volumes per second (1.2 mm×0.43 mm×0.2 mm, 39 z-slices). The maximum intensity projection images were generated from a collapsed 3D volume generated by voxel-wise standard deviation across the entire recording durations. The cellular resolution was demonstrated by several examples of activity traces ($\Delta F/F$ vs. time) of neurons marked by colored arrows, and of neighboring cells shown in optical slices from respective volumes and their automated 3D segmentation. Also see FIGS. 10-12 for the top 99 example activity traces (ordered according to the variance across time) from the three datasets.

Figure 6A:
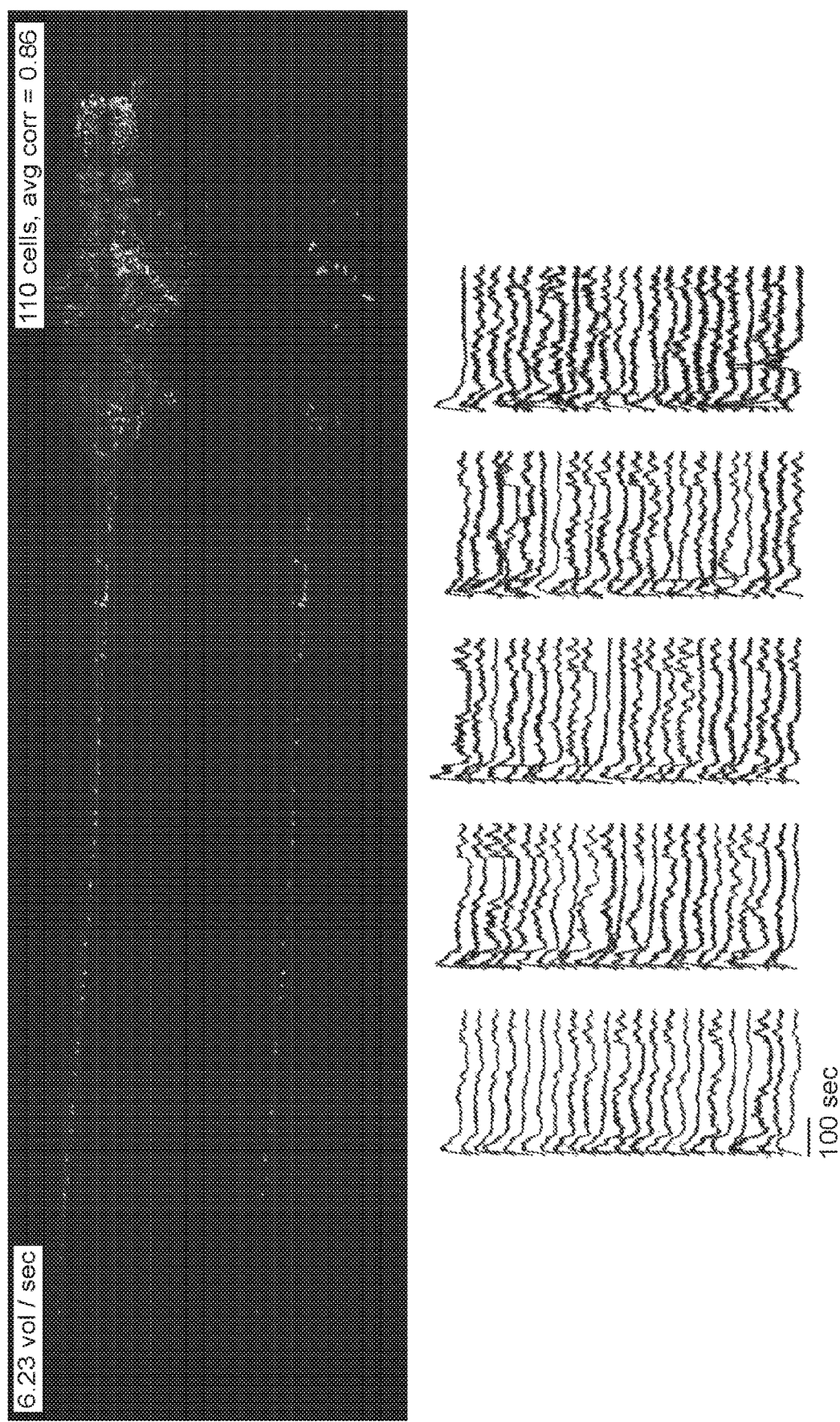
FIGS. 6A-6C are a collection of images and graphs showing rapid automated analysis of a functioning vertebrate nervous system at cellular resolution using SPED light sheet microscopy, according to embodiments of the present disclosure.
Figure 6B:
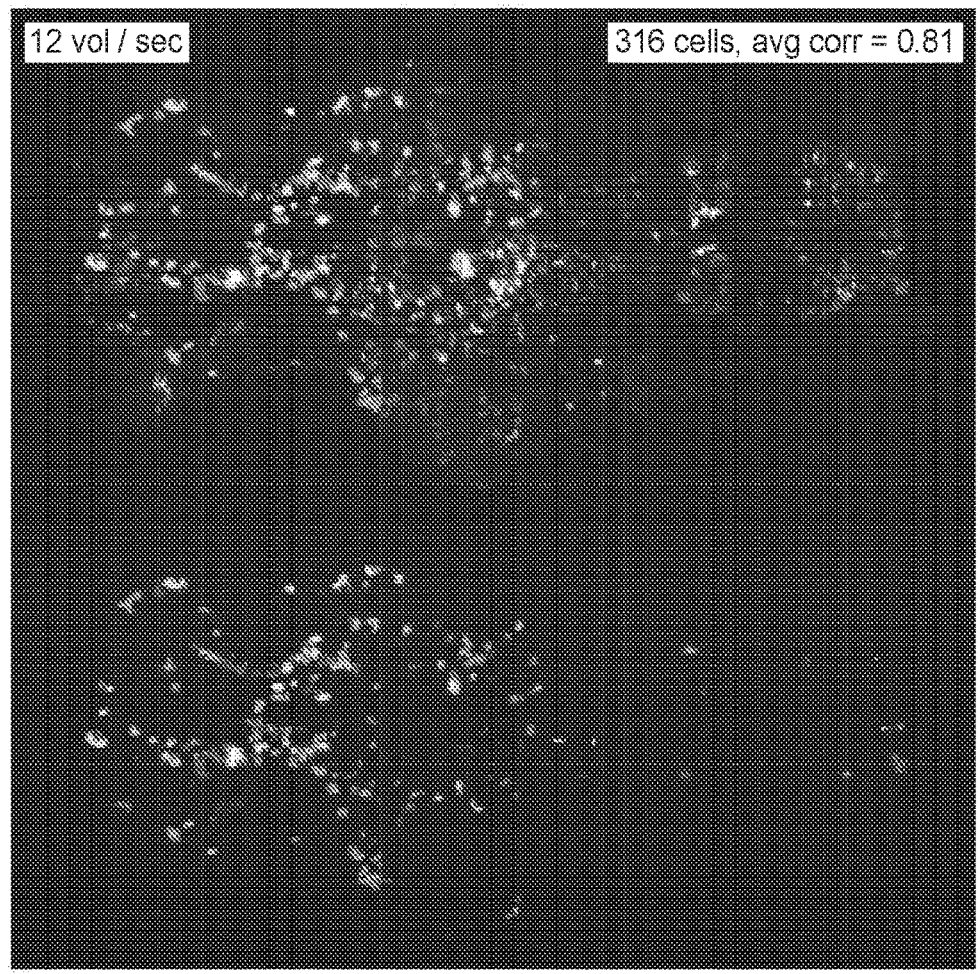
Figure 6B:
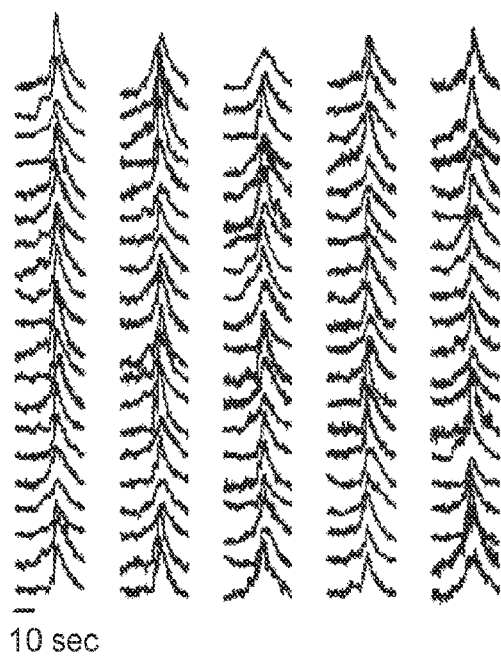
Figure 6C:
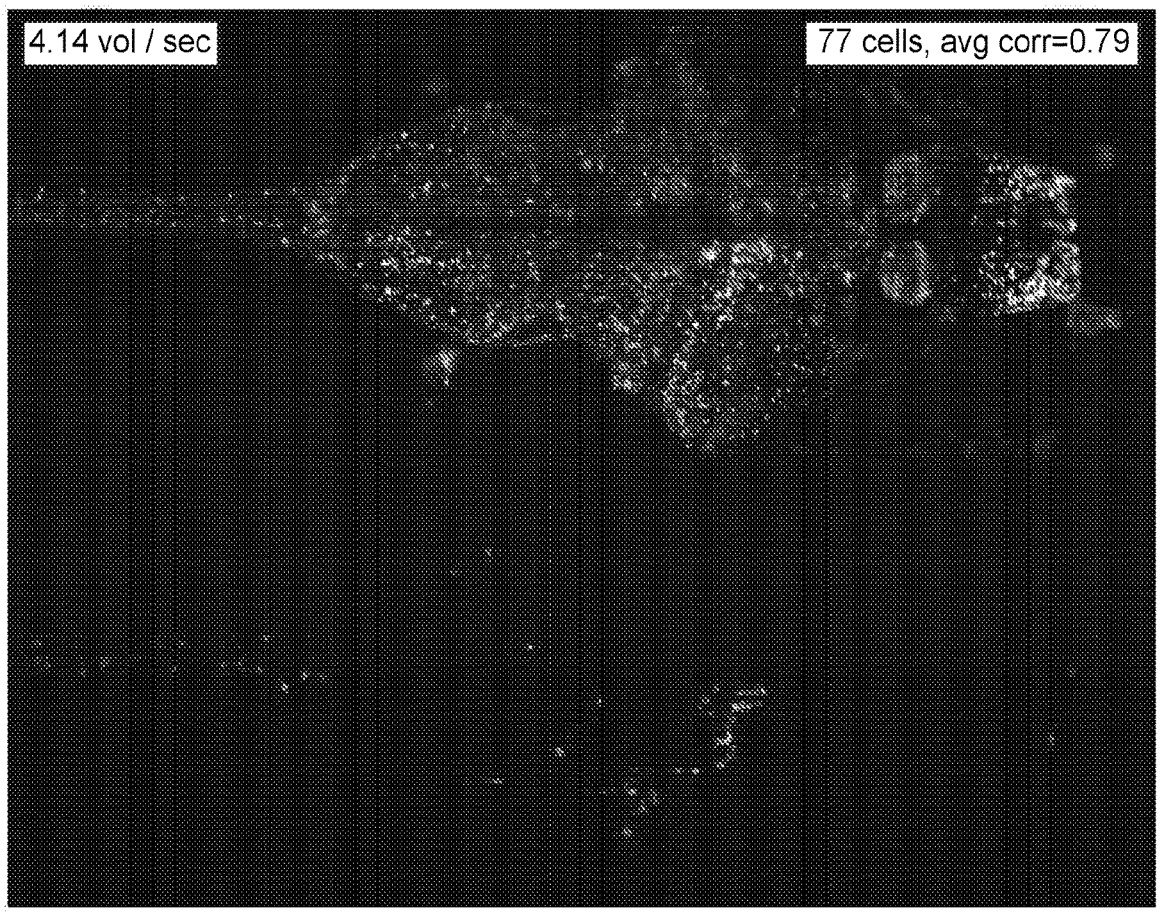
Figure 6C:
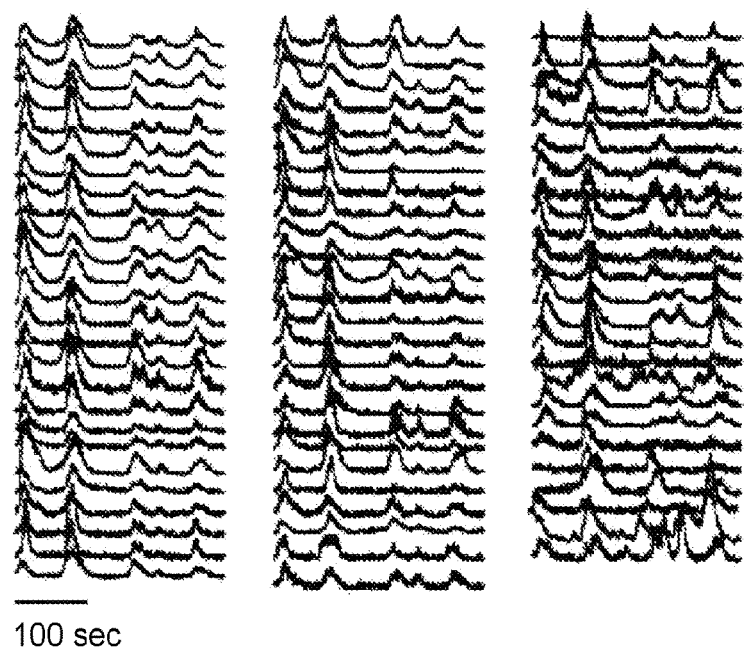

FIGS. 6A-6C. SPED light sheet imaging enables rapid automated analysis of the functioning vertebrate nervous system at cellular resolution. Compatibility of SPED light sheet datasets with global cellular-resolution analyses was demonstrated by performing clustering of neurons across entire nervous system to identify ensembles of synchronously active neurons. A hybrid of hierarchical and partitioning clustering methods (Hopach; see Methods) was used for clustering similarly active neurons across the entire nervous system. First, automated 3D image segmentation was performed on a collapsed 3D volume, generated by calculating voxel-wise standard deviation across the entire recording durations. The segmented neuron labels were overlaid on the respective time series volumes to calculate ΔF/F for all the identified cells, which were then used for performing the clustering analysis. (FIGS. 6A-6C) visualizes spatial distributions and activity profiles of neurons, all from a single example cluster from the analysis of the three datasets recorded with 4×/0.28 NA/6.23 volumes per second (3 mm×0.5 mm×0.2 mm, 39 z-slices) yielding 7 significant clusters, 4×/0.28 NA/12 volumes per second (0.9 mm×0.4 mm×0.2 mm, 40 z-slices) yielding 10 significant clusters and 10×/0.25 NA/4.14 volumes per second (1.2 mm×0.43 mm×0.2 mm, 39 z-slices) yielding 13 significant clusters. Spatial distributions of clustered neurons (differently colored only for visualization; all traces and labeled cells came from the same single cluster of neurons) were visualized by overlaying on the maximum intensity projections of standard deviation volumes. Average correlations were the mean of correlations of individual activity time series of all neurons in a cluster with the corresponding cluster average activity time series. Also see FIGS. 13-15 for additional clustering examples.

Figure 13:
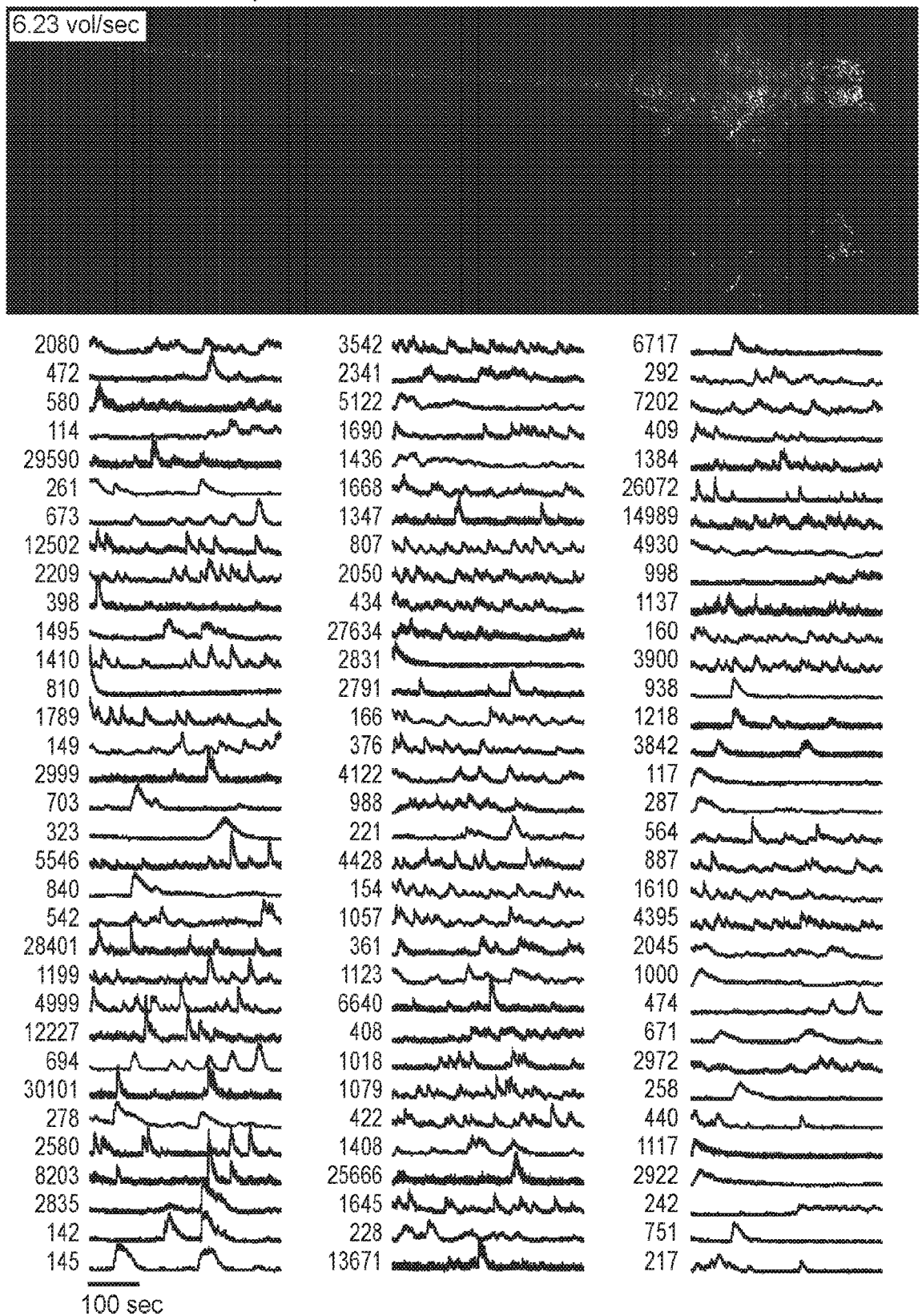
FIG. 13 is a collection of images and graphs showing a neuronal activity time series across the intact nervous system measured using SPED light sheet microscopy, according to embodiments of the present disclosure.

FIG. 13. Neuronal activity time series across the intact nervous system; related to FIGS. 5A-5C. Neuronal activity traces (ΔF/F) are shown for top 99 most active neurons in the larval zebrafish nervous system (assessed by variance across the entire recording duration), imaged using 4×/0.28 NA objective at 6.23 volumes/second (3 mm×0.5 mm×0.2 mm, 39 z-slices). Spatial distribution of identified cells was overlaid on the Maximum Intensity Projection image of voxel-wise standard deviation across the entire recording duration. Numeric labels on the traces correspond to the identified cell IDs in the segmented volume.

Figure 14:
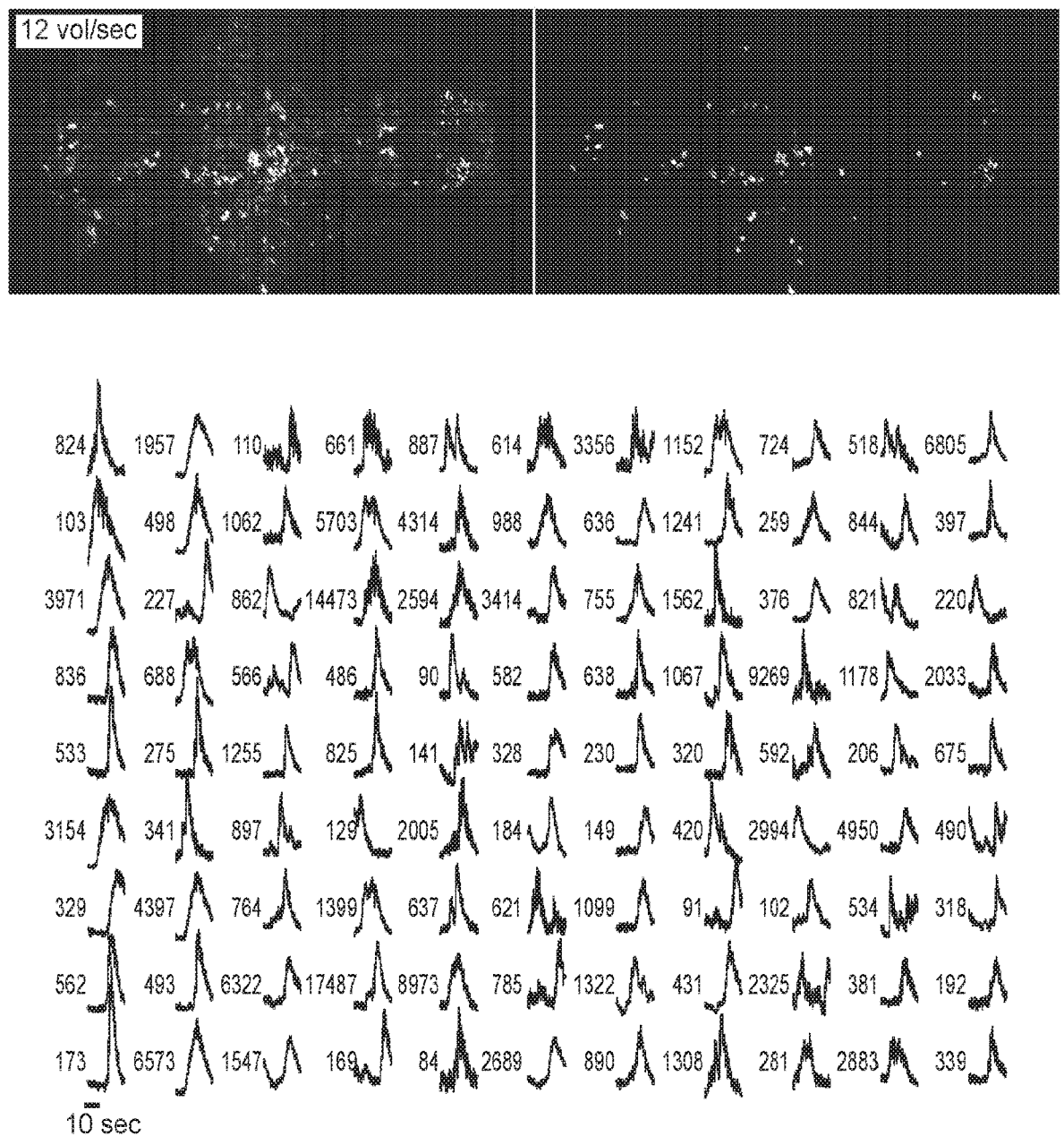
FIG. 14 is an additional collection of images and graphs showing a neuronal activity time series across the intact nervous system measured using SPED light sheet microscopy, according to embodiments of the present disclosure.

FIG. 14. Additional neuronal activity time series across the intact nervous system; related to FIGS. 5A-5C. Neuronal activity traces (ΔF/F) are shown for top 99 most active neurons in the larval zebrafish brain (assessed by their variance across the entire recording duration), imaged using 4×/0.28 NA objective at 12 volumes per second (0.9 mm×0.4 mm×0.2 mm, 40 z-slices). Spatial distribution of identified cells was overlaid on the Maximum Intensity Projection image of voxel-wise standard deviation across the entire recording duration. Numeric labels on the traces correspond to the identified cell IDs in the segmented volume.

Figure 15:
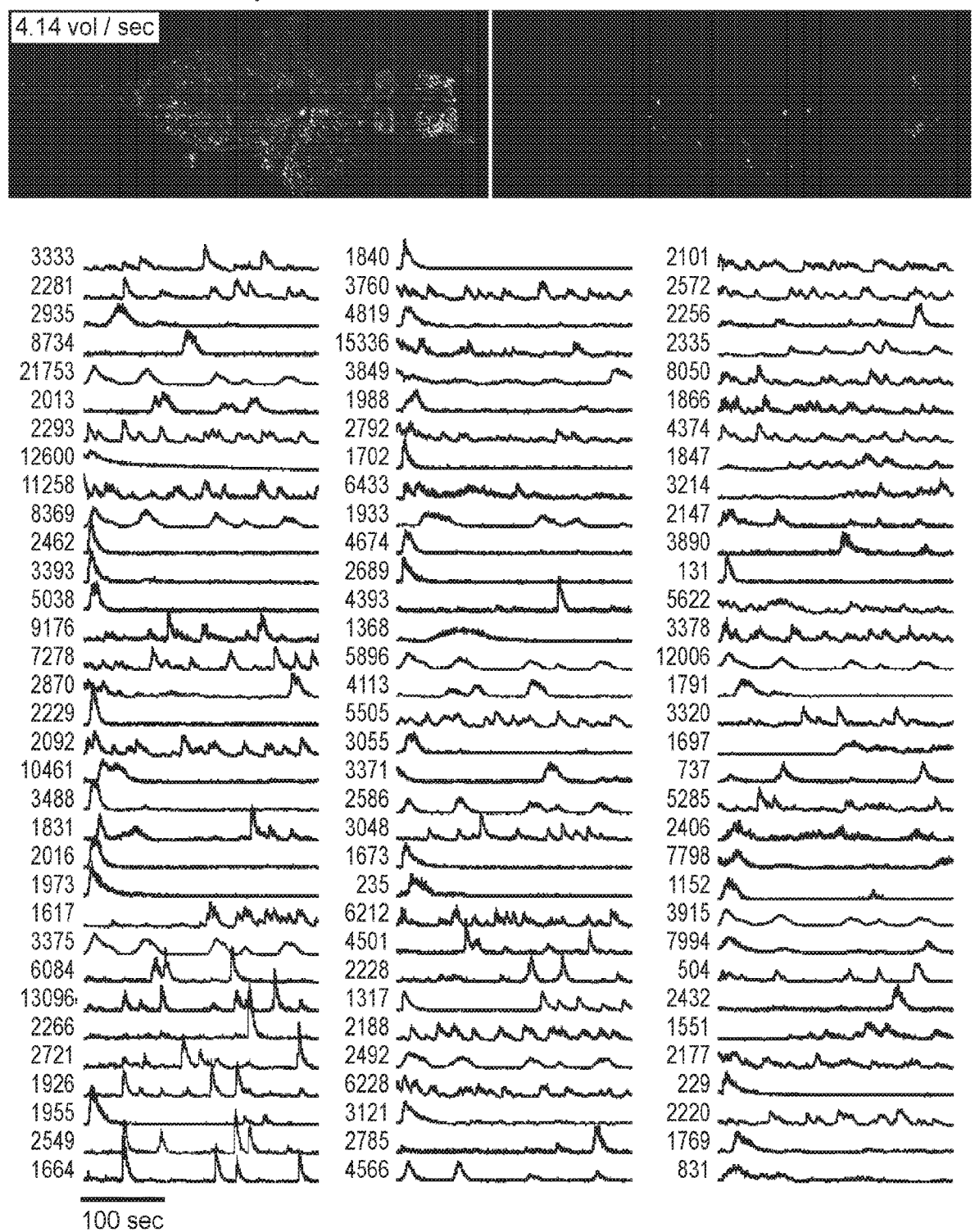
FIG. 15 is an additional collection of images and graphs showing a neuronal activity time series across the intact nervous system measured using SPED light sheet microscopy, according to embodiments of the present disclosure.

FIG. 15. Additional neuronal activity time series across the intact nervous system; related to FIGS. 5A-5C. Neuronal activity traces (ΔF/F) are shown for top 99 most active neurons in the larval zebrafish central nervous system (assessed by their variance across the entire recording duration), imaged using 10×/0.25 NA objective at 4.14 volumes per second (1.2 mm×0.43 mm×0.2 mm, 39 z-slices). Spatial distribution of identified cells was overlaid on the Maximum Intensity Projection image of voxel-wise standard deviation across the entire recording duration. Numeric labels on the traces correspond to the identified cell IDs in the segmented volume.

Figure 16A:
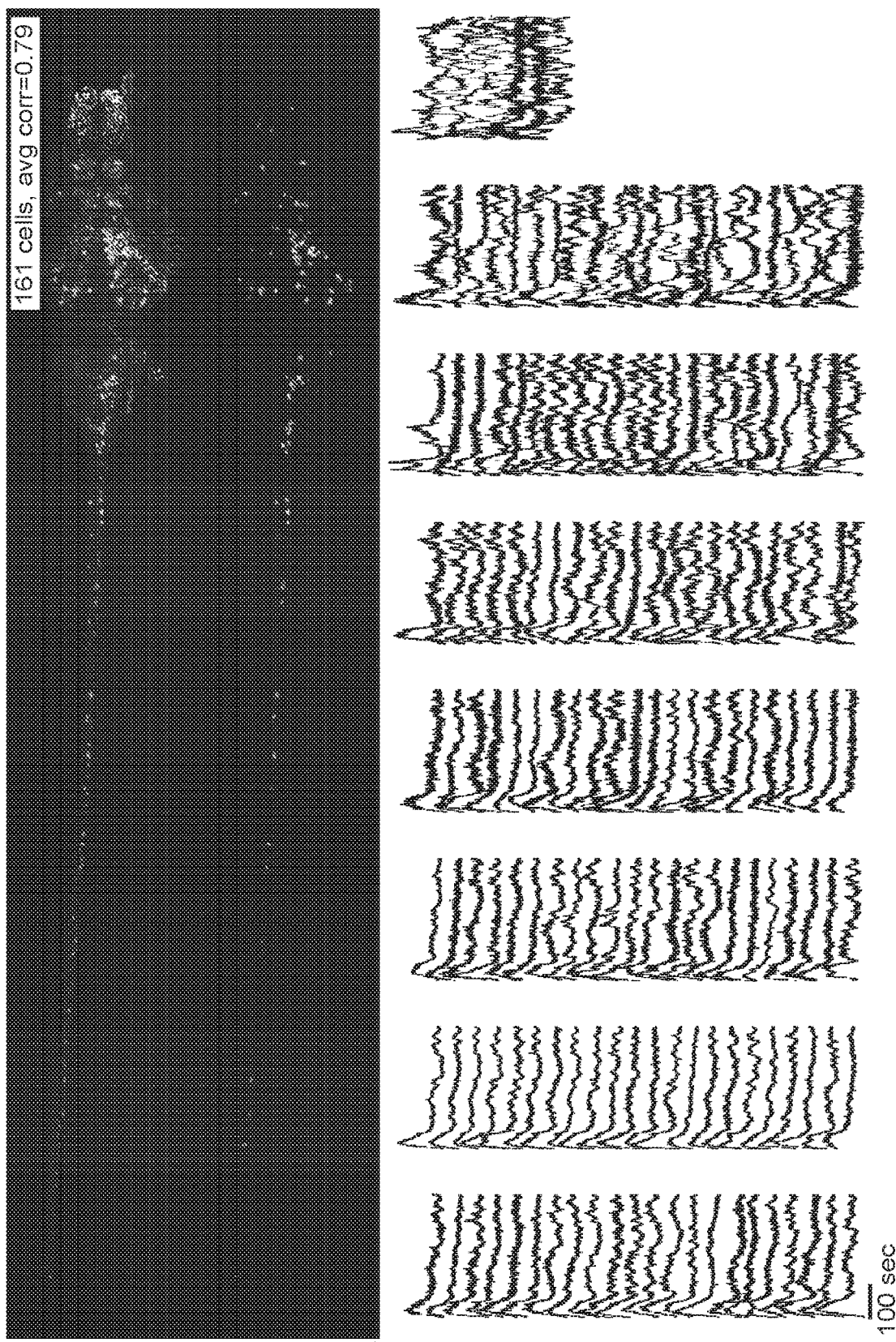

FIGS. 16A-16B. Synchronously active neuronal ensembles in whole-nervous system time series data; related to FIGS. 6A-6C. Clusters of synchronously active neurons were identified using a hybrid of hierarchical and partitioning clustering approach (Hopach; see Example 1). (FIGS. 16A-16B) show spatial distributions and activity profiles of two identified modules (in addition to FIGS. 6A-6C) in the whole nervous system data set recorded at 6.23 volumes per second (3 mm×0.5 mm×0.2 mm, 39 z-slices) using a 4×/0.28 NA objective. Average correlations were the average of correlations of all traces in a cluster with the average trace.

Figure 17A:
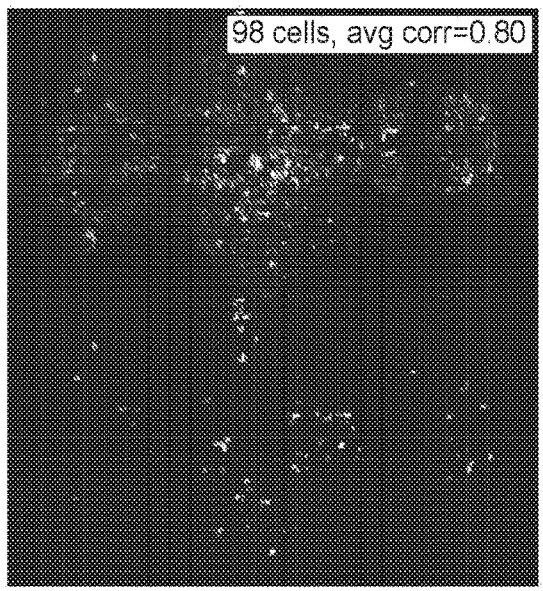
FIGS. 17A-17B are additional collections of images and graphs showing synchronously active neuronal ensembles in whole-nervous system time series data measured using SPED light sheet microscopy, according to embodiments of the present disclosure.
Figure 17A:
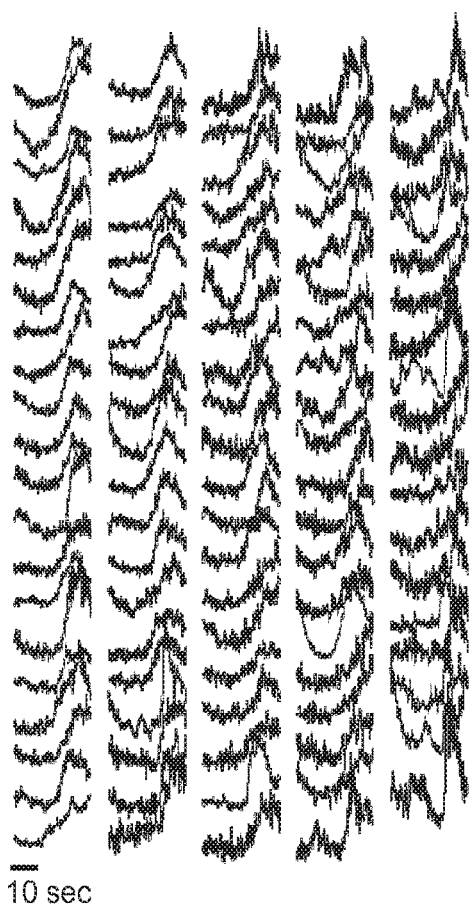
Figure 17B:
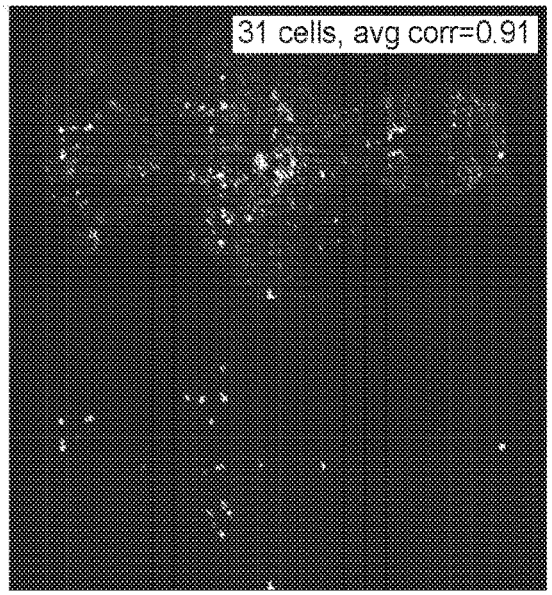
Figure 17B:

FIGS. 17A-17B. Additional synchronously active neuronal ensembles in whole-nervous system time series data; related to FIGS. 6A-6C. As in FIG. 13, clusters of synchronously active neurons were identified using a hybrid of hierarchical and partitioning clustering approach (Hopach; see Example 1). (FIGS. 17A-17B) show spatial distributions and activity profiles of two identified modules (in addition to FIGS. 6A-6C) in the whole brain time series data set recorded at 12 volumes per second (0.9 mm×0.4 mm×0.2 mm, 40 z-slices) using 4×/0.28 NA objective. Average correlations were the average of correlations of all traces in a cluster with the average trace.

FIGS. 18A-18B. Synchronously active neuronal ensembles in whole-brain time series data; related to FIGS. 6A-6C. Clusters of synchronously active neurons were identified using a hybrid of hierarchical and partitioning clustering approach (Hopach; see Example 1). (FIGS. 18A-18B) show spatial distributions and activity profiles of two identified modules (in addition to FIGS. 6A-6C) in the whole brain time series data set recorded at 4.14 volumes per second (1.2 mm×0.43 mm×0.2 mm, 39 z-slices) using 10×/0.25 NA objective. Average correlations were the average of correlations of all traces in a cluster with the average trace.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method for imaging a biological sample, the method comprising: a) scanning a biological sample using one or more light sheets, wherein the biological sample, or a portion thereof, is in a field of view of a microscope comprising an objective having an objective refractive index, wherein a direction of observation of the objective defines a z-axis and a medium is disposed between the sample and the objective, thereby illuminating a plurality of z-axial slices of the biological sample, each z-axial slice having an average slice thickness in the z-axial direction, wherein the medium has a refractive index that is different from the objective refractive index, and the biological sample is at a z-axial distance from the objective; and b) recording a plurality of images corresponding to the plurality of z-axial slices of the sample, wherein the plurality of images are generated by a plurality of light patterns emitted from the scanned biological sample, thereby generating an image stack comprising a plurality of images of the biological sample, or a portion thereof, wherein the medium is configured to elongate a point spread function (PSF) in the recorded plurality of images.

2. The method of claim 1, wherein the medium has a refractive index in the range of 1.0 to 2.0.

3. The method of claim 1, wherein the medium has an average z-axial thickness in the range of 5 mm to 100 mm.

4. The method of claim 1, wherein the medium has a refractive index greater than a refractive index of the objective.

5. The method of claim 1, wherein the medium comprises air, glass, water, glycerin, oil, or a combination thereof.

6. The method of claim 1, wherein the objective has a numerical aperture in the range of 0.01 to 1.6.

7. The method of claim 1, wherein the objective is an air objective.

8. The method of claim 1, wherein the one or more light sheets illuminate a z-axial slice at the same z-axial position in the sample at a given time point during the scanning.

9. The method of claim 1, wherein the scanning comprises scanning the biological sample using two light sheets.

10. The method of claim 9, wherein the biological sample is illuminated by the two light sheets from opposite sides of the biological sample.

11. The method of claim 1, wherein the scanning comprises using one or more mirror galvanometers to position the one or more light sheets at different z-axial positions of the biological sample.

12. The method of claim 1, wherein the image stack comprises a representation of a contiguous volume of the biological sample, wherein the volume has a z-axial depth greater than the average slice thickness of each of the plurality of z-axial slices.

13. The method of claim 1, wherein adjacent slices of the plurality of z-axial slices of the sample are offset from each other by a distance in the range of 0.5 μm to 500 μm.

14. The method of claim 1, wherein each of the one or more light sheets illuminates a z-axial slice having an average slice thickness in the range of 1 μm to 20 μm in the biological sample.

15. The method of claim 1, wherein the method further comprises deconvolving each image of the image stack based on:
   i) a z-axial position of the image; and
   ii) a predetermined, z axis-dependent point spread function corresponding to the z-axial position of the image, thereby generating a deconvolved image stack comprising deconvolved images of the biological sample, or a portion thereof.

16. The method of claim 15, wherein the predetermined, z axis-dependent point spread function is an empirically determined z axis-dependent point spread function.

17. The method of claim 15, wherein the deconvolving comprises registering the image z-axial position with the predetermined, z axis-dependent point spread function.

18. The method of claim 17, wherein the registering comprises:
   deconvolving a reference image selected from an image of the image stack with a plurality of two-dimensional point spread functions at a plurality of z-axial positions of the predetermined, z axis-dependent point spread function, to generate a plurality of deconvolved reference images; and
   determining that the reference image z-axial position corresponds to a first z-axial position of a first two-dimensional point spread function when a first deconvolved reference image deconvolved by the first two-dimensional point spread function at the first z-axial position is optimized compared to other deconvolved reference images deconvolved by other two-dimensional point spread functions at other z-axial positions.

19. The method of claim 1, wherein the method further comprises analyzing the one of more images of the image stack.

20. The method of claim 19, wherein the analyzing comprises registering, morphing, warping, aligning, counting and/or quantifying one or more properties associated with the one or more images.

21. The method of claim 1, wherein the recording comprises detecting the light patterns with a charge-coupled device (CCD) or a complementary metal oxide semiconductor (CMOS) camera.

22. The method of 1 claim 1, wherein the method comprises scanning an area of the biological sample that is larger than the field of view of the microscope by horizontally translating the relative positions of the biological sample and the microscope.

23. The method of claim 1, wherein the biological sample is labeled with a detectable label.

24. The method of claim 23, wherein the biological sample is labeled with a labeled binding member that specifically binds to a cellular component in the biological sample.

25. The method of claim 24, wherein the labeled binding member is a labeled antibody or a labeled nucleic acid.

26. The method of claim 1, wherein the biological sample is a multicellular organism or a tissue.

27. The method of claim 26, wherein the tissue is an animal tissue.

28. The method of claim 26, wherein the tissue is diagnosed to be or is suspected of being a tumor, or a dysplastic, metaplastic or neoplastic growth.

29. The method of claim 26, wherein the tissue is a biopsy tissue.

30. The method of claim 26, wherein the tissue includes tissue from brain, eye, heart, liver, pancreas, muscle, bone, kidney, prostate, breast, cervix, lung, and/or ovary.

31. The method of claim 1, wherein the biological sample is a clarified biological sample.

32. The method of claim 31, wherein the method comprises, before scanning the biological sample:
   clarifying the biological sample; and
   positioning the clarified biological sample in the field of view of the microscope.

33. The method of claim 32, wherein the clarifying comprises using passive clarity technique (PACT); perfusion-assisted agent release in situ (PARS); SeeDB; ClearT; 3-dimensional imaging of solvent-cleared organs (3DISCO); immunolabeling-enabled 3-dimensional imaging of solvent-cleared organs (iDISCO); clear, unobstructed brain imaging cocktails and computational analysis (CUBIC); Scale and derivative methods thereof, hydrogel embedding, delipidation, or refractive index matching.

34. The method of claim 26, wherein the multicellular organism is an animal.

35. The method of claim 34, wherein the animal is a living animal.

36. The method of claim 1, wherein the biological sample comprises one or more cells comprising an indicator dye.

37. The method of claim 36, wherein the indicator dye is a genetically encoded indicator dye.

38. The method of claim 36, wherein the indicator dye is a calcium indicator dye.

* * * * *